(12) United States Patent
Yu et al.

(10) Patent No.: US 9,273,294 B2
(45) Date of Patent: Mar. 1, 2016

(54) TARGETED 2'-O-METHYLATION OF TELOMERASE NON-CODING RNA

(75) Inventors: Yi-Tao Yu, Rochester, NY (US); Chao Huang, Rochester, NY (US)

(73) Assignee: University of Rochester, Rochester, NY (US)

( * ) Notice: Subject to any disclaimer, the term of this patent is extended or adjusted under 35 U.S.C. 154(b) by 189 days.

(21) Appl. No.: 13/809,975

(22) PCT Filed: Jul. 15, 2011

(86) PCT No.: PCT/US2011/044237
§ 371 (c)(1),
(2), (4) Date: Mar. 27, 2013

(87) PCT Pub. No.: WO2012/009667
PCT Pub. Date: Jan. 19, 2012

(65) Prior Publication Data
US 2013/0196409 A1    Aug. 1, 2013

Related U.S. Application Data

(60) Provisional application No. 61/365,265, filed on Jul. 16, 2010.

(51) Int. Cl.
C12N 15/00 (2006.01)
C07H 21/02 (2006.01)
C12N 9/12 (2006.01)
C12N 15/11 (2006.01)

(52) U.S. Cl.
CPC .............. *C12N 9/1276* (2013.01); *C12N 15/11* (2013.01); *C12Y 207/07049* (2013.01); *C12N 2310/113* (2013.01); *C12N 2310/321* (2013.01)

(58) Field of Classification Search
None
See application file for complete search history.

(56) References Cited

U.S. PATENT DOCUMENTS 5,972,705 A * 10/1999 Fournier et al. ............... 435/440

OTHER PUBLICATIONS

Ge et al. ('Regulation of pre-mRNA splicing in Xenopus oocytes by targeted 2'-O-methylation' RNA. vol. 16(5), pp. 1078-1085 (2G Mar. 2010)).*
Allshire R.C. et al., "Human telomeres contain at least three types of G-rich repeat distributed non-randomly," *Nucleic Acids Res.* 17:4611-4627, IRL Press, United Kingdom (1989).
Bachellerie, J. P., et al., "Antisense snoRNSa: a family of nucleolar RNAs with long conriplementarities to rRNA," *Trends Biochem. Sci.* 20:261-264, Elsevier Science Ltd., England (1995).
Balakin, et al., "The RNA World of the Nucleolus: Two Major Families of Small RNAs Defined by Different Box Elements with Related Functions," *Cell* 86:823-834, Cell Press, United States (1996).

(Continued)

*Primary Examiner* — Richard Schnizer
(74) *Attorney, Agent, or Firm* — Sterne, Kessler, Goldstein & Fox P.L.L.C.

(57) ABSTRACT

Processes and C/D box small nucleolar RNAs (snoRNAs) for altering telomerase activity and altering telomerase length are described. The processes of the invention involve the use of C/D box snoRNAs for targeted 2'-O-methylation modification of nucleotides in a pseudoknot region of the telomerase RNA. Depending on their position, the 2'-O-methylation modifications can cause an increase in telomerase activity and subsequent telomere lengthening or a decrease in telomerase activity and subsequent telomere shortening.

4 Claims, 17 Drawing Sheets

(56) References Cited

OTHER PUBLICATIONS

Bazarov, A.V., et al., "P16$^{INK4a}$ Mediated Suppression of Telomerase in Normal and Malignant Human Breast Cells," *Aging Cell* 9(5):736-746, Wiley-Blackwell, England (2010).

Blackburn, E. H., et al., "Telomeres and telomerase: the path from maize, *Tetrahymena* and yeast to human cancer and aging," *Nat. Med.* 12:1133-1138, Nature Publishing Company, United States (2006).

Blasco, M. A., "Telomere length, stem cells and aging," *Nat. Chem. Biol.* 3(10):640-649, Nature Publishing Group, United States (2007).

Cavaillé, J., M. et al., "Targeted ribose methylation of RNA in vivo directed by tailored antisense RNA guides," *Nature* 383:732-735, Macmillan Journals Ltd., England (1996).

Cawthon, R.M., "Telomere measurement by quantitative PCR," *Nucleic Acids Res.* 30(10):e47, 6 pages, Oxford University Press, England (2002).

Cech, T. R., "Beginning to Understand the End of the Chromosome," *Cell* 116:273-279, Cell Press, United States (2004).

Ciien, J-L. and Greider, C.W., "Functional analysis of the pseudoknot structure in human telomerase RNA," *Proc. Natl. Acad. Sci. USA* 102:8080-8085, The National Academy of Sciences, Untied States (2005).

Chen, S.M., et al., "Effect of blocking VEGF, hTERT and Bcl-xl by multiple shRNA expression vectors on the human laryngeal squamous carcinoma xenograft in nude mice," *Cancer Biol. Ther.* 7(5):734-739, Landes Bioscience, United States (2008).

Collins, K., "The biogenesis and regulation of telomerase holoenzymes," *Nat. Rev. Mol. Cell Biol.* 7:484-494, Nature Pub. Group, England (2006).

Coussens, M., et al., "RNAi screen for telomerase reverse transcriptase transcriptional regulators identifies HIFα as critical for telomerase function in murine embryonic stem cells," *Proc. Natl. Acad. Sci. USA* 107(31): p. 13842-13847, The National Academy of Sciences, Untied States (2010).

Culver, G. M., et al., "A 2'-Phosphotranserase Implicated in tRNA Splicing Is Essential in *Saccharomyces cerevisiae*," *J Biol. Chem.* 272:13203-13210, The American Society for Biochemistry and Molecular Biology, Inc., United States (1997).

Darzacq, X., et al., "Cajal body-specific small nuclear RNAs: a novel class of 2'-O-methylation and pseudouridylation guide RNAs," *EMBO J* 21:2746-2756, European Molecular Biology Organization, Germany (2002).

Deryusheva, S. and Gall, J.G., "Small Cajal Body-specific RNAs of *Drosophilia*Function in the Absence of Cajal Bodies," *Mol. Biol. Cell* 20(24):5250-5259, The American Society for Cell Biology, United States (2009).

Fatica, A., et al.,"Yeast snoRNA accumulation relies on a cleavage-dependent/polyadenylation-independent 3'-processing apparatus," *EMBO J* 19:6218-6229, Oxford University Press, England (2000).

Friedman, K. L., et al., "Essential functions of amino-terminal domains in the yeast telomerase catalytic subunit revealed by selection for viable mutants," *Genes Dev.* 13:2863-2874, Cold Spring Harbor Laboratory Press, United States (1999).

Gardner, P.P., et al., "Rfam: Wikipedia, clans and the 'decimal' release," *Nucleic Acids Research* 39:D141-D145, Oxford University Press, England (2010).

Ge, J., et al., "Regulation of pre-mRNA splicing in *Xenopus* oocytes by targeted 2'-O-methylation," *RNA* 16:1078-1085, Cold Springs Harbor Laboratory Press, United States (2010).

Gottschling, D. E., et al., "Position Effect at S. cerevisiae Telomeres: Reversible Repression of Pol II Transcription," *Cell* 63:751-762, Cell Press, United States (1990).

Greider, C. W. and Blackburn, E.H., "Identification of a Specific Telomere Terminal Transferase Activity in Tetrahymena Extracts," *Cell* 43:405-413, Cell Press, United States (1985).

Hou, Y. M., et al., "An important 2'-OH group for an RNA-protein interaction," *Nucleic Acids Res.* 29:976-985, Oxford University Press, England (2001).

Huang, C. and Yu, Y.-T., "Targeted 2'-O Methylation at a Nucleotide within the Pseudoknot of Telomerase RNA Reduces Telomerase Activity in Vivo," *Mol. Cell Biol.* 30(18):4368-4378, American Society for Microbiology, United States (2010).

Huang. C, et al., "Post-transcriptional Modification of RNAs by Artificial Box H/ACA and Box C/D RNPs," *Methods Mol. Biol.* 718:227-244, Springer Science, United States (2011).

Kim, N.W., et al., "Specific association of Human Telomerase Activity with Immortal Cells and Cancer," *Science* 266:2011-2015. American Association for the Advancement of Science, United States (1994).

Kiss-Laszlo, Z., et al., "Site-Specific Ribose Methylation of Preribosomal RNA: A Novel Function for Small Nucleolar RNAs," *Cell* 85:1077-1088, Cell Press, United States (1996).

Kiss, T., "Small nucleolar RNA-guided post-transcriptional modification of cellular RNAs," *EMBO J* 20:3617-3622, European Molecular Biology Organization, Germany (2001).

Kiss, T., et al., "Small Nucleolar RNAs: An Abundant Group of Noncoding RNAs with Diverse Cellular Functions," *Cell* 109:145-148, Cell Press, United States (2001).

Kosciolek, B.A., et al., "Inhibition of Telomerase Activity in Human Cancer Cells by RNA Interference," *Mol. Cancer Ther.* 2(3):209-216, American Association for Cancer Research, United States (2003).

Lestrade, L., and Weber, M. J. "snoRNA-LBME-db, a comprehensive database of human H/ACA and C/D box snoRNAs,"*Nucieic Acids Res.* 34(database issue): D158-162, Oxford University Press, England (2006).

Li, S., et al., "Rapid Inhibition of Cancer Cell Growth Induced by Lentiviral Delivery and Expression of Mutant-Template Telomerase RNA and Anti-telomerase Short-Interfering RNA," *Cancer Res.* 64(14):4833-4840, American Association for Cancer, United States (2004).

Hang, X. H., et al., "The spliced leader-associated RNA is a trypanosome-specific sn(o) RNA that has the potential to guide pseudouridine formation on the SL RNA," *RNA* 8:237-246, Cambridge University Press, United States (2002).

Lingner, J., et al., "Reverse Transcriptase Motifs in the Catalytic Subunit of Telomerase," *Science* 276:561-567, American Association for the Advancement of Science. United States (1997).

Liu, B., et al., "Probing RNA in Vivo with Methylation Guide Small Nucleolar RNAs," *Methods* 23(3):276-286, Academic Press, United States (2001).

Ma, X., et al., "Pseudouridylation of yeast U2 snRNA is catalyzed by either an RNA-guided or RNA-independent mechanism," *EMBO J* 24:2403-2413, European Molecular (2005).

Maden, B. E. H., et al., "Classical and novel approaches to the detection and localization of the numerous modified nucleotides in eukaryotic ribosomal RNA," *Biochimie* 77:22-29, Elsevier, France (1995).

Maurelli, R., et al, "Inactivation of p16INK4a (inhibitor of cyclin-dependent kinase 4A) immortalizes primary human keratinocytes by maintaining cells in the stem cell compartment," *FASEB J* 20(9):1516-1518, The Federation, United States (2006).

Miller, M. C. and Collins, K., "Telomerase recognizes its template by using an adjacent RNA motif," *Proc. Natl. Acad. Sci. USA* 99:6585-6590, The National Academy of Sciences, United States (2002).

Patry, C., et al., "Small Interfering RNA-Mediated Reduction in Heterogeneous Nuclear Ribonucleoparticule A1/A2 Proteins Induces Apoptosis in Human Cancer Cells but not in Normal Mortal Lines," *Cancer Res* 63(22):7679-7688, American Association for Cancer Research, United States (2003).

Peculis, B., "RNA processing: Pocket guides to ribosomal RNA," *Curr. Biol.* 7:R480-R482, Elsevier Inc., United States (1997).

Podlevsky, J.D., et al., "The Telomerase Database," *Nucleic Acids Res.* 36(*database issue*):D339-D343, Oxford University Press, England (2008).

Qiao, F., et al., "Triple-helix structure in telomerase RNA contributes to catalysis," *Nat. Struct. Mol. Biol.* 15:634-640, Nature Publishing Group, United States (2008).

Rufer, N. et al., "Telomere length dynamics in human lymphocyte subpopulations measured by flow cytometry," *Nat. Biotechnol.* 16: 743-747, Nature Publishing Group, United States (1998).

(56) References Cited

OTHER PUBLICATIONS

Saikia, M, et al., "A systematic, ligation-based approach to study RNA modifications," *RNA* 12:2025-2033. Cold Spring Harbor Laboratory Press, United States (2006).

Seto, A. G., et al.,"A template-proximal RNA paired element contributes to *Saccharomyces cerevisiae* telomerase activity," *RNA* 9:1323-1332, Cold Spring Harbor Laboratory Press, United States (2003).

Seto, A. G., et al.,"*Saccharomyccs cerevisiae* telomerase in an Sm small nuclear ribonucleaoprotein particle," *Nature* 101:177-180, Macmillan Magazines Ltd., England (1999).

Shefer, K., et al., "A Triple Helix within a Pseudoknot Is a Conserved and Essential Element of Telomerase RNA," *Mol. Cell Biol.* 27:2130-2143, American Society for Microbiology, United States (2007).

Sijen, T., et al., "On the Role of RNA Amplification in dsRNA-Triggered Gene Silencing," *Cell* 107(4):465-476, Cell Press, United States (2001).

Singer, M. S. and Gottschling, D.E., "TLC1: Template RNA Component of *Saccharomyces cerevisiae* Telomerase," *Science* 266:404-409, American Association for the Advancement of Science, United States (1994).

Smith, C. M. and Steitz, J.A., "Sno Storm in the Nucleolus: New Roles for Myriad Small RNPs," *Cell* 89:669-672, Cell Press, United States (1997).

Szostak, J. W. and Blackburn, E. H., "Cloning Yeast Telomeres on Linear Plasmid Vectors," *Cell* 29:245-255, Cell Press, United States (1982).

Theimer, C. A., et al., "Structure of the Human Telomerase RNA Pseudoknot Reveals Conserved Tertiary Interactions Essential for Function," *Mol. Cell* 17:671-682, Elsevier Inc., United States (2005).

Tycowski, K.T., et al., "A mammalian gene with introns instead of exons generating stable RNA products," *Nature* 379(6564):464-466, Nature Publishing Group, United States (1996).

Uesugi, S., et al., "A Linear Relationship Between Electronegativity of 2'-Substituents and Conformation of Adenine Nucleosides," *Tetrahedron Letters* 20:4073-4076, Pergamon Press Ltd., England (1979).

Wang, Y., et al., "Application of combination of short hairpin RNA segments for silencing *VEGF, TERT*, and *Bcl-xl* expression in laryngeal squamous carcinoma," *Cancer Biol. Ther*. 7(6):896-901, Landes Bioscience United States (2008).

Yu, Y. T., et al., "Mechanisms and functions of RNA-guided RNA modification," in *Fine-Tuning of RNA functions by Modification and Editing*, vol. 12, H. Grosjean (Ed.), 40 pages, Springer-Verlag, Germany (2005).

Yu, Q., et al.,"*Saccharomyces cerevisiae* Linker Histone Hholp Functionally Interacts with Core Histone H4 and Negatively Regulates the Establishment of Transcriptionally Silent Chromatin*~," *J Biol. Chem.* 284:740-750, The American Society for Biochemistry and Molecular Biology, Untied States (2009).

Zappulla, D. C., et al., "Yeast telomerase RNA: A flexible scaffold for protein subunits," *Proc. Natl. Acad. Sci. USA* 101:10024-10029, The National Academy of Sciences, Untied States (2004).

Zhao, X. and Yu, Y-T, "Targeted pre-mRNA modification for gene silencing and regulation," *Nat. Methods* 5(1):95-100, Nature Publishing Group, United States (2008).

Zhao, X., et al., "An H/ACA guide RNA directs U2 pseudouridylation at two different sites in the branchpoint recognition region in *Xenopus oocyes*," *RNA* 8:1515-1525, Cambridge University Press, United States (2002).

Zhao, X., et al., "Pseudouridines in and near the branch site recognition region of U2 snRNA are required for snRNP biogenesis and pre-mRNA splicing in *Xenopus oocytes*," *RNA* 10:681-690, Cold Spring Harbor Laboratory Press, United States (2004).

\* cited by examiner

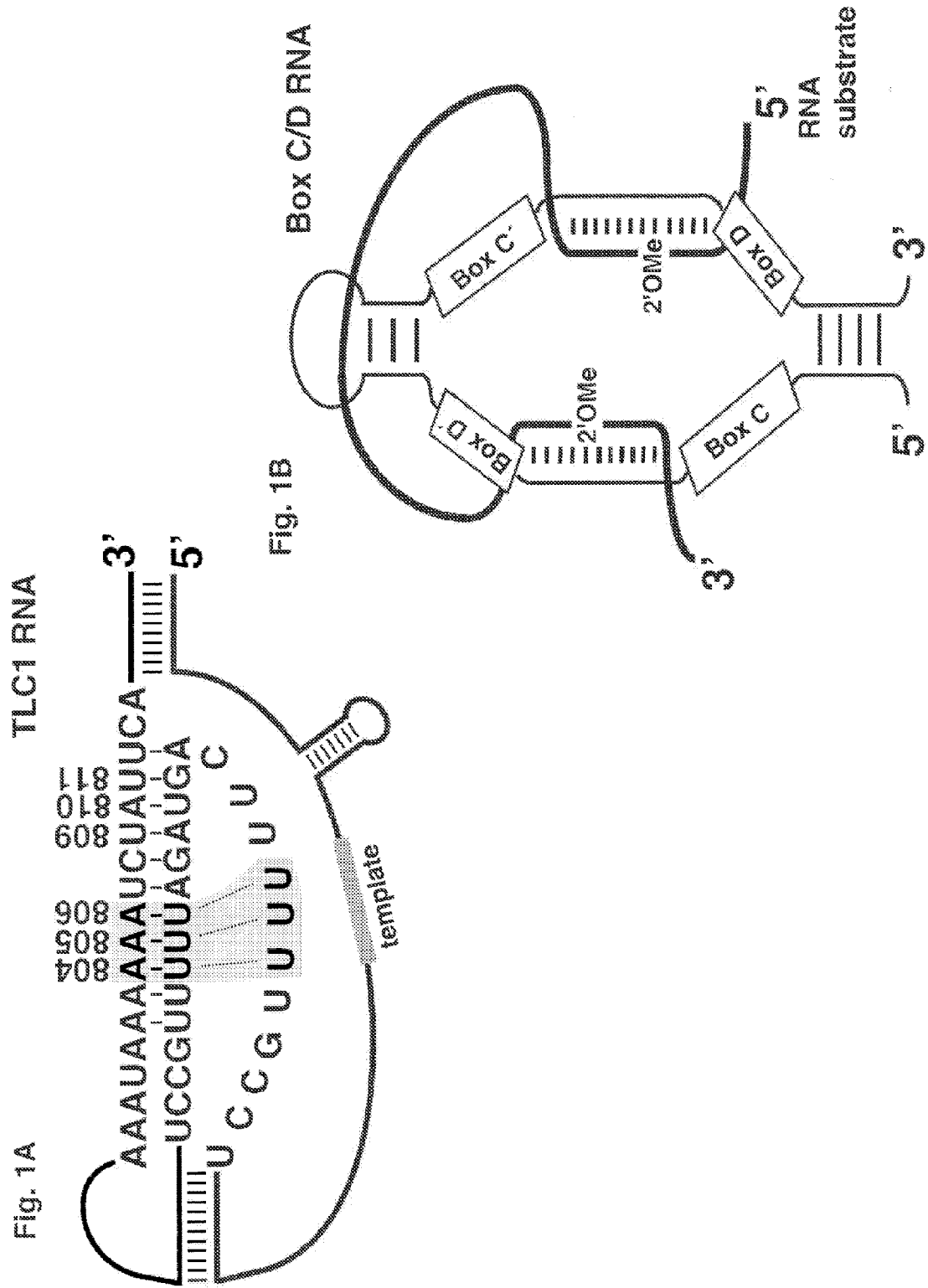

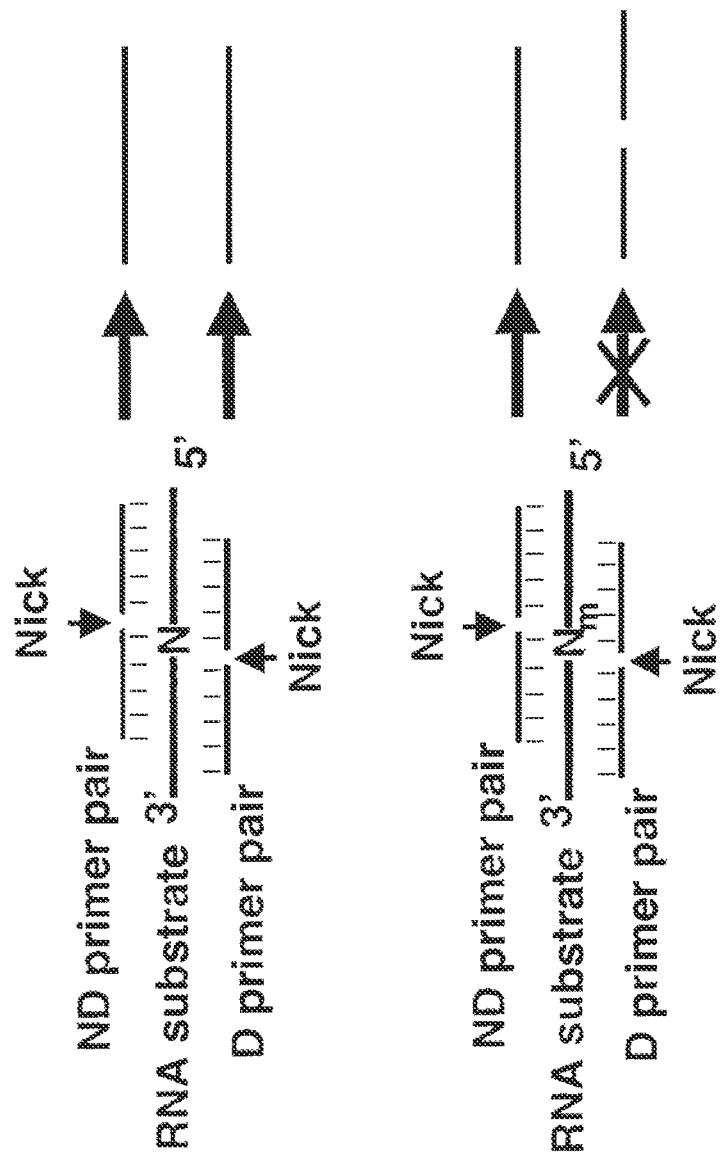

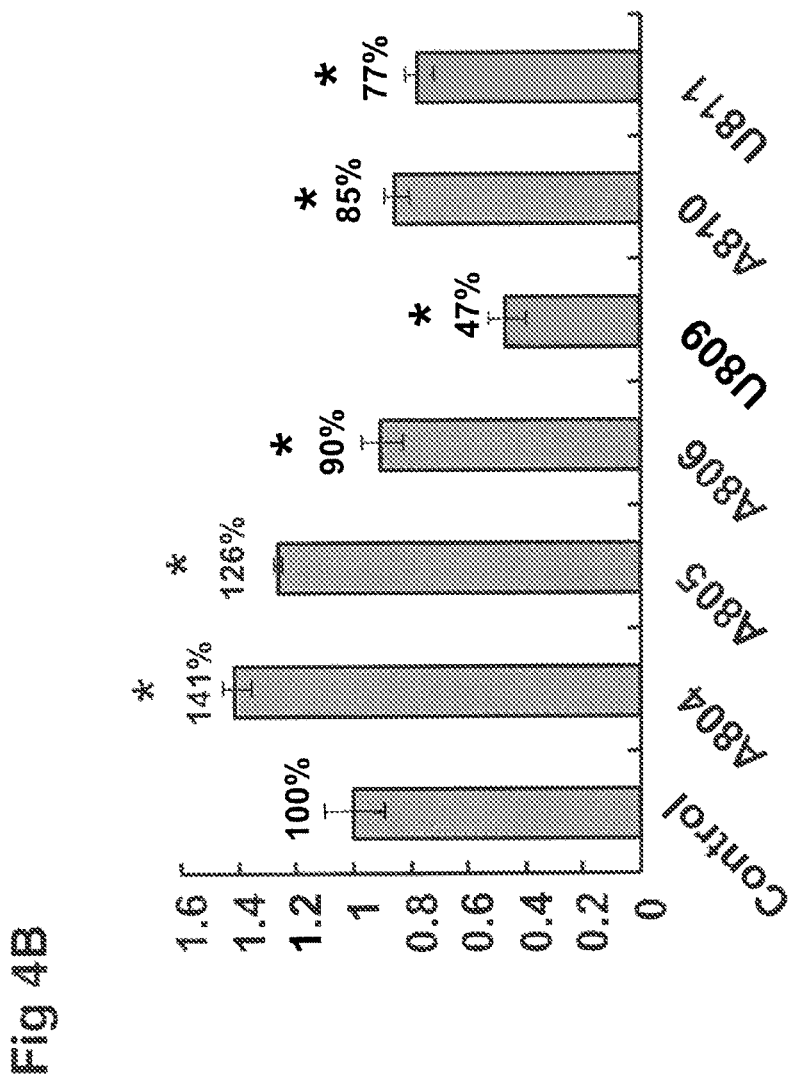

TARGETED 2'-O-METHYLATION OF TELOMERASE NON-CODING RNA

STATEMENT OF GOVERNMENT SUPPORT

This invention was made with U.S. Government support under grant number GM62937, awarded by the National Institutes of Health. The U.S. Government has certain rights in this invention.

REFERENCE TO SEQUENCE LISTING SUBMITTED ELECTRONICALLY

The content of the electronically submitted sequence listing (Name: 2973.0010001_SeqListing_Updated; Size: 125,052 bytes; and Date of Creation: May 20, 2015) filed with the application is incorporated herein by reference in its entirety.

FIELD OF THE INVENTION

The invention relates generally to methods for causing a 2'-O-methylation modification of a nucleotide in the telomerase RNA by contacting the telomerase RNA with a C/D snoRNA engineered to guide the 2'-O-methylation modification. The invention further relates generally to methods for modulating telomerase activity through 2'-O-methylation modification of a nucleotide in the telomerase RNA by contacting the telomerase RNA component with a C/D snoRNA engineered to guide the 2'-O-methylation modification. The invention further relates to engineered C/D box snoRNA molecules that may direct such modifications.

BACKGROUND OF THE INVENTION

In eukaryotic cells, chromosomal ends are capped by telomeres, which are long tandem-repeat sequences complexed with proteins (Blackburn, E. H., et al., Nat. Med. 12:1133-8 (2006); Szostak, J. W., et al., Cell 29:245-55 (1982)). Telomeres maintain the integrity and stability of chromosomes, which would otherwise undergo incomplete replication, fusion or degradation with each cell division (Cech, T. R., Cell 116:273-9 (2004); Collins, K., Nat. Rev. Mol. Cell. Biol. 7:484-94 (2006)). Telomerase is responsible for telomere elongation and maintenance of chromosomal ends in most eukaryotes (Blackburn, E. H., et al., Nat. Med. 12:1133-8 (2006); Greider, C. W., et al., Cell 43:405-13 (1985)). It has long been known that telomerase is fundamental to cell survival, growth and death (Blasco, M. A., Nat. Chem. Biol. 3:640-9 (2007)). Telomere shortening is associated with ageing and telomerase malfunction is often associated with disease. For instance, most cancer cells have an unusually high level of telomerase activity (Kim, N. W., et al., Science 266:2011-5 (1994)). On the other hand, mutations in telomerase components have been linked to several degenerative diseases such as dyskeratosis congenita and aplastic anemia (Blasco, M. A., Nat. Chem. Biol. 3:640-9 (2007)). Thus, to understand the molecular mechanisms of these diseases and to identify new treatments, it is desirable to regulate telomerase activity in vivo.

Telomerase is a ribonucleoprotein (RNP) complex (Greider, C. W., et al., Nature 337:331-7 (1989)) that consists of one noncoding RNA (known as TERC or TR in humans and TLC1 in Saccharomyces cerevisiae) (Singer, M. S., et al., Science 266:404-9 (1994)) and several proteins, including a reverse transcriptase (TERT in humans and Est2p in Saccharomyces cerevisiae) (Lingner, J., et al., Science 276:561-7 (1997)). The telomerase non-coding RNA not only folds into a structure that tethers proteins but also serves as a template for reverse transcription (Zappulla, D. C., et al., Proc. Natl. Acad. Sci. USA 101:10024-9 (2004)), which leads to the addition of a specific repeated sequence to the chromosome ends. S. cerevisiae TLC1 and its homologs in other organisms (including mammals) have been extensively studied. Several other possible functions (including catalysis) of telomerase RNA have been proposed (Miller, M. C., et al., Proc. Natl. Acad. Sci. USA 99:6585-90 (2002); Qiao, F., et al., Nat. Struct. Mol. Biol. 15:634-40 (2008)). Furthermore, NMR studies and computational modeling coupled with functional analysis have revealed a conserved triple-helix structure within the pseudoknot region of human and K. lactis telomerase RNAs (Shefer, K., et al., Mol. Cell. Biol. 27:2130-43 (2007); Theimer, C. A., et al., Mol. Cell. 17:671-82 (2005)). Recently, Qiao, et al. has presented experimental evidence for the presence of a similar triple-helix structure in yeast TLC1 RNA (Qiao, F., et al., Nat. Struct. Mol. Biol. 15:634-40 (2008)) (FIG. 1A). Changes of 2'-OH groups of nucleotides in and adjacent to the triple-helix region to 2'-H or 2'-OMe (2'-O-methylated) lead to reduction of telomerase activity in yeast and mammalian in vitro systems (Qiao, F., et al., Nat. Struct. Mol. Biol. 15:634-40 (2008)).

Box C/D ribonucleoproteins (RNPs) are modifying enzymes that introduce 2'-O-methylation into rRNAs and snRNAs at specific sites (Yu, Y. T., et al., in H. Grosjean (Ed.): Fine-Tuning of RNA Functions by Modification and Editing, vol. 12, Springer-Verlag, Berlin Heidelberg (2005)). Box C/D RNPs comprise one small RNA (box C/D RNA) and four core proteins (Fibrillarin or Nop1p in S. cerevisiae, 15.5-kDa protein, Nop56 and Nop58) (Yu, Y. T., et al., in H. Grosjean (Ed.): Fine-Tuning of RNA Functions by Modification and Editing, vol. 12, Springer-Verlag, Berlin Heidelberg (2005)). A typical box C/D RNA folds into a unique secondary structure, leaving two short sequences—one between box C and box D' and one between box C' and box D—unpaired or single stranded (FIG. 1B). These single-stranded sequences function as guides that base-pair with the natural rRNA and snRNA substrates, thereby directing 2'-O-methylation at specific sites (Bachellerie, J. P., et al., Trends Biochem. Sci. 20:261-4 (1995); Cavaille, J., M. et al., Nature 383:732-5 (1996); Kiss-Laszlo, Z., et al., Cell 85:1077-88 (1996)). Without exception, 2'-O-methylation occurs at the target nucleotide in the substrate RNA that is base-paired to the nucleotide in snoRNA precisely 5 nucleotides upstream from box D (or D'; FIG. 1B) (Cavaille, J., M. et al., Nature 383:732-5 (1996); Kiss-Laszlo, Z., et al., Cell 85:1077-88 (1996)). Once the box C/D snoRNA finds its nucleotide target, fibrillarin, a methyl transferase associated with the box C/D guide RNA, delivers the methyl group to the target nucleotide at the 2'-O position. The "Box D+5 rule" for predicting the site of 2'-O-methylation guided by box C/D RNAs has been verified in various organisms including yeast, Xenopus and human, suggesting that RNA-guided 2'-O-methylation of rRNA and snRNA is universal among eukaryotes (Kiss, T. et al., Embo J 20:3617-22 (2001); Kiss, T., et al., Cell 109:145-8 (2001); Peculis, B., Curr. Biol. 7:R480-2 (1997); Smith, C. M., et al., Cell 89:669-72 (1997)). Given the detailed mechanism of RNA-guided RNA 2'-O-methylation, it is possible to design artificial box C/D RNAs to target telomerase RNA in and adjacent to the triple-helix region, thus offering an opportunity to manipulate telomerase activity in vivo.

As disclosed in detail herein, the present inventors show that artificial box C/D RNAs can target 2'-O-methylation at specific sites in and adjacent to the triple-helix structure of telomerase, thereby affecting telomerase activity in vivo. 2'-O-methylation did not affect the steady-state level of TLC1, and 2'-O-methylated TLC1 was incorporated into telomerase RNP. Thus, these results indicate that telomerase activity can be manipulated in vivo.

SUMMARY OF THE INVENTION

The invention is directed to method for causing the 2'-O-methylation of a nucleotide at a specific position of a telomerase RNA by contacting the telomerase RNA with a C/D box snoRNA that causes 2'-O-methylation at the specific position in the telomerase RNA. The method may be performed in vivo. In certain embodiments, the method of the invention further entails assembling the modified telomerase RNA into a telomerase ribonucleoprotein complex.

In certain embodiments, the telomerase RNA is human telomerase RNA encoded by a nucleic acid comprising SEQ ID NO: 266. In certain embodiments, the C/D box snoRNA is encoded by a nucleic acid comprising a sequence selected from: SEQ ID NOs:300-314.

The invention is also directed to a method for altering telomerase enzymatic activity by providing a telomerase RNA and contacting the telomerase RNA component with a C/D box snoRNA that causes a 2'-O-methylation modification of a nucleotide in the telomerase RNA. In certain embodiments, the nucleotide that is 2'-O-methylated is located in the pseudoknot region of the telomerase RNA. The 2'-O-methylation modification of a nucleotide in the telomerase RNA alters the telomerase enzymatic activity, e.g., the modification may either increase or decrease telomerase activity.

The invention is also directed to a method for altering telomere length comprising providing a cell expressing telomerase with a telomerase RNA having and providing a nucleic acid encoding a C/D box snoRNA that causes a 2'-O-methylation modification of a nucleotide in the telomerase RNA in a manner that cause the guide RNA to be expressed in the cell. In certain embodiments, the nucleotide that is 2'-O-methyled is located in the pseudoknot region of the telomerase RNA. The 2'-O-methylation modification of a nucleotide in the telomerase RNA alters the length of telomeres in the cell, e.g., the modification may either increase or decrease telomere length.

The present invention is also directed to engineered C/D box snoRNA molecules that allow for targeted modification of the telomerase RNA. In certain embodiments, the invention is directed to nucleic acids encoding an engineered C/D box snoRNA, wherein the nucleic acid encodes a sequence comprising nucleic acids selected from SEQ ID NOs:300-314.

DESCRIPTION OF THE FIGURES

FIG. 1 shows schematic diagrams of the yeast telomerase RNA and a yeast Box C/D RNA. (A) The pseudoknot structure of *S. cerevisiae* TLC1 RNA is shown schematically (modified from (Qiao, F., et al., *Nat. Struct. Mol. Biol.* 15:634-40 (2008))). Shaded nucleotides and dotted lines denote the triple helix. The template sequence is also indicated. Nucleotides in the triple-helix region that were evaluated in the current work are numbered. (B) The box C/D RNA structure is shown schematically. Boxes C, D', C' and D are indicated. The sequence between box C and box D' and the sequence between box C' and box D function as guides that base-pair with target RNA (thick line), as shown. 2'OMe denotes the target nucleotide to be 2'-O-methylated. The two nucleotide sequences shown in FIG. 1A represent nucleotides 751-765 and 797-814 of SEQ ID NO: 282.

DETAILED DESCRIPTION

Definitions

Figure 2A:
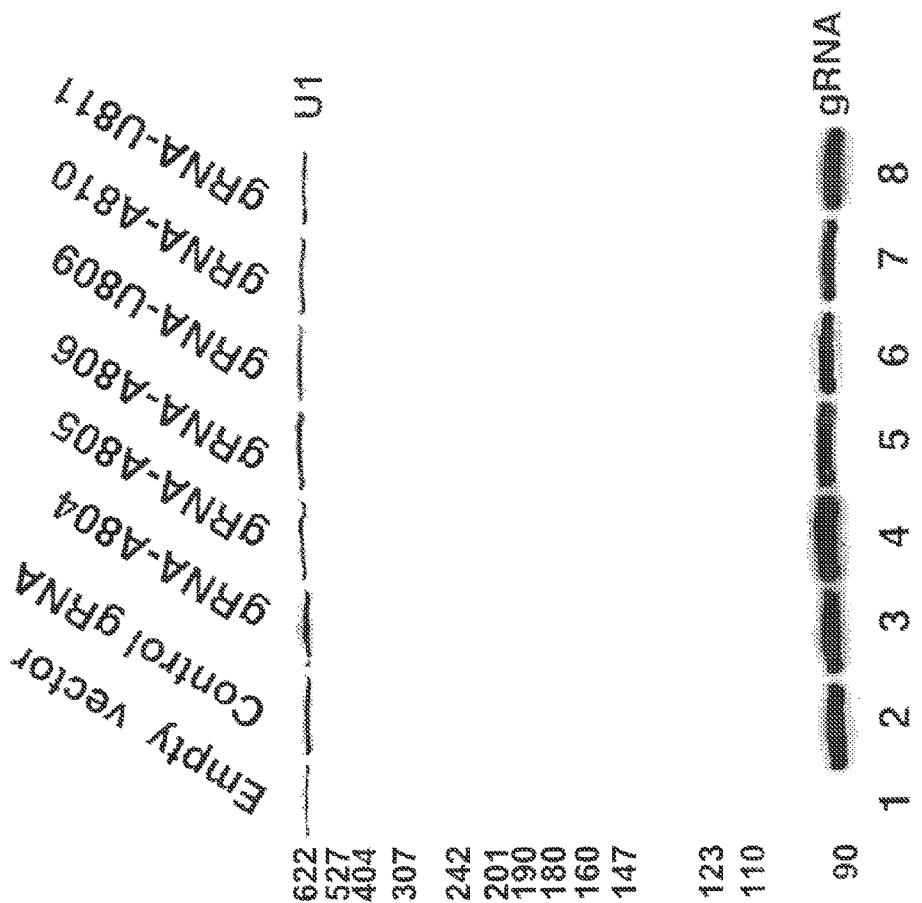
FIG. 2 shows experimental results demonstrating that Artificial box C/D guide RNAs are expressed and functional. (A) Northern blot assay for gRNA expression. Total RNA isolated from cells (yCH-001) expressing no gRNA (empty vector) (lane 1), a random (control) gRNA (lanes 2), gRNA-A804 (lane 3), gRNA-A805 (lane 4), gRNA-A806 (lane 5), gRNA-U809 (lane 6), gRNA-A810 (lane 7), or gRNA-U811 (lane 8) was used for Northern blot analysis. Probes for U1 (loading control) and gRNAs were used, and signals corresponding to these RNAs are indicated. The levels of some gRNAs are slightly lower than the others, but they were all estimated (based on northern blotting) to be higher than the endogenous naturally-occurring box C/D RNAs tested (data not shown). (B) 2'-O-methylation mapping of individually modified nucleotides. Total RNA isolated from cells (yCH-002) expressing a random gRNA (control; lanes 1 and 2), gRNA-A804 (lanes 3 and 4), gRNA-A805 (lanes 5 and 6), gRNA-A806 (lanes 7 and 8), gRNA-U809 (lanes 9 and 10), gRNA-A810 (lanes 11 and 12) or gRNA-U811 (lanes 13 and 14) was used for primer-extension analysis in the presence of high (H; 1 mM, odd-numbered lanes) or low (L; 0.001 mM, even-numbered lanes) dNTP concentrations. Arrows indicate the stop/pause signals corresponding to the 2'-O-methylated residues. The TLC1 sequencing ladder is shown on the left. (C) The strategy behind ligation-based 2'-O-methylation assay (also see Methods and text). The thick lines represent the target RNA substrate, and the thin lines stand for primer pairs (ND, non-discriminating; D, discriminating) used for ligation. N denotes a test nucleotide lacking 2'-O-methylation; Nm represents a test nucleotide that is 2'-O-methylated. Nicks (on the 5' or 3' side of the test nucleotide) are also shown. (D) Ligation-based quantification of 2'-O-methylation. RNA was isolated from cells after 30 generations that expressed a random (control) gRNA (lanes 1, 2, 5, 6, 9, 10, 13, 14, 17, 18, 21 and 22), gRNAA804 (lanes 3 and 4), gRNA-A805 (lanes 7 and 8), gRNA-A806 (lanes 11 and 12), gRNA-U809 (lanes 15 and 16), gRNA-A810 (lanes 19 and 20) or gRNA-U811 (lanes 23 and 24) and assayed for 2'-O-methylation at the respective positions with position specific primer pairs (A804, lanes 1-4; A805, lanes 5-8; A806, lanes 9-12; U809, lanes 13-16; A810, lanes 17-20; U811, lanes 21-24). D, discriminating primer pair (odd numbered lanes); N, non-discriminating primer pair (even-numbered lanes). In all lanes, an additional pair of labeled primers was also included for a loading control. The relative modification efficiencies are calculated and shown in parentheses. (E) As in (D) except that RNA was isolated from cells after 590 generations.

Unless otherwise expressly defined, the terms used herein are to be understood according to their ordinary meaning in the art. Terms used in the singular or referred to as "a" or "an" also include the plural and vice versa, unless otherwise specified or indicated by context. Standard techniques and procedures are generally performed according to conventional methods in the art and various general references (see generally, Sambrook et al. Molecular Cloning: A Laboratory Manual, 2nd ed. (1989) Cold Spring Harbor Laboratory Press, Cold Spring Harbor, N.Y., which is incorporated herein by reference), which are provided throughout this document. The disclosures of the references cited in this document are all incorporated herein by reference.

As used herein, the term "Small nucleolar RNAs (snoRNAs)" refers to a class of small non-coding RNA molecules that primarily guide chemical modifications of other RNAs, mainly ribosomal RNAs, transfer RNAs and small nuclear RNAs. There are two main classes of snoRNA, the C/D box snoRNAs which are associated with methylation modifications and H/ACA box snoRNAs which are associated with pseudouridylation modifications. snoRNAs may be represented herein as a RNA nucleic acid sequence or as a DNA nucleic acid sequence encoding the RNA nucleic acid sequence.

As used herein, the term "guide sequence" refers to a nucleic acid sequence of a snoRNA which base pairs with a target RNA molecule to guide modification of the target molecule.

As used herein, the term "engineered snoRNA" refers to a RNA for which part of the native sequence has been modified. In certain examples, engineered snoRNAs have the native guide sequence replaced with an engineered guide sequence that causes the snoRNA to target RNA modification at a specific position in the target RNA.

As used herein, the term "target RNA" or "target RNA molecule" refers to any RNA in which a modification is effected by contacting the target RNA with a snoRNA.

As used herein, the term "telomerase ribonucleoprotein complex" refers to the enzymatically functional complex of telomerase ribonucleoproteins and telomerase RNA.

As used herein, the term "telomerase RNA" or "telomerase RNA component" refers to the non-coding RNA molecule that is present in the telomerase ribonucleoprotein complex.

As used herein, the terms "altering," "modulating," or "modifying," as they relate to telomerase activity, refer to a difference in the enzymatic activity of the telomerase ribonucleoprotein complex containing a modified telomerase RNA, e.g., a telomerase ribonucleotprotein complex containing telomerase RNA having a modified nucleotide that is not present in the native telomerase RNA, when compared with the enzymatic activity of a native (wild type) telomerase, e.g., a telomerase ribonucleoprotein complex containing native telomerase RNA. A telomerase ribonucleoprotein may have increased or decreased enzymatic activity compared to wild type within the meaning of this term.

The present invention provides methods and C/D box small nucleolar RNAs (snoRNAs), or guide RNAs, that allow for the alteration of telomerase enzymatic activity and, subsequently, telomerase length. The methods of the present invention involve targeting the 2'-O-methylation modification of nucleotides in a pseudoknot region of the telomerase RNA, see, e.g., (FIG. 1A).

As is exemplified herein, 2'-O-methylation of nucleotides in a pseudoknot region of the telomerase RNA results in changes in telomere length. In certain embodiments, modification of a nucleotide at a specific position in the telomerase RNA causes reduced or decreased telomerase activity, resulting in telomere shortening. In other embodiments, modification of a nucleotide at a specific position in the telomerase RNA causes increased telomerase activity, resulting in telomere lengthening.

The present invention contemplates the use of C/D box snoRNAs for the targeted 2'-O-methylation of the telomerase RNA component. C/D box snoRNAs are known in the art. It is known that target RNA 2'-O-methylation always occurs in the residue base-paired to the nucleotide in snoRNA precisely 5 nucleotides upstream from box D (or D') (FIG. 1B) (Kiss-Laszlo, Z., et al., *Cell* 85:1077-88 (1996); Balakin, et al., *Cell* 86:823-34 (1996); Cavaille, J., M. et al., *Nature* 383:732-5 (1996)). Once the box C/D snoRNA finds its nucleotide target, fibrillarin, a methyl-transferase associated with the box C/D guide RNA, delivers the methyl group to the target nucleotide at the 2'-O position. The "Box D+5 rule" for predicting the site of 2'-O-methylation guided by snoRNAs has since been confirmed in various organisms including yeast, *Xenopus* and human (Smith, C. M., et al., *Cell* 89:669-72 (1997); Peculis, B., *Curr. Biol.* 7:R480-2 (1997); Kiss, T. et al., *Embo J* 20:3617-22 (2001); Kiss, T., et al., *Cell* 109:145-8 (2001)). Most Box D or D' sequences are CUGA while some less conserved Box D or D' sequences may be AUGA as is well known to a person of skill in the art.

The present invention provides a novel, improved way to regulate telomerase activity. Over the years, a number of different strategies have been developed for up- or down-regulating telomerase activity in various organisms. Among them, the antisense RNA approach and RNA interference (RNAi) to regulate mammalian telomerase activity have drawn a great deal of attention. Although well conceptualized, the antisense RNA approach is effective for only a few cases, and most trials have failed for a number of reasons.

One of the most important reasons for the failure of antisense RNA trials is the instable nature of a foreign antisense RNA when introduced into cells. Usually, the antisense RNA is significantly degraded before reaching its target. The development of RNAi strategies has changed the way gene silencing can be achieved. Using the RNAi strategies, several labs have knocked down telomerase RNA, the protein components of telomerase RNP, or proteins that are relevant to telomerase function, thus inhibiting telomerase activity (Wang, Y., et al., *Cancer Biol. Ther.* 7(6):896-901 (2008);

Chen, S. M., et al., *Cancer Biol. Ther.* 7(5):734-739 (2008); Kosciolek, B. A., et al., *Mol. Cancer. Ther.* 2(3):209-16 (2003); Li, S., et al., *Cancer Res.* 64(14):4833-40 (2004); Patry, C., et al., *Cancer Res* 63(22):7679-88 (2003); Coussens, M., et al., *Proc. Natl. Acad. Sci. USA* 107 (31): p. 13842-7 (2010)). In some cases, knockdown of proteins that negatively impact telomerase function (e.g., those that block telomerase recruitment to telomeres or suppress hTERT expression) can upregulate telomerase activity (Maurelli, R., et al., *FASEB J* 20(9):1516-8 (2006); Bazarov, A. V., et al., *Aging Cell* 9(5):736-46 (2010)). However, although convenient and widely used, the RNAi approach also has some limitations. For instance, the knock down of a gene usually requires many trials with different siRNAs—there are no exact rules for siRNA design. With regard to genes for which RNAi has an effect, they are usually just moderately "knocked down". In at least some organisms reported (e.g., *C. elegans*), the RNAi effect is less specific, probably due to transitive RNAi by a secondary siRNA (Sijen, T., et al., *Cell* 107(4):465-76 (2001)).

In comparison, the use of RNA-guided modifications targeted to telomerase RNA is advantageous in many different ways. First, RNA-guided RNA modification is absolutely conserved across species, from yeast to humans (Yu, Y. T., et al., in H. Grosjean (Ed.): Fine-Tuning of RNA Functions by Modification and Editing, vol. 12, Springer-Verlag, Berlin Heidelberg (2005)). Thus, this approach is, in principle, applicable to all eukaryotes. Second, guide RNAs are stable in cells (Balakin, et al., *Cell* 86:823-34 (1996)); Tycowski, K. T., et al., *Nature* 379(6564):464-6 (1996)). Just as their native counterparts, foreign guide RNAs, when introduced into cells, they are assembled into RNA-protein complexes that are stable presumably throughout the lifetime of cells, and possibly are even passed on to subsequent generations. Third, there are simple and clear rules for guide RNA design (Huang, C. et al., *Mol. Cell. Biol.* 30(18):4368-78 (2010). To target different sites within telomerase RNA for modification, only the guide sequence of a guide RNA needs to be changed accordingly. Fourth, as shown in the examples below, modification is highly efficient—for a given site more than 70% of modification was observed. Fifth, based on a large amount of experimental evidence and experience (Huang, C. et al., *Mol. Cell. Biol.* 30(18):4368-78 (2010); Zhao, X. et al., *Nat. Methods* 5 (1): p. 95-100 (2008)). RNA-guided nucleotide 2'-O-methylation is extremely site-specific. Indeed, modification occurs only in the target site in telomerase RNA or in other RNA. Sixth, as shown in the examples below, depending on the sites to which 2'-O-methylation is targeted, telomerase activity can be either enhanced or inhibited, thus offering an opportunity to manipulate telomerase activity in both directions. Finally, targeted 2'-O-methylation also offers a unique opportunity to investigate the functionality of the RNA backbone (particularly, 2'-OH moieties) (Huang, C. et al., *Mol. Cell. Biol.* 30(18):4368-78 (2010); Zhao, X. et al., *Nat. Methods* 5 (1): p. 95-100 (2008)), which has proved to be difficult to study in vivo (mutation of the 2'-OH at the DNA level is impossible).

snoRNAs

For the guided modification mechanisms of the present invention, the snoRNA guide sequences can be modified to base pair with a sequence of the target telomerase RNA adjacent to the nucleotide to be modified. The engineered snoRNA guide sequences should be made to base pair with the appropriate sequence in the target RNA so that the nucleotide is in the proper position to undergo modification.

The present invention contemplates the use of C/D box snoRNAs engineered to effect a 2'-O-methylation modification at a specific position of the subject telomere RNA. C/D box RNAs vary across species, but all allow for 2'-O-modification at the "Box D+5" position. Therefore, C/D box snoRNAs from various species may be targeted to a specific residue by placing a guide sequence upstream of Box D of the snoRNA so that the residue to be modified is 5 nucleotides upstream from Box D. For example, in the case of most snoRNAs, the residue to be modified is 5 nucleotides upstream from the C of the CUGA Box D sequence. With this method, almost any C/D box snoRNA may be engineered to effect 2-O-methyl modification of a selected base in a target telomerase RNA.

One of skill in the art will recognize that almost any human C/D box snoRNA may be used in the present invention. Examples of nucleic acids encoding human C/D box snoRNAs that may be modified for use with the present invention, named according to the HUGO Gene Nomenclature Committee convention, include: SNORD 14A (SEQ ID NO: 1), SNORD 14B (SEQ ID NO: 2), SNORD 15A (SEQ ID NO: 3), SNORD 15B (SEQ ID NO: 4), SNORD 16 (SEQ ID NO: 5), SNORD 17 (SEQ ID NO: 6), SNORD 18A (SEQ ID NO: 7), SNORD 18B (SEQ ID NO: 8), SNORD 18C (SEQ ID NO: 9), SNORD 19 (SEQ ID NO: 10), SNORD 19B (SEQ ID NO: 11), SNORD 20 (SEQ ID NO: 12), SNORD 21 (SEQ ID NO: 13), SNORD 22 (SEQ ID NO: 14), SNORD 23 (SEQ ID NO: 15), SNORD 24 (SEQ ID NO: 16), SNORD 25 (SEQ ID NO: 17), SNORD 26 (SEQ ID NO: 18), SNORD 27 (SEQ ID NO: 19), SNORD 28 (SEQ ID NO: 20), SNORD 29 (SEQ ID NO: 21), SNORD 30 (SEQ ID NO: 22), SNORD 31 (SEQ ID NO: 23), SNORD 32A (SEQ ID NO: 24), SNORD 32B (SEQ ID NO: 25), SNORD 34 (SEQ ID NO: 26), SNORD 35A (SEQ ID NO: 27), SNORD 35B (SEQ ID NO: 28), SNORD 36A (SEQ ID NO: 29), SNORD 36B (SEQ ID NO: 30), SNORD 36C (SEQ ID NO: 31), SNORD 37 (SEQ ID NO: 32), SNORD 38A (SEQ ID NO: 33), SNORD 38B (SEQ ID NO: 34), SNORD 41 (SEQ ID NO: 35), SNORD 42A (SEQ ID NO: 36), SNORD 42B (SEQ ID NO: 37), SNORD 43 (SEQ ID NO: 38), SNORD 44 (SEQ ID NO: 39), SNORD 45A (SEQ ID NO: 40), SNORD 45B (SEQ ID NO: 41), SNORD 45C (SEQ ID NO: 42), SNORD 46 (SEQ ID NO: 43), SNORD 47 (SEQ ID NO: 44), SNORD 48 (SEQ ID NO: 45), SNORD 49A (SEQ ID NO: 46), SNORD 49B (SEQ ID NO: 47), SNORD 50 (SEQ ID NO: 48), SNORD 50B (SEQ ID NO: 49), SNORD 51 (SEQ ID NO: 50), SNORD 52 (SEQ ID NO: 51), SNORD 53 (SEQ ID NO: 52), SNORD 54 (SEQ ID NO: 53), SNORD 56 (SEQ ID NO: 54), SNORD 57 (SEQ ID NO: 55), SNORD 58A (SEQ ID NO: 56), SNORD 58B (SEQ ID NO: 57), SNORD 58C (SEQ ID NO: 58), SNORD 59A (SEQ ID NO: 59), SNORD 59B (SEQ ID NO: 60), SNORD 60 (SEQ ID NO: 61), SNORD 61 (SEQ ID NO: 62), SNORD 62A (SEQ ID NO: 63), SNORD 62B (SEQ ID NO: 64), SNORD 63 (SEQ ID NO: 65), SNORD 64 (SEQ ID NO: 66), SNORD 65 (SEQ ID NO: 67), SNORD 66 (SEQ ID NO: 68), SNORD 67 (SEQ ID NO: 69), SNORD 69 (SEQ ID NO: 70), SNORD 70 (SEQ ID NO: 71), SNORD 71 (SEQ ID NO: 72), SNORD 72 (SEQ ID NO: 73), SNORD 73A (SEQ ID NO: 74), SNORD 73B (SEQ ID NO: 75), SNORD 74 (SEQ ID NO: 76), SNORD 75 (SEQ ID NO: 77), SNORD 76 (SEQ ID NO: 78), SNORD 77 (SEQ ID NO: 79), SNORD 78 (SEQ ID NO: 80), SNORD 79 (SEQ ID NO: 81), SNORD 80 (SEQ ID NO: 82), SNORD 81 (SEQ ID NO: 83), SNORD 82 (SEQ ID NO: 84), SNORD 83A (SEQ ID NO: 85), SNORD 83A (SEQ ID NO: 86), SNORD 84 (SEQ ID NO: 87), SNORD 85 (SEQ ID NO: 88), SNORD 86 (SEQ ID NO: 89), SNORD 87 (SEQ ID NO: 90), SNORD 88A (SEQ ID NO: 91), SNORD 88B (SEQ ID NO: 92), SNORD 88C (SEQ ID NO: 93), SNORD 89 (SEQ ID NO: 94), SNORD 90 (SEQ ID NO: 95), SNORD91A (SEQ ID NO: 96), SNORD91B (SEQ ID NO: 97), SNORD 92 (SEQ ID NO: 98), SNORD 93 (SEQ ID NO: 99), SNORD 94 (SEQ ID NO: 100), SNORD 95 (SEQ ID NO: 101), SNORD 96A (SEQ ID NO: 102), SNORD 96B (SEQ ID NO: 103), SNORD 97 (SEQ ID NO: 104), SNORD 98 (SEQ ID NO: 105), SNORD 99 (SEQ ID NO: 106), SNORD 100 (SEQ ID NO: 107), SNORD 101 (SEQ ID NO: 108), SNORD 102 (SEQ ID NO: 109), SNORD 103A (SEQ ID NO: 110), SNORD 103B (SEQ ID NO: 111), SNORD 104 (SEQ ID NO: 112), SNORD 105A (SEQ ID NO: 113), SNORD 105B (SEQ ID NO: 114), SNORD 107 (SEQ ID NO: 115), SNORD 108 (SEQ ID NO: 116), SNORD 109A (SEQ ID NO: 117), SNORD 109B (SEQ ID NO: 118), SNORD 110 (SEQ ID NO: 119), SNORD 111A (SEQ ID NO: 120), SNORD 111B (SEQ ID NO: 121), SNORD 112 (SEQ ID NO: 122), SNORD 113-1 (SEQ ID NO: 123), SNORD 113-2 (SEQ ID NO: 124), SNORD 113-3 (SEQ ID NO: 125), SNORD 113-4 (SEQ ID NO: 126), SNORD 113-5 (SEQ ID NO: 127), SNORD 113-6 (SEQ ID NO: 128), SNORD 113-7 (SEQ ID NO: 129), SNORD 113-8 (SEQ ID NO: 130), SNORD 113-9 (SEQ ID NO: 131), SNORD 114-1 (SEQ ID NO: 132), SNORD 114-2 (SEQ ID NO: 133), SNORD 114-3 (SEQ ID NO: 134), SNORD 114-4 (SEQ ID NO: 135), SNORD 114-5 (SEQ ID NO: 136), SNORD 114-6 (SEQ ID NO: 137), SNORD 114-7 (SEQ ID NO: 138), SNORD 114-8 (SEQ ID NO: 139), SNORD 114-9 (SEQ ID NO: 140), SNORD 114-10 (SEQ ID NO: 141), SNORD 114-11 (SEQ ID NO: 142), SNORD 114-12 (SEQ ID NO: 143), SNORD 114-13 (SEQ ID NO: 144), SNORD 114-14 (SEQ ID NO: 145), SNORD 114-15 (SEQ ID NO: 146), SNORD 114-16 (SEQ ID NO: 147), SNORD 114-17 (SEQ ID NO: 148), SNORD 114-18 (SEQ ID NO: 149), SNORD 114-19 (SEQ ID NO: 150), SNORD 114-20 (SEQ ID NO: 151), SNORD 114-21 (SEQ ID NO: 152), SNORD 114-22 (SEQ ID NO: 153), SNORD 114-23 (SEQ ID NO: 154), SNORD 114-24 (SEQ ID NO: 155), SNORD 114-25 (SEQ ID NO: 156), SNORD 114-26 (SEQ ID NO: 157), SNORD 114-27 (SEQ ID NO: 158), SNORD 114-28 (SEQ ID NO: 159), SNORD 114-29 (SEQ ID NO: 160), SNORD 114-30 (SEQ ID NO: 161), SNORD 114-31 (SEQ ID NO: 162), SNORD 116-1 (SEQ ID NO: 163), SNORD 116-2 (SEQ ID NO: 164), SNORD 116-3 (SEQ ID NO: 165), SNORD 116-4 (SEQ ID NO: 166), SNORD 116-5 (SEQ ID NO: 167), SNORD 116-7 (SEQ ID NO: 168), SNORD 116-8 (SEQ ID NO: 169), SNORD 116-9 (SEQ ID NO: 170), SNORD 116-10 (SEQ ID NO: 171), SNORD 116-11 (SEQ ID NO: 172), SNORD 116-12 (SEQ ID NO: 173), SNORD 116-13 (SEQ ID NO: 174), SNORD 116-14 (SEQ ID NO: 175), SNORD 116-15 (SEQ ID NO: 176), SNORD 116-16 (SEQ ID NO: 177). SNORD 116-17 (SEQ ID NO: 178), SNORD 116-18 (SEQ ID NO: 179), SNORD 116-19 (SEQ ID NO: 180), SNORD 116-20 (SEQ ID NO: 181), SNORD 116-21 (SEQ ID NO: 182), SNORD 116-22 (SEQ ID NO: 183), SNORD 116-23 (SEQ ID NO: 184), SNORD 116-24 (SEQ ID NO: 185), SNORD 116-25 (SEQ ID NO: 186), SNORD 116-26 (SEQ ID NO: 187), SNORD 116-27 (SEQ ID NO: 188), SNORD 116-28 (SEQ ID NO: 189), SNORD 116-29 (SEQ ID NO: 190), SNORD 116-6 (SEQ ID NO: 191), SNORD 117 (SEQ ID NO: 192), SNORD 118 (SEQ ID NO: 193), SNORD 119 (SEQ ID NO: 194), SNORD 121A (SEQ ID NO: 195), SNORD 121B (SEQ ID NO: 196), SNORD 123 (SEQ ID NO: 197), SNORD 124 (SEQ ID NO: 198), SNORD 125 (SEQ ID NO: 199), SNORD 126 (SEQ ID NO: 200), SNORD 127 (SEQ ID NO: 201), SNORD 2 (SEQ ID NO: 202), SNORD 3 (SEQ ID NO: 203), SNORD 3-2 (SEQ ID NO: 2 (4), SNORD 3-2B (SEQ ID NO: 205), SNORD 3-3 (SEQ ID NO: 206), SNORD 3-4 (SEQ ID NO: 207), SNORD 4A (SEQ ID NO: 208), SNORD 4B (SEQ ID NO: 209), SNORD 5 (SEQ ID NO: 210), SNORD 6 (SEQ ID NO: 211), SNORD 7 (SEQ ID NO: 212), SNORD 8 (SEQ ID NO: 213), SNORD 9 (SEQ ID NO: 214), SNORD 10 (SEQ ID NO: 215), SNORD 11 (SEQ ID NO: 216), SNORD 12 (SEQ ID NO: 217), SNORD 12B (SEQ ID NO: 218), SNORD 12 (SEQ ID NO: 219), SNORD 13 (SEQ ID NO: 220), SNORD115-1 (SEQ ID NO: 366), SNORD115-2 (SEQ ID NO: 367), SNORD115-3 (SEQ ID NO: 368), SNORD115-4 (SEQ ID NO: 369), SNORD115-5 (SEQ ID NO: 370), SNORD115-6 (SEQ ID NO: 371), SNORD115-7 (SEQ ID NO: 372), SNORD115-8 (SEQ ID NO: 373), SNORD115-9 (SEQ ID NO: 374), SNORD115-10 (SEQ ID NO: 375), SNORD115-11 (SEQ ID NO: 376), SNORD115-12 (SEQ ID NO: 377), SNORD115-13 (SEQ ID NO: 378), SNORD115-14 (SEQ ID NO: 379), SNORD115-15 (SEQ ID NO: 380), SNORD115-16 (SEQ ID NO: 381), SNORD115-17 (SEQ ID NO: 382), SNORD115-18 (SEQ ID NO: 383), SNORD115-19 (SEQ ID NO: 384), SNORD115-20 (SEQ ID NO: 385), SNORD115-21 (SEQ ID NO: 386), SNORD115-22 (SEQ ID NO: 387), SNORD115-23 (SEQ ID NO: 388), SNORD115-25 (SEQ ID NO: 389), SNORD115-26 (SEQ ID NO: 390), SNORD115-29 (SEQ ID NO: 391), SNORD115-30 (SEQ ID NO: 392), SNORD115-31 (SEQ ID NO: 393), SNORD115-32 (SEQ ID NO: 394), SNORD115-33 (SEQ ID NO: 395), SNORD115-34 (SEQ ID NO: 396), SNORD115-35 (SEQ ID NO: 397), SNORD115-36 (SEQ ID NO: 398), SNORD115-37 (SEQ ID NO: 399), SNORD115-38 (SEQ ID NO: 400), SNORD115-39 (SEQ ID NO: 401), SNORD115-40 (SEQ ID NO: 402), SNORD115-41 (SEQ ID NO: 403), SNORD115-42 (SEQ ID NO: 404), SNORD115-43 (SEQ ID NO: 405), SNORD115-44 (SEQ ID NO: 406), SNORD115-48 (SEQ ID NO: 407), SNORD 33 (SEQ ID NO: 408), SNORD 55 (SEQ ID NO: 409), SNORD 68 (SEQ ID NO: 410), or analogues thereof, e.g., a nucleic acid or polynucleotide comprising an nucleic acid sequence at least 80%, 85%, 90%, 95%, 96%, 97%, 98%, 99%, or 100% identical to a known snoRNA sequence.

More information on human C/D box snoRNAs may be found in the LMBE snoRNABase database, which is available at www-snorna.biotoul.fr (see, Lestrade, L., and Weber, M. J. *Nucleic Acids Res.* 34 (database issue): D158-162 (2006)), as well as other databases which are well known to a person of skill in the art, such as the rFam database (rfam.sanger.ac.uk; see, P. P. Gardner, et al., *Nucleic Acids Res.* doi: 10.1093/nar/gkq1129 (2011)). The snoRNABase lists the location of the D and/or D' Box and the native guide sequences in each snoRNA, allowing for a person of skill in the art to easily locate the Box D+5 position and engineer a snoRNA for specific targeting of residues for 2'-O-methyl modification.

Many of the human C/D box snoRNAs listed above have homologs in other vertebrate species, which may also be engineered accord to the invention, including: *Macaca mulatta* (rhesus monkey), *Sus scrofa* (pig), *Danio rerio* (zebrafish), *Loxodonta africana* (African savanna elephant), *Lama pacos* (alpaca), *Cavia porcellus* (domestic guinea pig), *Bos taurus* (cattle), *Canis lupus familiaris* (dog), *Pan troglodytes* (chimpanzee), *Pongo abelii* (Sumatran orangutan), *Gorilla gorilla gorilla* (Western lowland gorilla), *Gorilla gorilla* (Western Gorilla), *Equus caballus* (horse), *Tursiops truncatus* (bottlenosed dolphin), *Myotis lucifugus* (little brown bat), *Oryctolagus cuniculus* (rabbit), *Felis catus* (domestic cat), *Rattus norvegicus* (Norway rat), *Mus musculus* (house mouse) and *Xenopus laevis* (African clawed frog). Additional snoRNAs contemplated include those from: *Danio rerio* (zebrafish); invertebrates: *Ciona intestinalis* (sea squirt), *Ciona savignyi* (sea squirt), *Strongylocentrotus purpuratus* (purple sea urchin), *Gammarus pulex* (freshwater shrimp), *Drosophila melanogaster* (fruit fly), *Drosophila virilis* (fly), *Chironomus tentans* (fly), *Anopheles gambiae* (African malaria mosquito), *Sialis lutaria* (alderfly), *Apis mellifera* (honey bee), *Bombyx mori* (domestic silkworm), *Bombyx mandarina* (wild silkworm), *Papilio xuthus* (butterfly), *Hodotermopsis japonicus* (termite), *Periplaneta fuliginosa* (dusky-brown cockroach), *Tapinoma nigerrimum* (ant), *Manica yessensis* (ant), *Myrmecia* sp. (ant); Nematodes: *Ascaris lumbricoides* (common roundworm), *Ascaris suum* (pig round worm), *Parascaris univalens, Caenorhabditis elegans*; Fungi: *Schizosaccharomyces pombe* (fission yeast), *Saccharomyces cerevisiae* (baker's yeast), *Saccharomyces pastorianus* (lager yeast), *Saccharomyces kluyveri, Kluyveromyces lactis, Candida albicans, Pichia guilliermondii, Pichia stipites, Aspergillus fumigatus, Aspergillus oryzae, Aspergillus niger* and *Neurospora crassa*. It is also contemplated that analogs of such C/D box snoRNAs may be used such as nucleic acids comprising an nucleic acid sequence at least 80%, 85%, 90%, 95%, 96%, 97%, 98%, 99%, or 100% identical to a known snoRNA sequence for each C/D box snoRNA listed above. Examples of such homologs may be found in the rFam database. As the Box D sequence is highly conserved among species and typically has the sequence CUGA or AUGA, a person of skill in the art can locate the D and/or D' Box and the native guide sequences in homolog snoRNAs. This allows for a person of skill in the art to easily locate the Box D+5 position and engineer a snoRNA for specific targeting of residues for 2'-O-methyl modification.

Still further examples of C/D box snoRNAs known in the art include the *Saccharomyces cerevisiae* snoRNAs: U14 (SEQ ID NO: 221), U18 (SEQ ID NO: 222), U24 (SEQ ID NO: 223), snR4 (SEQ ID NO: 224), snR13 (SEQ ID NO: 225), snR38 (SEQ ID NO: 226), snR39 (SEQ ID NO: 227), snR39b (SEQ ID NO: 228), snR40 (SEQ ID NO: 229), snR41 (SEQ ID NO: 230), snR45 (SEQ ID NO: 231), snR47 (SEQ ID NO: 232), snR48 (SEQ ID NO: 233), snR50 (SEQ ID NO: 234), snR51 (SEQ ID NO: 235), snR52 (SEQ ID NO: 236), snR53 (SEQ ID NO: 237), snR54 (SEQ ID NO: 238), snR55 (SEQ ID NO: 239), snR56 (SEQ ID NO: 240), snR57 (SEQ ID NO: 241), snR58 (SEQ ID NO: 242), snR59 (SEQ ID NO: 243), snR60 (SEQ ID NO: 244), snR61 (SEQ ID NO: 245), snR62 (SEQ ID NO: 246), snR63 (SEQ ID NO: 247), snR64 (SEQ ID NO: 248), snR65 (SEQ ID NO: 249), snR66 (SEQ ID NO: 250), snR67 (SEQ ID NO: 251), snR68 (SEQ ID NO: 252), snR69 (SEQ ID NO: 253), snR70 (SEQ ID NO: 254), snR71 (SEQ ID NO 255), snR72 (SEQ ID NO: 256), snR73 (SEQ ID NO: 257), snR74 (SEQ ID NO: 258), snR75 (SEQ ID NO: 259), snR76 (SEQ ID NO: 260), snR77 (SEQ ID NO: 261), snR78 (SEQ ID NO: 262), snR79 (SEQ ID NO: 263), snR87 (SEQ ID NO 264), snR190 (SEQ ID NO: 265) or analogues thereof, e.g., a nucleic acid or polynucleotide comprising an nucleic acid sequence at least 80%, 85%, 90%, 95%, 96%, 97%, 98%, 99%, or 100% identical to a known snoRNA sequence. Further information on the above listed snoRNAs and other C/D box snoRNAs can be found in the UMASS Amherst Yeast snoRNA database (people.biochem.umass.edu/sfournier/fournierlab/snornadb/main.php, see, D. Piekna-Przybylska, et al., *Rna* 13(3):305-12)(2007)).

Telomerase Target RNAs

The target RNA molecules of the present invention comprise a telomerase RNA, for example, TR (or TERC) in humans. Examples of nucleic acids encoding telomerase RNAs that are suitable targets for the present invention are listed in the Telomerase Database (telomerase.asu.edu, see, Podlevsky, J. D., et al., *Nucleic Acids Res.* 36 (database issue):

D339-D343(2008)). Examples of nucleic acids encoding telomerase RNA that may be targeted in the present invention include: vertabrates: *Homo sapiens* (human) (SEQ ID NO: 266), *Oryctolagus cuniculus* (domestic rabbit) (SEQ ID NO: 267), *Cavia porcellus* (domestic guinea pig) (SEQ ID NO: 268), *Cricetulus griseus* (Chinese hamster) (SEQ ID NO: 269), *Mus musculus* (mouse) (SEQ ID NO: 270), *Rattus norvegicus* (Norway rat) (SEQ ID NO: 271), \ *Felis catus* (cat) (SEQ ID NO: 272), *Bos taurus* (cattle) (SEQ ID NO: 273), *Sus scrofa* (pig) (SEQ ID NO: 274), *Equus caballus* (domestic horse) (SEQ ID NO: 275), *Elephas maximus* (Asian elephant) (SEQ ID NO: 276), *Gallus gallus* (chicken) (SEQ ID NO: 277), *Bombina japonica* (toad) (SEQ ID NO: 278), *Xenopus laevis* (African clawed frog) (SEQ ID NO: 279), *Danio rerio* (zebrafish) (SEQ ID NO: 280); Fungi: *Schizosaccharomyces pombe* (fission yeast) (SEQ ID NO: 281), *Saccharomyces cerevisiae* (baker's yeast) (SEQ ID NO: 282), *Saccharomyces pastorianus* (lager yeast) (SEQ ID NO: 283). *Candida albicans* (SEQ ID NO: 284), or analogues thereof, e.g., a nucleic acid or polynucleotide comprising an nucleic acid sequence at least 80%, 85%, 90%, 95%, 96%, 97%, 98%, 99%, or 100% identical to a known telomerase RNA sequence.

Telomerase RNA has a triple-helix as part of a pseudoknot structure that has been shown to be conserved and important to catalysis (Shefer, K., et al., *Mol. Cell Biol.* 27:2130-43 (2007); Qiao, F., et al., *Nat. Struct. Mol. Biol.* 15:634-40 (2008)). In certain embodiments, C/D box snoRNAs are engineered to effect 2'-O-methylation modification on a nucleotide in the pseudoknot region of the telomerase RNA. The structures and sequences for the telomerase RNAs of the present invention are available to one of skill in the art in the literature, for instance in the Telomerase Database (telomerase.asu.edu/structures.html). From review of the structure and sequence information, one of skill in the art will be able to engineer a C/D box snoRNA having a guide sequence that guides the 2'-O-methylation modification of the desired nucleotide, i.e., the nucleotide complementary to the C/D snoRNA nucleotide 5 bases upstream from the D or D box of the snoRNA.

Figure 7:
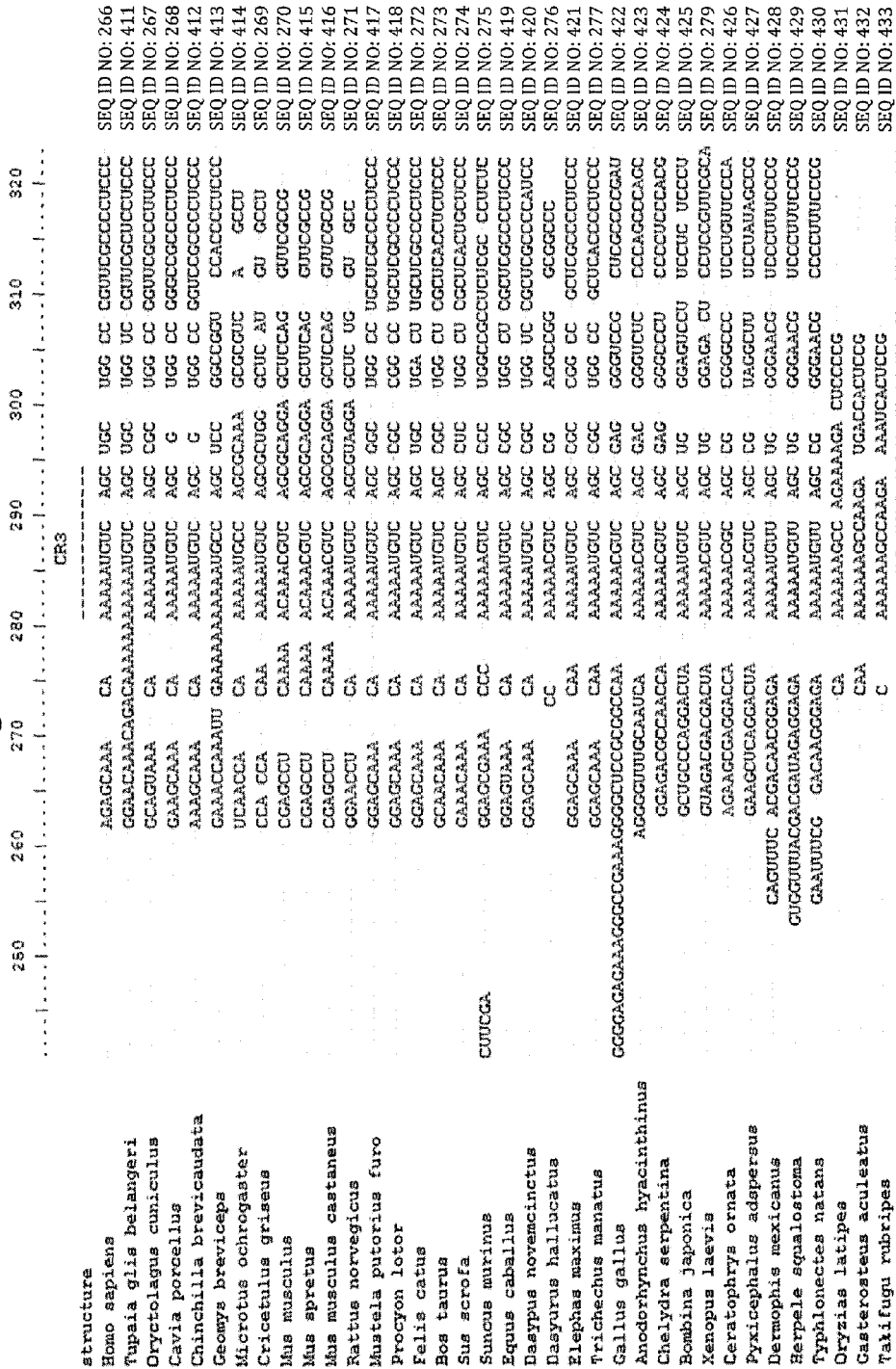
FIG. 7 shows an alignment of a portion of the telomerase RNA from vertebrates showing part of the pseudoknot region of the telomerase RNA. The alignment is taken from the Telomerase Database (telomere.asu.edu: Podlevsky, J D., et al., *Nucleic Acids Research* 36 (database issue):D339-D343 (2008)).

For example, in certain embodiments, modifications to human telomerase RNA are made at one or more of positions 171-191 of SEQ ID NO: 266, which is a region near the pseudoknot of the telomerase RNA. This region is highly conserved among vertebrates, and typically has a sequence of five or more adenosine residues follow by the sequence UGUC or CGUC. An alignment of this region of the telomerase RNA, taken from the Telomerase Database, is shown in FIG. 7. From this alignment, a person of skill in the art would be able to determine which residues in the pseudoknot region may be modified according to the invention. For example, a person of skill in the art would recognized conserved sequences at positions 156-176 of mouse telomerase RNA (SEQ ID NO: 270), at positions 140-170 of rat telomerase RNA (SEQ ID NO: 271), at positions 339-368 of xenopus telomerase RNA (SEQ ID NO: 279), along with other conserved regions.

It is further contemplated that any nucleotide within the target telomerase RNA may be modified using the methods of the present invention, using the structural information that is available in the art. Methods of creating libraries of snoRNA genes for modification at various positions within a target RNA are known in the art (Liu, B., J. Ni, and M. J. Fournier, "Probing RNA in vivo with methylation guide small nucleolar RNAs," Methods, 2001. 23 (3): p. 276-86).

Engineered snoRNAs

The engineered snoRNAs of the invention may be made using methods known in the art, see, e.g., (Liu, B., et al., *Methods* 23(3):276-86 (2001); Huang, C, et al., *Methods Mol. Biol.* 718:227-44 (2011)). In general, standard molecular biology techniques may be used to clone the native snoRNA gene, remove the guide sequence portion of the gene and replace the guide sequence with a guide sequence that targets 2'-O-methylation of a specific nucleotide on the target RNA. The cloned nucleic acids encoding engineered C/D box snoRNA may then be subcloned into vectors for replication of the cloned nucleic acid sequence and/or expression in vivo.

Expression of engineered snoRNAs in vivo may be effected by use of standard techniques known in the art. An engineered snoRNA can be produced in vivo in a mammal, e.g., a human patient, using gene therapy approaches known in the art. These approaches involve administration of a suitable engineered snoRNA encoding nucleic acid operably linked to suitable expression control sequences. Preferably, these sequences are incorporated into a viral vector. Suitable viral vectors for such in vivo expression include, e.g., adenoviral vectors, lentiviral vectors, baculoviral vectors, Epstein Barr viral vectors, papovaviral vectors, vaccinia viral vectors, herpes simplex viral vectors, and adeno associated virus (AAV) vectors. The viral vector can be a replication-defective viral vector. A preferred adenoviral vector has a deletion in its E1 gene or E3 gene. When an adenoviral vector is used, preferably, the mammal is not exposed to a nucleic acid encoding a selectable marker gene.

Expression of engineered snoRNAs in cell lines in vivo may also be performed using transformation, or injection methods known in the art for the cell line being used. See, for example, Huang, C, et al., *Methods Mol. Biol.* 718:227-44 (2011); 718:227-44 and Ge, J., et al., *Rna* 16:1078-1085 (2010). The nucleic acid sequences encoding the engineered snoRNAs may be cloned into vectors for expression in cells in the same manner as nucleic acid sequences encoding for proteins.

In certain embodiments, engineered snoRNAs are provided that direct 2'-O-methylation of nucleotides in or near the pseudoknot region of human telomerase RNA (SEQ ID NO: 266), positions 171-186 as highlighted:

```
  1 GGGUUGCGGA GGGUGGGCCU GGGAGGGGUG GUGGCCAUUU UUUGUCUAAC CCUAACUGAG

61 AAGGGCGUAG GCGCCGUGCU UUUGCUCCCC GCGCGCUGUU UUUCUCGCUG ACUUUCAGCG

121 GGCGGAAAAG CCUCGGCCUG CCGCCUUCCA CCGUUCAUUC UAGAGCAAAC AAAAAAUGUC

181 AGCUGCUGGC CCGUUCGCCC CUCCCGGGGA CCUGCGGCGG GUCGCCUGCC CAGCCCCCGA

241 ACCCCGCCUG GAGGCCGCGG UCGCCCGGG GCUUCUCCGG AGGCACCCAC UGCCACCGCG

301 AAGAGUUGGG CUCUGUCAGC CGCGGGUCUC UCGGGGGCGA GGGCGAGGUU CAGGCCUUUC
```

```
361 AGGCCGCAGG AAGAGGAACG GAGCGAGUCC CCGCGCGCGG CGCGAUUCCC UGAGCUGUGG

421 GACGUGCACC CAGGACUCGG CUCACACAUG C
```

Examples of nucleic acids encoding guide sequences upstream from the D box in a C/D box snoRNA (represented as the highlighted DNA sequence encoding the snoRNA) are shown below, with N representing any nucleotide. The guide sequences are engineered to modify the base complementary to the base shown in bold by their location upstream from Box D of the snoRNA. Guide sequences with and without the Box D sequence are shown for modification of each position below.

Guide Sequences and Box D Sequences:

```
                                            (SEQ ID NO: 285)
Position 171-ACATTTTTTGTTNCTGA (SEQ ID NO: 286)
Position 172-GACATTTTTTGTNCTGA (SEQ ID NO: 287)
Position 173-TGACATTTTTTGNCTGA (SEQ ID NO: 288)
Position 174-CTGACATTTTTTNCTGA (SEQ ID NO: 289)
Position 175-GCTGACATTTTTNCTGA (SEQ ID NO: 290)
Position 176-AGCTGACATTTTNCTGA (SEQ ID NO: 291)
Position 177-CAGCTGACATTTNCTGA (SEQ ID NO: 292)
Position 178-GCAGCTGACATTNCTGA (SEQ ID NO: 293)
Position 179-TGCAGCTGACATNCTGA (SEQ ID NO: 294)
Position 180-CTGCAGCTGACANCTGA (SEQ ID NO: 295)
Position 181-CCTGCAGCTGACNCTGA (SEQ ID NO: 296)
Position 182-GCCTGCAGCTGANCTGA (SEQ ID NO: 297)
Position 183-GGCCTGCAGCTGNCTGA (SEQ ID NO: 298)
Position 184-GGGCCTGCAGCTNCTGA (SEQ ID NO: 299)
Position 185-CGGGCCTGCAGCNCTGA
```

Guide Sequences Only:

```
                                            (SEQ ID NO: 300)
Position 171-ACATTTTTTGTT (SEQ ID NO: 301)
Position 172-GACATTTTTTGT (SEQ ID NO: 302)
Position 173-TGACATTTTTTG (SEQ ID NO: 303)
Position 174-CTGACATTTTTT (SEQ ID NO: 304)
Position 175-GCTGACATTTTT (SEQ ID NO: 305)
Position 176-AGCTGACATTTT (SEQ ID NO: 306)
Position 177-CAGCTGACATTT (SEQ ID NO: 307)
Position 178-GCAGCTGACATT (SEQ ID NO: 308)
Position 179-TGCAGCTGACAT (SEQ ID NO: 309)
Position 180-CTGCAGCTGACA (SEQ ID NO: 310)
Position 181-CCTGCAGCTGAC (SEQ ID NO: 311)
Position 182-GCCTGCAGCTGA (SEQ ID NO: 312)
Position 183-GGCCTGCAGCTG (SEQ ID NO: 313)
Position 184-GGGCCTGCAGCT (SEQ ID NO: 314)
Position 185-CGGGCCTGCAGC
```

The guide sequences provided above may be used to modify any of the C/D snoRNA sequences to form an engineered snoRNA. The C/D box snoRNA only needs to be modified to position the guide sequence relative to the D box sequence as shown.

As an example of how C/D box snoRNAs may be modified according to the invention, the following nucleic acids encoding engineered snoRNA molecules are shown for illustrative purposes. The D box sequence and guide sequence are underlined. The base complementary to the nucleotide to be modified is shown in bold type.

SNORD73a native sequence (with an AUGA D' box sequence):

```
                                            (SEQ ID NO: 74)
AATAAGTGATGAAAAAAGTTTCGGTCCCAGATGATGGCCAGTGATAAC

AACATTTTTCTGATGTT.
```

SNORD73a sequence engineered for modification of human telomerase at position 176:

```
                                            (SEQ ID NO: 315)
AATAAGTGATGAAAAAAAGCTGACATTTTGATGATGGCCAGTGATAAC

AACATTTTTCTGATGTT.
```

SNORD73a sequence engineered for modification of human telomerase at position 181:

```
                                            (SEQ ID NO: 316)
AATAAGTGATGAAAAACCTGCAGCTGACGATGATGGCCAGTGATAA

CAACATTTTTCTGATGTT.
```

SNORD111A native sequence (with a CUGA D' box sequence):

(SEQ ID NO: 120)
CAGCCTGAAATGATGACTCTTTAAAAAATT<u>TCATGTCTCTTCTCTGA</u>CA

TTTTTCTCTGGACACAGTTTTTGCCTTATGAATCTGATCAGGCTG.

SNORD111A sequence engineered for modification of human telomerase at position 176:

(SEQ ID NO: 317)
CAGCCTGAAATGATGACTCTTTAAAAAATT<u>AGCTGACATTTTCTGAC</u>

ATTTTTCTCTGGACACAGTTTTTGCCTTATGAATCTGATCAGGCTG.

SNORD111A sequence engineered for modification of human telomerase at position 181:

(SEQ ID NO: 318)
CAGCCTGAAATGATGACTCTTTAAAAAATT<u>CCTGCAGCTGACTCTGAC</u>

ATTTTTCTCTGGACACAGTTTTTGCCTTATGAATCTGATCAGGCTG.

SNORD113-1 native sequence (with a CUGA D' box sequence):

(SEQ ID NO: 123)
AAAGTGAGTGATGAATAGTTCTGTGGCATATGAATCATTAATTTTGAT<u>T</u>

<u>AAACCCTAAACTCTGA</u>AGTCC.

SNORD113-1 sequence engineered for modification of human telomerase at position 176:

(SEQ ID NO: 319)
AAAGTGAGTGATGAATAGTTCTGTGGCATATGAATCATTAATTTTGAT

<u>AGCTGACATTTTCTGA</u>AGTCC.

SNORD113-1 sequence engineered for modification of human telomerase at position 181:

(SEQ ID NO: 320)
AAAGTGAGTGATGAATAGTTCTGTGGCATATGAATCATTAATTTTGAT

<u>CCTGCAGCTGACTCTGA</u>AGTCC.

Examples of C/D box snoRNAs include those modified from the yeast snR52 wild type sequence to target specific nucleotides within a pseudoknot of the telomerase RNA, shown below. The base complementary to the nucleotide to be modified is shown in bold type.

Native snR52 sequence (with CTGA D Box sequence):

(SEQ ID NO: 236)
TACTATGATGAATGACATTA<u>GCGTGAAC A ATCTCTGA</u>TACAAAATCGAA

AGATTTTAGGATTAGAAAAACTTATGTTGCCTTCCTTCTGAAA.

Guide sequence targeting position 804 of yeast telomerase (TLC1):

(SEQ ID NO: 321)
<u>AATAGATTT T TTTNCTGA</u>.

Guide sequence targeting position 805 of yeast telomerase (TLC1):

(SEQ ID NO: 322)
<u>GAATAGATT T TTTNCTGA</u>.

Guide sequence targeting position 806 of yeast telomerase (TLC1):

(SEQ ID NO: 323)
<u>TGAATAGA T TTTNCTGA</u>.

Guide sequence targeting position 809 of yeast telomerase (TLC1):

(SEQ ID NO: 324)
<u>CAGTGAAT A GATNCTGA</u>.

Guide sequence targeting position 810 of yeast telomerase (TLC1):

(SEQ ID NO: 325)
<u>TCAGTGAA T AGANCTGA</u>.

Guide sequence targeting position 811 of yeast telomerase (TLC1):

(SEQ ID NO: 326)
<u>TTCAGTGA A TAGNCTGA</u>.

As should be apparent from the above illustrative examples, a guide sequence of an engineered snoRNA is designed to base pair with the target telomerase so that the nucleotide to be modified is complementary to the base 5 bases upstream from the D or D' box of the snoRNA. The guide sequences of the present invention can be used in any engineered snoRNA according to this rule.

It is contemplated that the guide RNA sequences may be longer or shorter than the and 12 nucleotide guide sequences illustrated above. The guide sequences may be 6, 7, 8, 9, 10, 11, 12, 13, 14, 15, 16, 17, 18, 19, 20, 25, 30 or greater nucleotides in length. A person of skill in the art will understand that it is possible to lengthen the guide sequence by adding complementary nucleotides to the 5' end of the guide sequence based on the complementary sequence of the target RNA so that the base to be modified remains base paired with the Box D+5 position. A person of skill in the art will also understand that it is possible to shorten the guide sequence by removing complementary nucleotides from the 5' end of the guide sequence so that the base to be modified remains base paired with the Box D+5 position. It is further contemplated that the guide sequences may have 1, 2, 3, 4, 5, 6, 7, 8 or more mismatched base pairing with the target RNA, depending on the length of the guide sequence.

After an engineered C/D box snoRNA is expressed in a cell, telomerase complexes containing modified telomerase RNA may be recovered from the cell using methods known in the art or using methods as described in the examples below (Qiao, F., et al., *Nat. Struct. Mol. Biol.* 15:634-40 (2008)). It is further contemplated that C/D snoRNA modification of the target telomerase RNA may be effected in vitro by reconstitution of the necessary components of the snoRNA modification machinery, including any snoRNA associated proteins.

Isolated telomerase complexes may be assayed in vitro as is known in the art to determine the effects of modifications. Examples of telomerase assays may be found in Zappulla, D. C., et al., (*Proc. Natl. Acad. Sci. USA* 101:10024-9 (2004)) and Chen, J. L. and Greider C. W. (*Proc. Natl. Acad. Sci. USA*

102:8080-8085 (2005)). In vitro assays comparing modified telomerase with wild type telomerase activity may be used to determine whether the 2'-O-methylation effected by the engineered snoRNA causes an increase or decrease in telomerase activity.

The in vivo activity of modified telomerase with a modified telomerase RNA may be measured by determining the average length of telomeres in cells containing the engineered snoRNA as compared to the average length of telomeres in cells with unmodified telomerase RNA. Methods for determining telomere length are known in the art, including, e.g., PCR methods, southern blot methods and fluorescent in situ hybridization methods (Allshire R. C. et al., (1989) *Nucleic Acids Res.* 17:4611-4627 (1989); Rufer, N. et al., *Nat. Biotechnol.* 16: 743-747 (1998); Cawthon, R. M., *Nucleic Acids Res.* 30 (10):e47)(2002)). The presence of longer telomeres in cells having modified telomerase RNA suggests an increase in telomerase activity from the modification while the presence of shorter telomeres in cells having modified telomerase RNA suggests an decrease in telomerase activity from the modification.

Modified telomere RNA may be isolated from cells using methods known in the art. Primer extension methods known in the art may be used to determine whether or not the targeted position of the telomere RNA was 2'-O-methylated (Ge, J., et al., *Rna* 16:1078-1085 (2010)).

Having now generally described the invention, the same will be more readily understood through reference to the following examples which are provided by way of illustration, and are not intended to be limiting of the present invention, unless specified.

EXAMPLES

Results
Artificial Box C/D RNA Targeting TLC1 is Efficiently Expressed

Qiao, et al, have recently shown that 2'-OH groups of the triple-helix (A804, A805 and A806) nucleotides and their adjacent nucleotides (U809, A810 and U811) within the conserved pseudoknot structure of TLC1 contribute to telomerase function in vitro ((Qiao, F., et al., *Nat. Struct. Mol. Biol.* 15:634-40 (2008)), (FIG. 1A), thus offering an opportunity for an in vivo functional analysis of these 2'-OH groups using RNA-guided RNA 2'-O-methylation. Six artificial box C/D guide RNAs were designed (gRNA-A804, gRNA-A805, gRNA-A806, gRNA-U809, gRNA-A810, gRNA-U811), each of which targeted one of the six nucleotides in the triple-helix region (FIG. 1A). These artificial guide RNAs were constructed based on snR52, a naturally occurring *S. cerevisiae* box C/D snoRNA that contains two guide sequences, one between box C and box D' and the other between box C' and box D (FIG. 1B). The short guide sequence between box C and box D' or between box C' and box D was altered to target the TLC1 nucleotides; all other nucleotide sequences of snR52 were left unchanged. The artificial box C/D RNA genes were separately inserted into a 2µ vector, with the expression of the box C/D guide RNAs under the control of the GPD promoter.

Figure 2B:
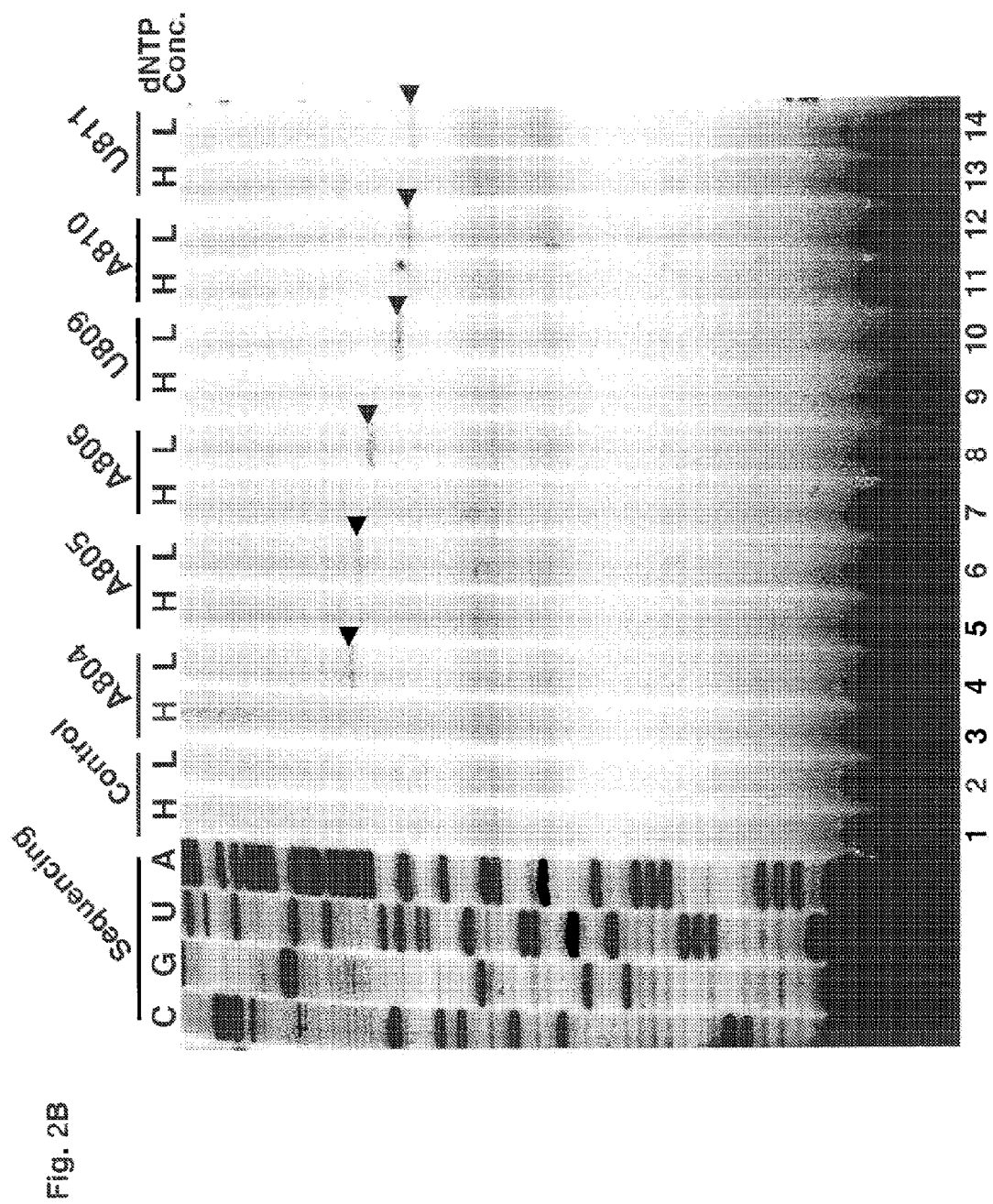

Upon transformation, the expression of guide RNA was measured using northern analysis. Northern results showed that every guide RNA was efficiently expressed (FIG. 2A, lanes 3-8).
Artificial Box C/D Guide RNA is Functionally Active In Vivo To ensure that the artificial box C/D guide RNA had a sufficient level of activity, a primer extension-based 2'-O-methylation assay to detect 2'-O-methylation of TLC1 at the target sites was carried out. It is well established that at low dNTP concentrations, primer extension will stop/pause precisely one nucleotide before the 2'-O-methylated site (Maden, B. E., et al., *Biochimie* 77:22-9 (1995)). When a guide RNA was expressed, a stop/pause signal corresponding to its target site was clearly detected under low-dNTP conditions (FIG. 2B, lanes 4, 6, 8, 10, 12 and 14). As expected, when high dNTP concentrations were used, the stop/pause signal was barely detected (FIG. 2B, lanes 3, 5, 7, 9, 11 and 13). Thus, these results demonstrated that each guide RNA was capable of guiding TLC1 2'-O-methylation at its target site.

Given that 2'-O-methylation efficiency is important for determining the degree to which the modification influences telomerase activity, the level of 2'-O-methylation at each target site was further quantified. A recently developed ligation based assay was used, in which a pair of DNA primers are aligned with the RNA substrate upon hybridization, leaving the ligation junction (nick) 5' or 3' of the test nucleotide in the RNA substrate (Saikia, M., et al., *Rna* 12:2025-33 (2006)) (FIG. 2C). If the test nucleotide is 2'-O-methylated, the two primers will not be ligated if the ligation junction is placed 3' of the modified nucleotide (discriminating or D primer pair), but they will be quantitatively ligated if the junction is placed 5' of the modified nucleotide (non-discriminating or ND primer pair). If the test nucleotide is not 2'-O-methylated, the two primers (either D or ND primer pair) will be quantitatively ligated regardless of where the junction is (FIG. 2C). The ligation efficiency should correlate well with the modification level at the test site. Comparison of the ligation ratios will thus allow quantification of 2'-O-methylation at the test nucleotide.

Figure 2D:
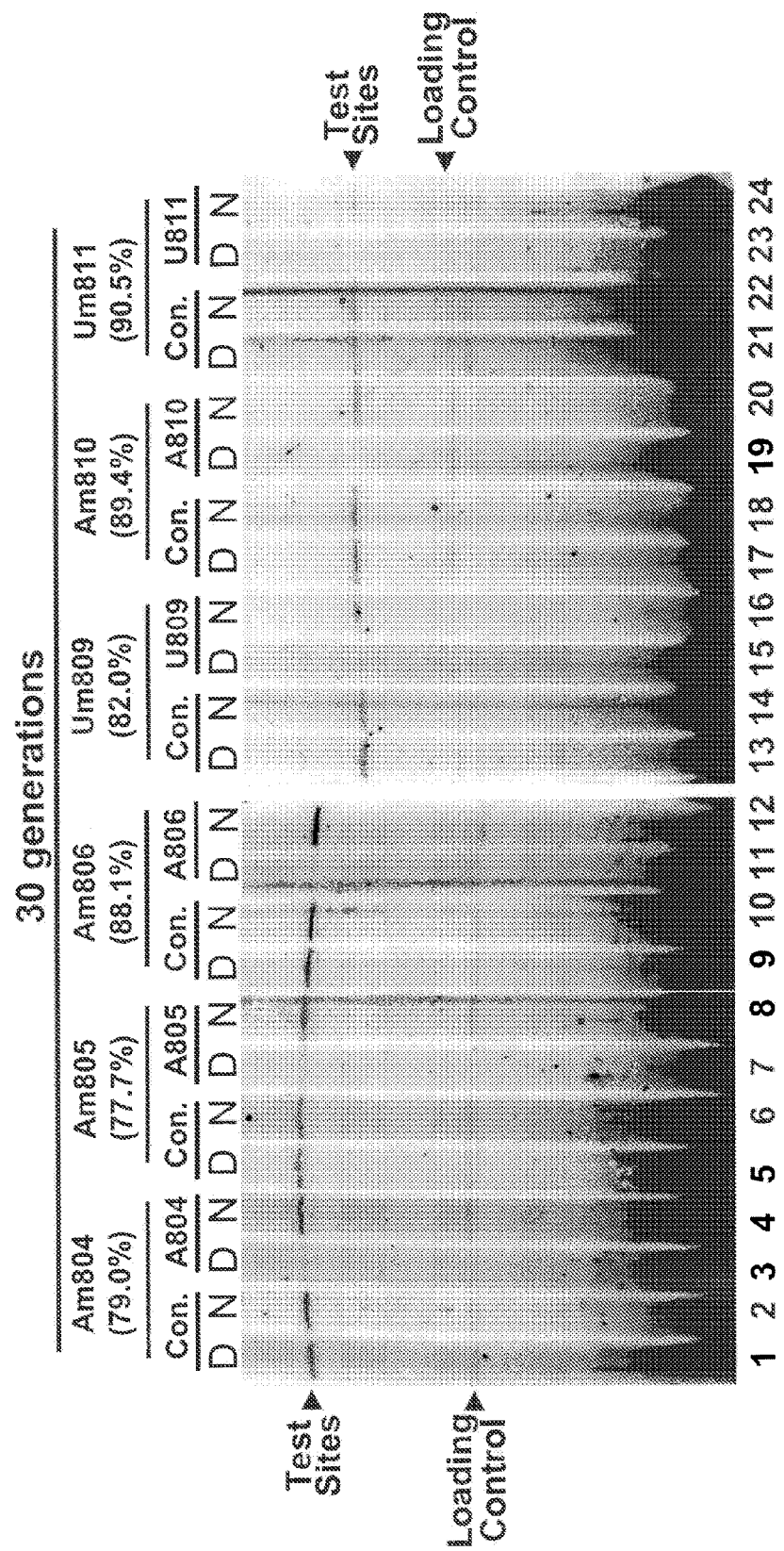
Figure 2E:
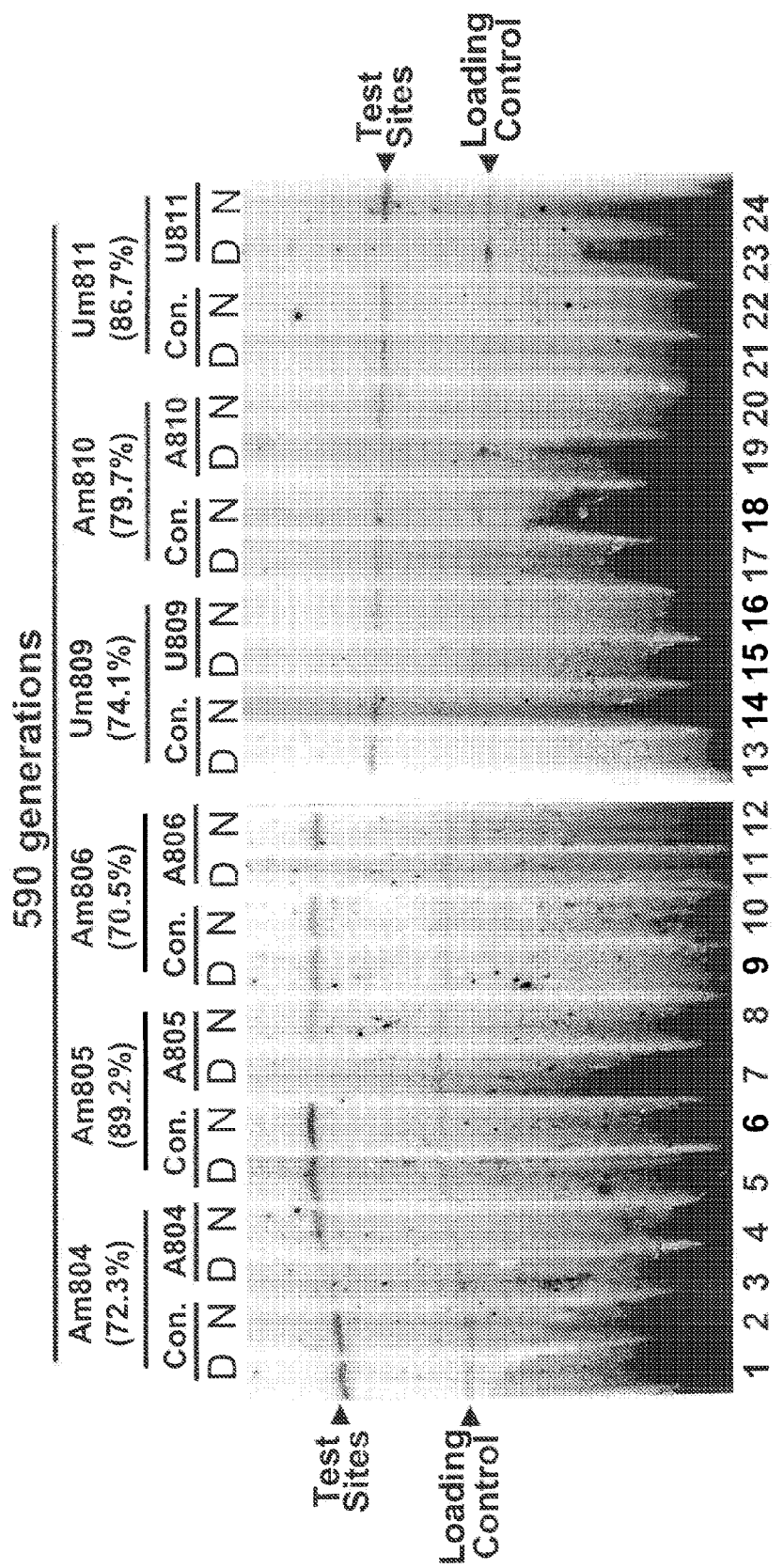
Figure 3A:
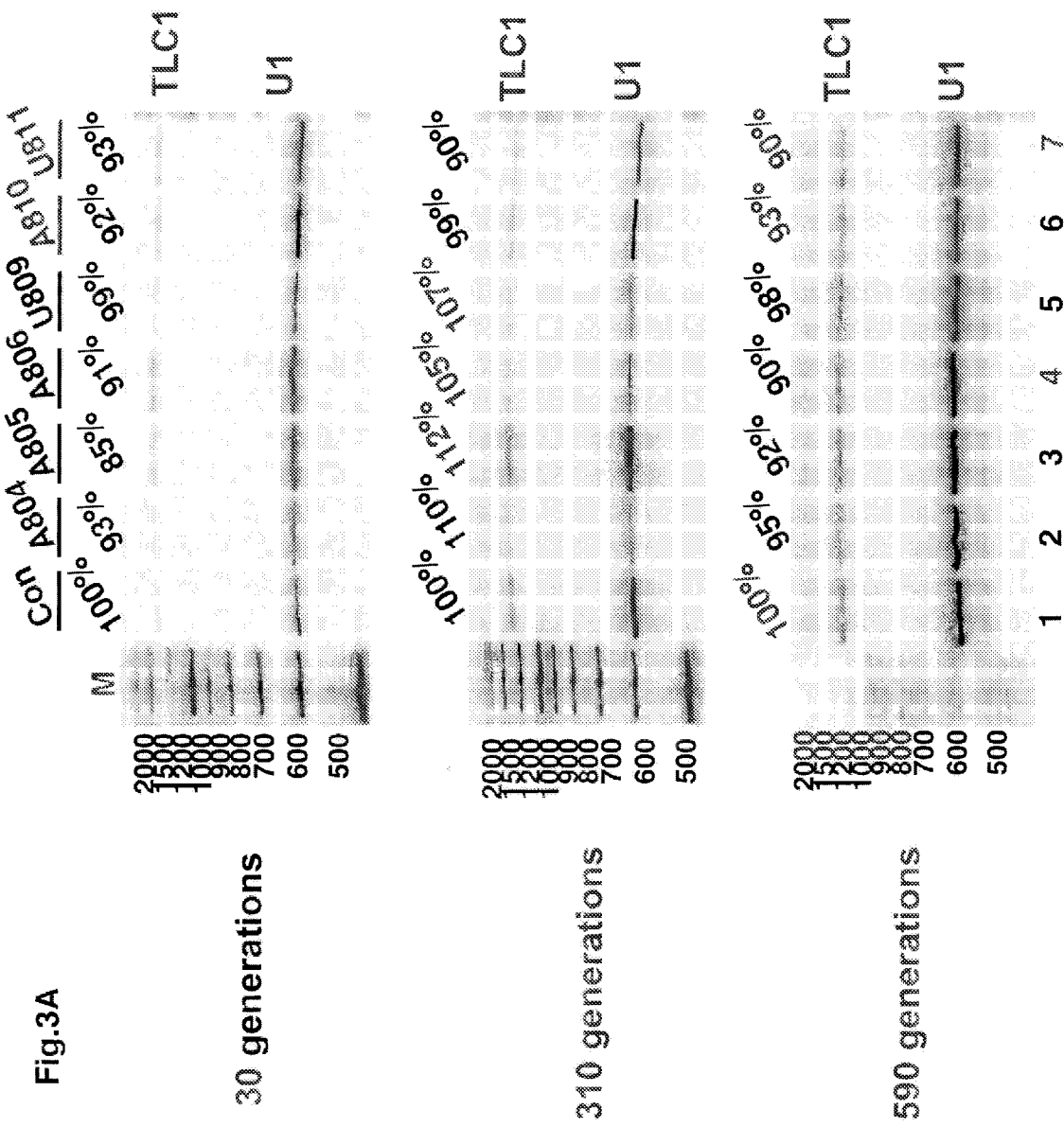
FIG. 3 shows experimental results demonstrating that 2%0-methylated TLC1 RNA is incorporated into telomerase RNP. (A) 2'-Omethylation has no effect on the steady-state level of TLC1 RNA. Cells expressing a random gRNA (control; lane 1), gRNA-A804 (lane 2), gRNA-A805 (lane 3), gRNA-A806 (lane 4), gRNA-U809 (lane 5), gRNA-A810 (lane 6) or gRNA-U811 (lane 7), were grown for 30 generations (top panel), 310 generations (middle panel), and 590 generations (bottom panel). RNAs were isolated from these cells and analyzed by northern blotting with TLC1-specific and U1-specific probes. TLC1 RNA levels were calculated relative to U1 (in percentage). (B) Incorporation of TLC1 RNA into telomerase RNP. Extracts prepared from cells expressing a random gRNA (control; top panel) or gRNA-U809 were loaded on a 15-40% glycerol gradient. Nineteen fractions were collected. RNA from each fraction was analyzed by northern blotting with TLC1-specific and U1-specific probes. On the right is a plot showing the TLC1 and U1 signal peaks. (C) Fractions 12-15 of the gradient described in (B) were pooled, RNAs were recovered, and primer extension was carried out in the presence of high (H; lanes 1 and 3) or low (L; lanes 2 and 4) dNTP concentrations. Lanes 1 and 2 are from cells expressing a random gRNA (control), and lanes 3 and 4 are from cells expressing gRNA-U809. A TLC1 sequencing ladder was electrophoresed in parallel on the left. A signal corresponding to 2%0-methylated U809 is indicated. (D) Western and northern analyses of immunoprecipitated Est2p complex. A yeast strain, in which EST2 gene is fused with a protein A tag, was transformed with a plasmid containing no gRNA (lane 8), a random (control) gRNA (lane 1), gRNA-A804 (lane 2), gRNA-A805 (lane 3), gRNA-A806 (lane 4), gRNA-U809 (lane 5), gRNA-A810 (lane 6) or gRNA-U811 (lane 7). IgG precipitation was subsequently carried out. As a control, an untagged yeast strain was also used for IgG precipitation (lane 9). Precipitated proteins were recovered, and western analysis (with anti-protein A antibodies) performed. Furthermore, RNA co-precipitated with protein A-Est2p was recovered, and northern analysis carried out. Probes for U1 (loading control) and TLC1 were used, and signals corresponding to these RNAs are indicated. As a control, total cellular RNA was also used (lane 10). (E) 2'-O-methylation mapping was conducted as in (C). All seven samples [corresponding to lanes 1-7 in (D)] were assayed.

FIGS. 2D and 2E show the ligation experiments using TLC1 RNA harvested after 30 and 590 generations, respectively. When the ND primer pair was used, ligation efficiency (the ratio of the ligated product to the loading control) was about the same for all TLC1 RNAs at all sites tested, including untargeted TLC1 RNA (con.) and gRNA targeted TLC1 RNA (FIGS. 2D and 2E, compare even-numbered lanes). However, when the D primer pair was used, a drastic reduction in ligation was observed in reactions where TLC1 RNA was isolated from cells expressing gRNAs (FIGS. 2D and 2E, compare lades 3, 7, 11, 15, 19 and 23 with other odd-numbered lanes). These results indicated a high level (70-90%) of 2'-O-methylation at all target sites regardless of the number of cell generations (30 or 590 generations) (compare FIG. 2D with FIG. 2E, and compare targeted lanes with untargeted control lanes). These results also indicated that 2'-Omethylation was target specific, as reduced ligation was detected only in reactions where a target-specific gRNA was expressed and a D primer pair for the respective target site was used (FIG. 2D, FIG. 2E, and data not shown).
2'-O-Methylation in the Triple-Helix Region does not Change TLC1 RNA Levels Whether 2'-O-methylation in the triple-helix region would affect TLC1 RNA levels was then tested. Using northern analysis, the levels of TLC1 RNA in wild-type control cells and in cells expressing various artificial gRNAs were assessed. Total RNAs were isolated from these cells after different numbers of generations, and northern analysis was carried out using a TLC1-specific probe and a U1-specific probe as an internal control. The signals of TLC1 RNA relative to U1 RNA were virtually identical in all the cells after 30, 310 and 590 generations (FIG. 3A), indicating that targeted 2'-Omethylation had no effect on steady-state levels of TLC1 RNA.

2'-O-Methylated TLC1 RNA is Assembled into Telomerase RNP

Figure 3B:
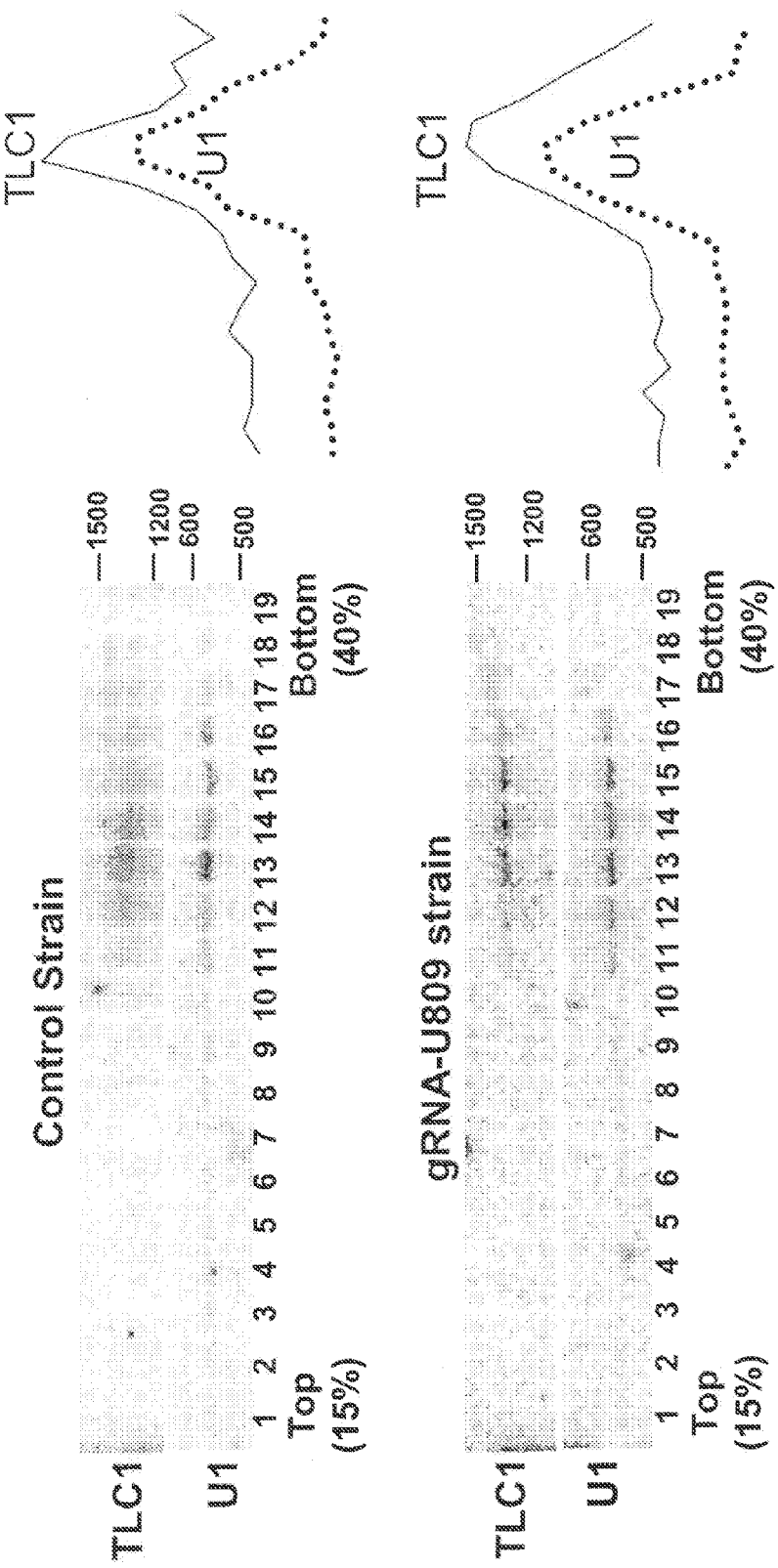
Figure 3C:
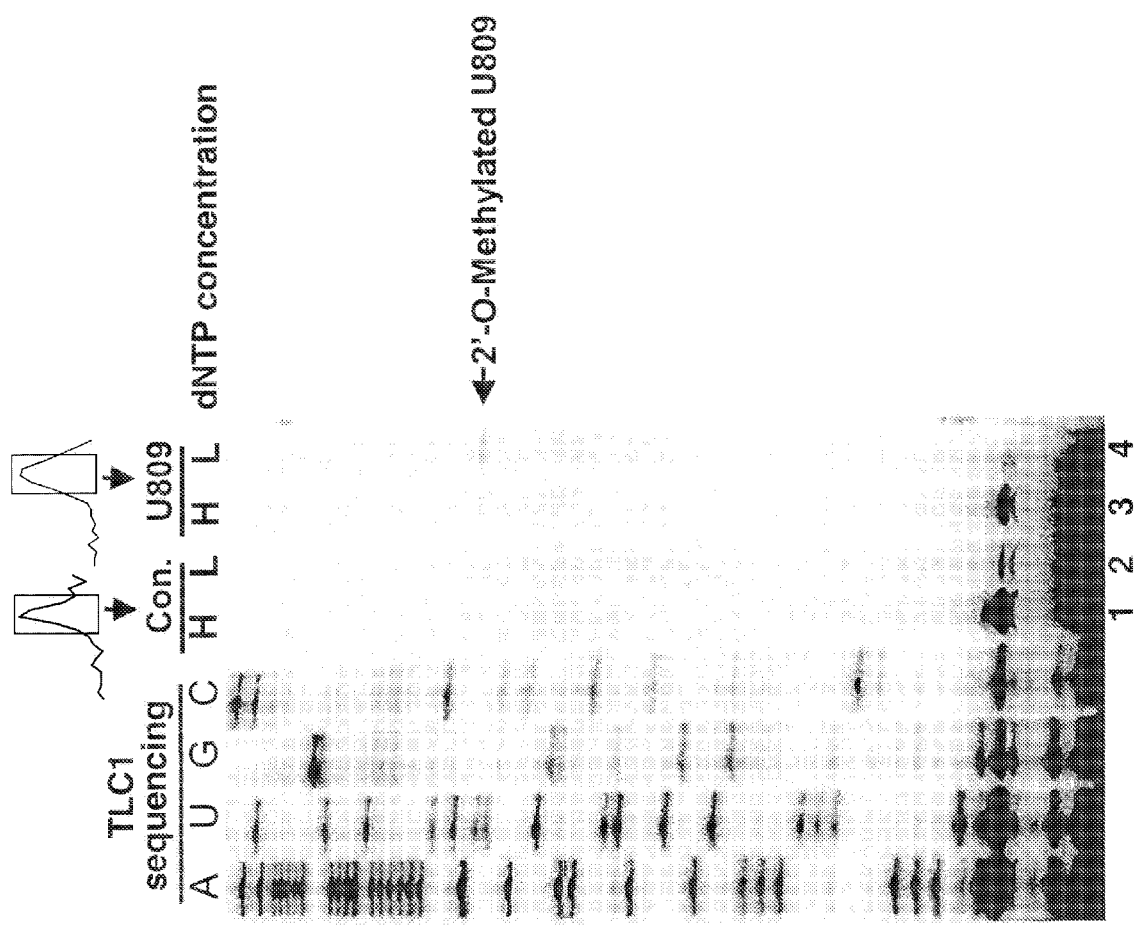

To determine whether 2'-O-methylated TLC1 RNA was incorporated into telomerase RNP, a glycerol gradient analysis was carried out. TLC1 RNA from either the control strain or the strain expressing gRNA-U809 peaked in the same fractions, just as U1 snRNP did in both strains (FIG. 3B). The RNA from the telomerase RNP peaks was then isolated and the 2'-O-methylation assay was performed. Although no 2'-O-methylation signal was observed in control TLC1, RNA (FIG. 3C; lanes 1 and 2), a clear 2'-Omethylation signal corresponding to U809 was detected in TLC1 RNA isolated from cells expressing gRNA-U809 (lanes 3 and 4). Thus, 2'-O-methylated TLC1 RNA appeared to be incorporated into the telomerase RNP.

To further confirm these gradient results, an independent approach was performed, namely Est2p-co-precipitation assay. A strain in which the telomerase reverse transcriptase gene EST2 is fused with a protein A tag (Friedman, K. L., et al., *Genes Dev.* 13:2863-74 (1999)) was used in this approach.

Figure 3D:
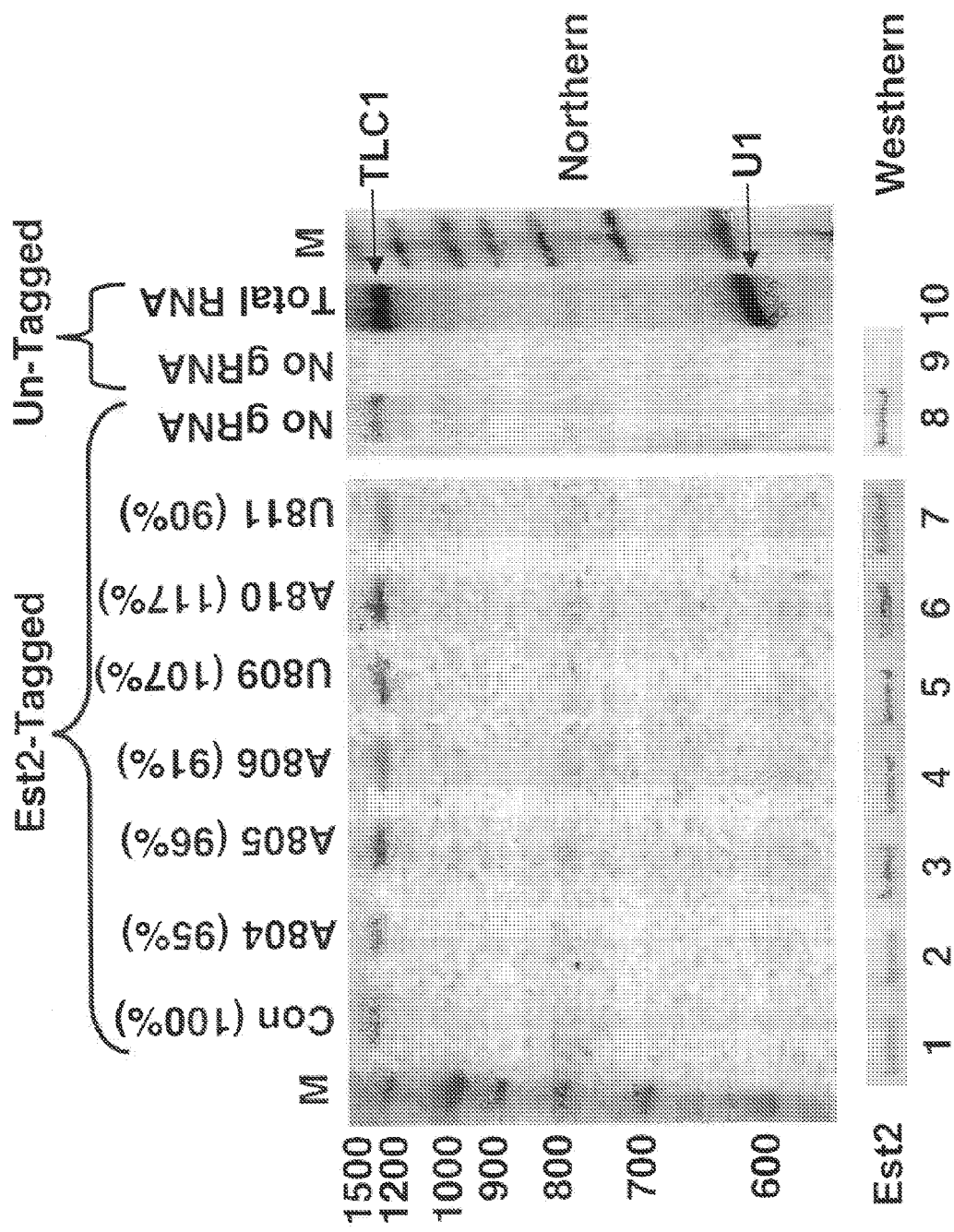
Figure 3E:
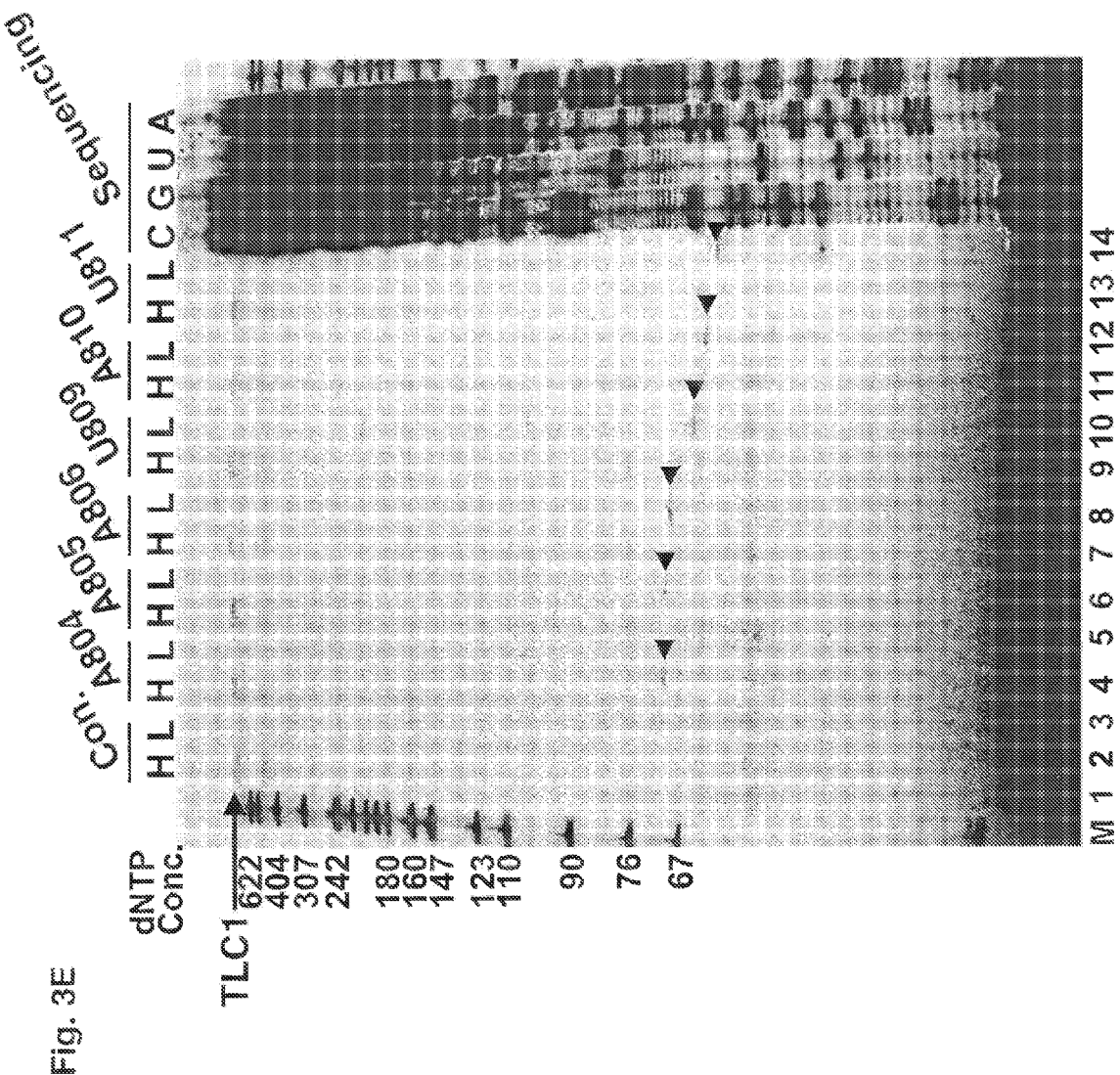

Upon transformation with the plasmid containing an artificial box C/D RNA gene, cells were harvested, and Est2p was pulled down through protein A-IgG precipitation. Western blotting was used to measure the precipitated Est2p. As shown in FIG. 3D, a nearly identical amount of Est2p was precipitated [compare the intensity of the Est2 band in lanes 1-8 (Est2-tagged lanes)]. As a control, when untagged strain was used, an Est2p was detected (lane 9). RNA co-precipitated with Est2p was also recovered and analyzed. Northern blotting indicated that TLC1 RNA was efficiently co-precipitated with Est2p regardless of whether cells were transformed with a plasmid containing no gRNA gene (lane 8), a random box C/D RNA gene (lane 1; control) or any one of the six artificial box C/D RNA genes (lanes 2-7). 2'-O-methylation was further assayed, and these experiments showed that Est2p-associated TLC1 RNA, isolated from cells expressing a gRNA, was efficiently 2'-O-methylated at the expected target site (FIG. 3E). Thus, it appears that 2'-O-methylated TLC1 RNA is efficiently incorporated into telomerase RNP (at least associated with Est2p).

Figure 4A:
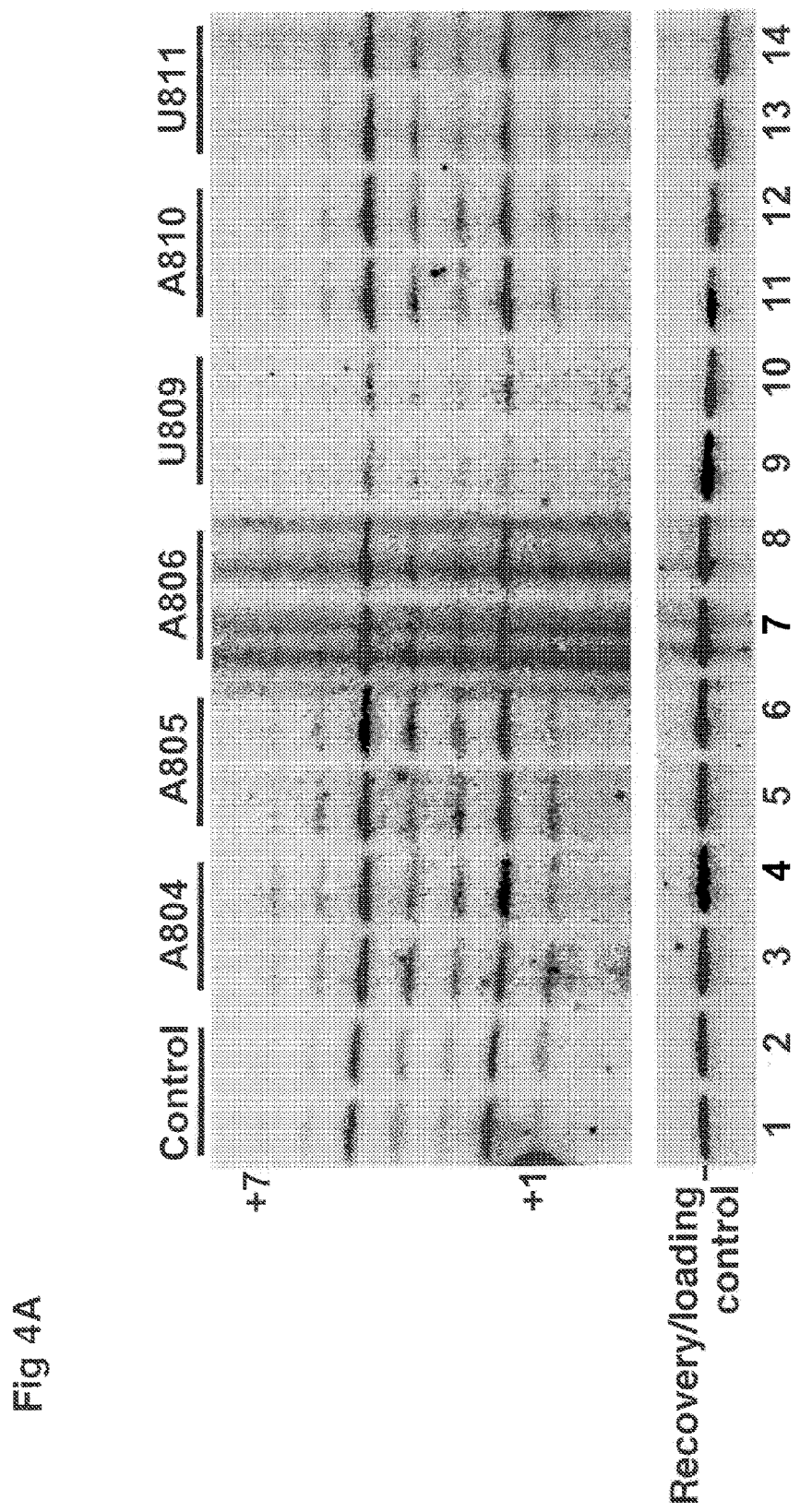
FIG. 4 shows the experimental results demonstrating of an in vitro telomerase activity assay. (A) IgG-bound (protein A-Est2p) fraction described in FIG. 3D was used directly for in vitro telomerase activity assay (Seto, A. G., et al., *Rna* 9:1323-32 (2003)). Three independent sets of experiments, each in duplicate, were carried out. Shown is one such experiment. Duplicate lanes represent two independent reactions for each strain. A control band [for recovery and loading control (Seto, A. G., et al., *Nature* 401:177-80 (1999))] is also shown. (B) Relative telomerase activity of the IgG-bound fraction, derived from each strain, was quantified based on three independent sets of duplicate experiments. The quantification was performed by comparing the intensity of the bands (the sum of all seven bands) in each lane. Adjustment was made for every band by deducting a background area immediately above the band. Percentage of in vitro telomerase activity of each strain was calculated against control activity (set to 100%). The error bars represent the standard deviation of the measurements. Asterisks (*) indicate that the P-values are less than 0.05 (calculated using the Microsoft Exel t-test software).

In Vitro Functional Assay Indicates that 2'-O-Methylation at U809 (Adjacent to the Triple-Helix) Reduces Telomerase Activity To assess whether 2'-O-methylation at the nucleotides in and near the triple-helix structure affects function, the in vitro telomerase activity assay was carried out (Friedman, K. L., et al., *Genes Dev.* 13:2863-74 (1999)) using the Est2p-bound fractions described above. As shown in FIG. 4, targeted 2'-Omethylation at position U809 resulted in a substantial reduction of telomerase activity (FIG. 4A, lanes 9 and 10; FIG. 4B). When A804 or A805 was targeted by the artificial gRNAs, a relatively small but statistically significant enhancement of telomerase activity was observed (FIG. 4A, compare lanes 3-6 with lanes 1 and 2; FIG. 4B). 2'-O-methylation at the other sites had no significant effect on telomerase activity (FIGS. 4A and 4B).

A804 and A805 are in the triple-helix structure, and U809 is in a nearby stem adjacent to the triple-helix (FIG. 1A). The fact that 2'-O-methylation at U809 reduced telomerase activity is consistent with the previous in vitro study by Qiao, et al., who showed that combined substitution of the 2'-OH groups of all three adjacent nucleotides (U809, A810 and U811) with 2'-H groups resulted in diminished telomerase activity. In contrast, targeted 2'-O-methylation directed at the triple-helix nucleotide A804 or A805 resulted in no reduction of telomerase activity; rather, a slight increase in telomerase activity was observed. This observation is different from that made by Qiao, et al., who show a substantial reduction of telomerase activity when the 2'-OH groups of all three triple-helix nucleotides are simultaneously changed to 2'-H groups.

This apparent inconsistency may be due to the fact that the 2'-OH groups were changed to 2'-O-methyl groups whereas in the previous study, the 2'-OH groups were changed them to 2'-H groups.

Figure 5:
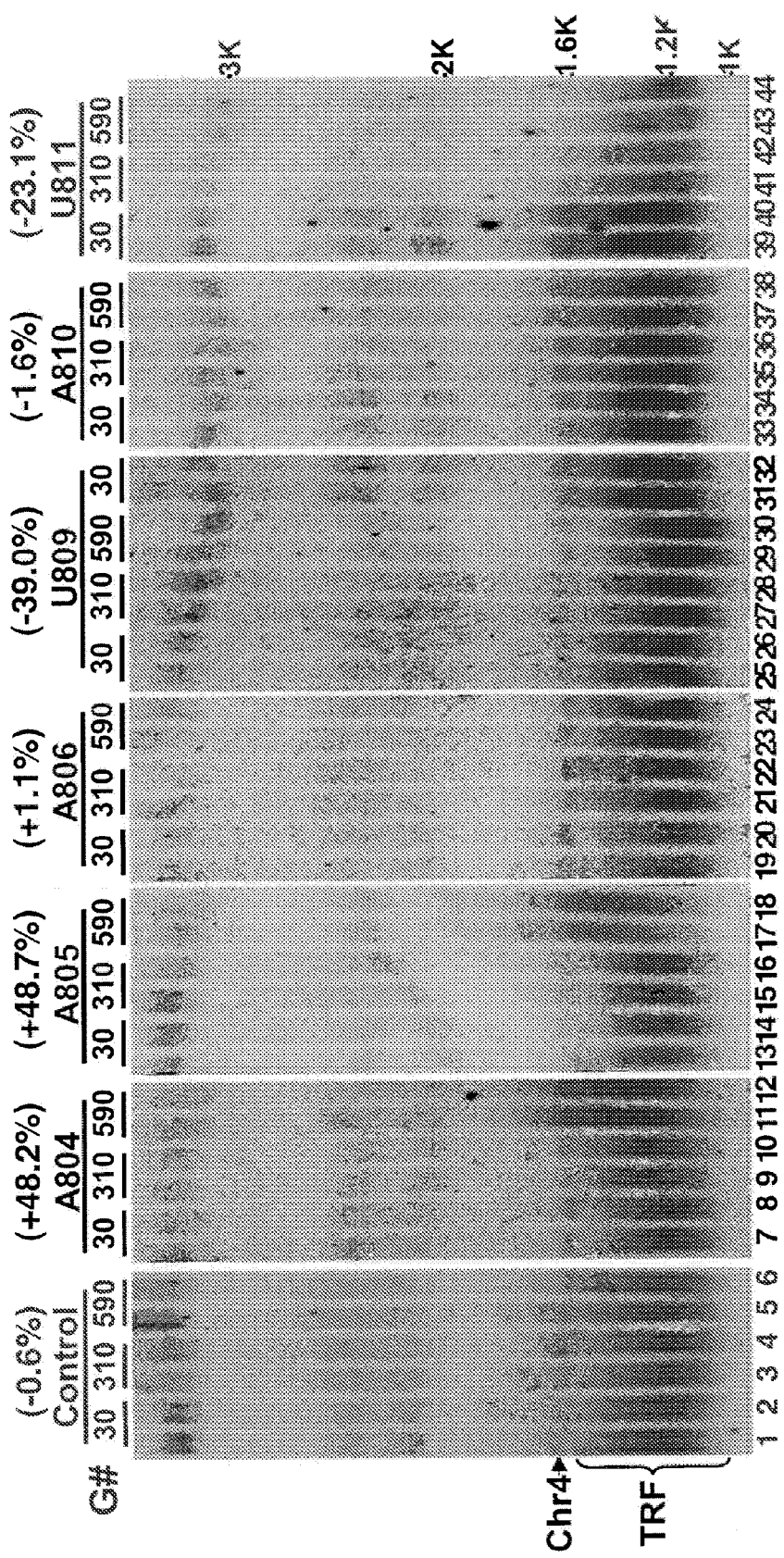
FIG. 5 shows Southern analysis of chromosome end length in cells expressing various artificial guide RNAs. Cells (yCH-002) expressing a random gRNA (control; lanes 1-6); gRNA-A804 (lanes 7-12); gRNA-A805 (lanes 13-18), gRNA-A806 (lanes 19-24), gRNA-U809 (lanes 25-32), gRNA-A810 (lanes 33-38) or gRNA-U811 (lanes 39-44), were harvested after growing for the indicated number of generations (G#). DNA was recovered, digested with XhoI and hybridized with two radiolabeled probes, a telomere-specific one and a chromosome IV-specific one (as an internal control). The fragment of chromosome IV (Chr4) and the telomeres (TRF) are indicated. For each strain, two independent experiments are presented in duplicate lanes. The distances between the signal peaks of Chr4 and TRF were measured using Imagequant software (Molecular Dynamics) (Bachellerie, J. P., et al., *Trends Biochem. Sci.* 20:261-4 (1995)). Shown in parentheses at the top of each strain are the relative changes in distance between two time points (30 and 590 generations) (difference in average distance between the two time points, divided by the average distance at 30 generations). "+" indicates telomere lengthening, and "−" indicates telomere shortening.

A804, A805 and U809 in the Triple-Helix Region are Key 2'-O-methylation Targets for Influencing Telomerase Activity In Vivo The effect of the six artificial guide RNAs on chromosome end maintenance in vivo was then assessed. Using Southern blotting, telomere length in cells expressing these artificial gRNAs was monitored. As shown in FIG. 5, when gRNA-U809 was expressed, chromosome ends progressively shortened with time [compare lanes 29 and 30 (590 generations) with lanes 27 and 28 (310 generations) and with lanes 25 and 26 (30 generations) or lanes 31 and 32 (30 generations)]. Interestingly, the chromosome ends moderately lengthened when gRNA-A804 or gRNA-A805 was expressed (compare lanes 11 and 12 with lanes 9 and 10, and lanes 7 and 8; also compare lanes 17 and 18 with lanes 15 and 16, and lanes 13 and 14). In contrast, no apparent changes in telomere length were detected in cells expressing any other gRNAs (lanes 19-24 and 33-44) or no gRNA (data not shown). These results are consistent with the in vitro assay results described above (also see Discussion below), pinpointing three critical nucleotides: A804 and A805 for lengthening and U809 for shortening. The other sites appeared to be less important for telomerase activity when targeted individually.

Figure 6A:
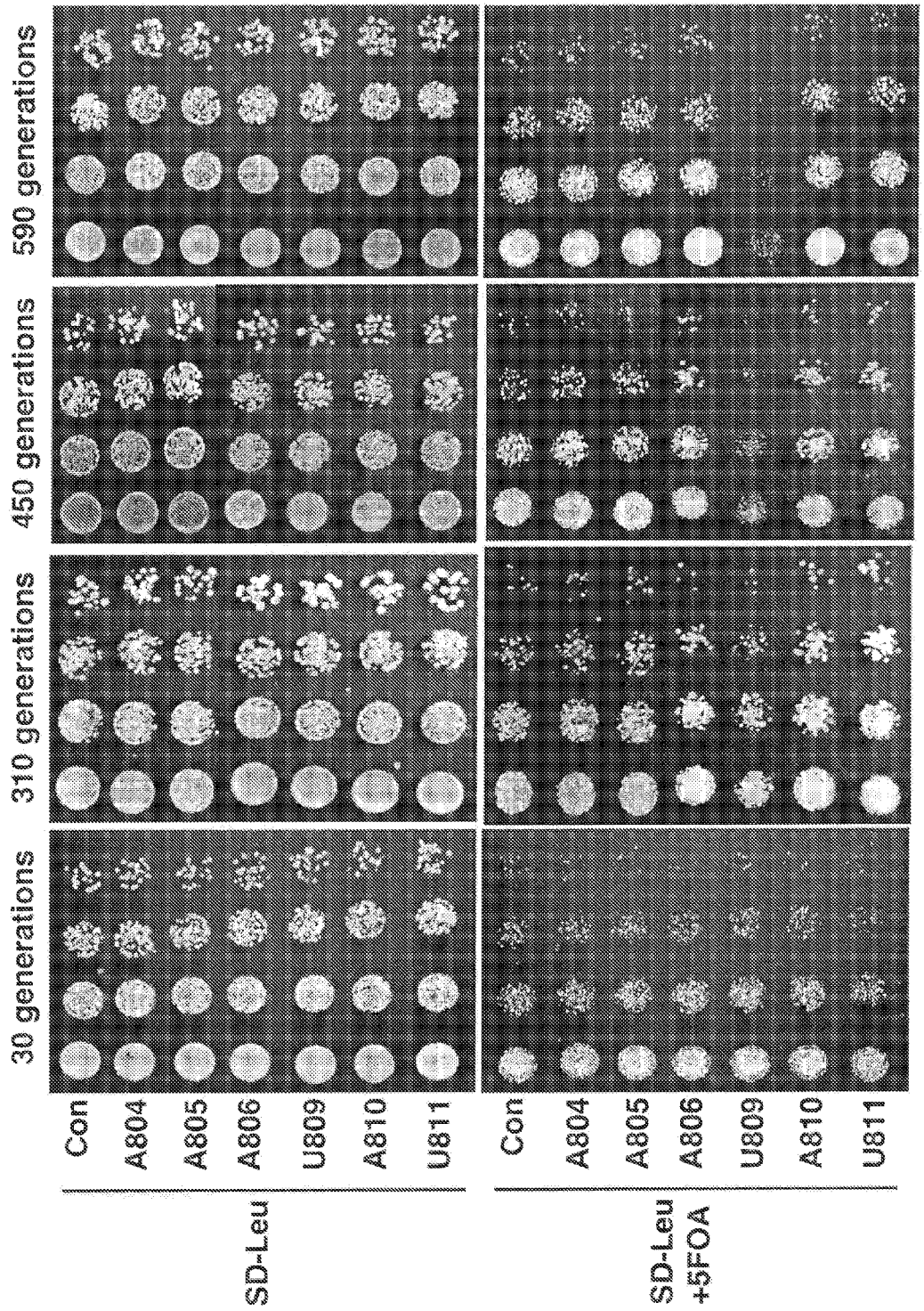
FIG. 6 shows the experimental results of a telomere position effect assay. (A) Cells (yCH-002) expressing a random gRNA (control), gRNA-A804, gRNA-A805, gRNA-A806, gRNA-U809, gRNA-A810 or gRNA-U811 were grown for the indicated number of generations and then plated on SD-Leu medium with or without 5-FOA. (B) DNAs were recovered from the cells described in (A), cleaved with PstI and hybridized with a URA3-specific radiolabeled probe and a chromosome IV—specific radiolabeled probe. Left panel: the schematic shows the modified chromosome VII with URA3 inserted near the telomere. A PstI site and the site of hybridization with the URA3 probe (a thick line with a star) are indicated. Right panel: the signals corresponding to the chromosome IV fragment and the telomere of chromosome VII are indicated.

Targeted 2'-O-Methylation Influences Telomerase Activity as Shown by the Telomere Position Effect Assay To further prove the effectiveness of the in vivo approach, an independent phenotypic assay involving the yeast strain (yHK53 rad52Δ::KanMX)(37) was used in which URA3 is inserted into chromosome VII near its end. Under normal conditions, the chromosome ends are stable and URA3 is silenced by the telomere position effect (Gottschling, D. E., et al., *Cell* 63:751-62 (1990)), thus allowing cells to grow on 5-FOA medium. When the chromosome ends are progressively shortened, URA3 is, however, progressively activated, which results in cell death on 5-FOA containing medium. Using this assay, a clear progressive growth defect for cells expressing gRNA-U809 was observed. In contrast, no growth defect on 5-FOA medium was observed when cells were transformed with any other gRNAs targeting a single nucleotide in the triple-helix region or with a control box C/D guide RNA containing a random guide sequence (FIG. 6A).

Figure 6B:
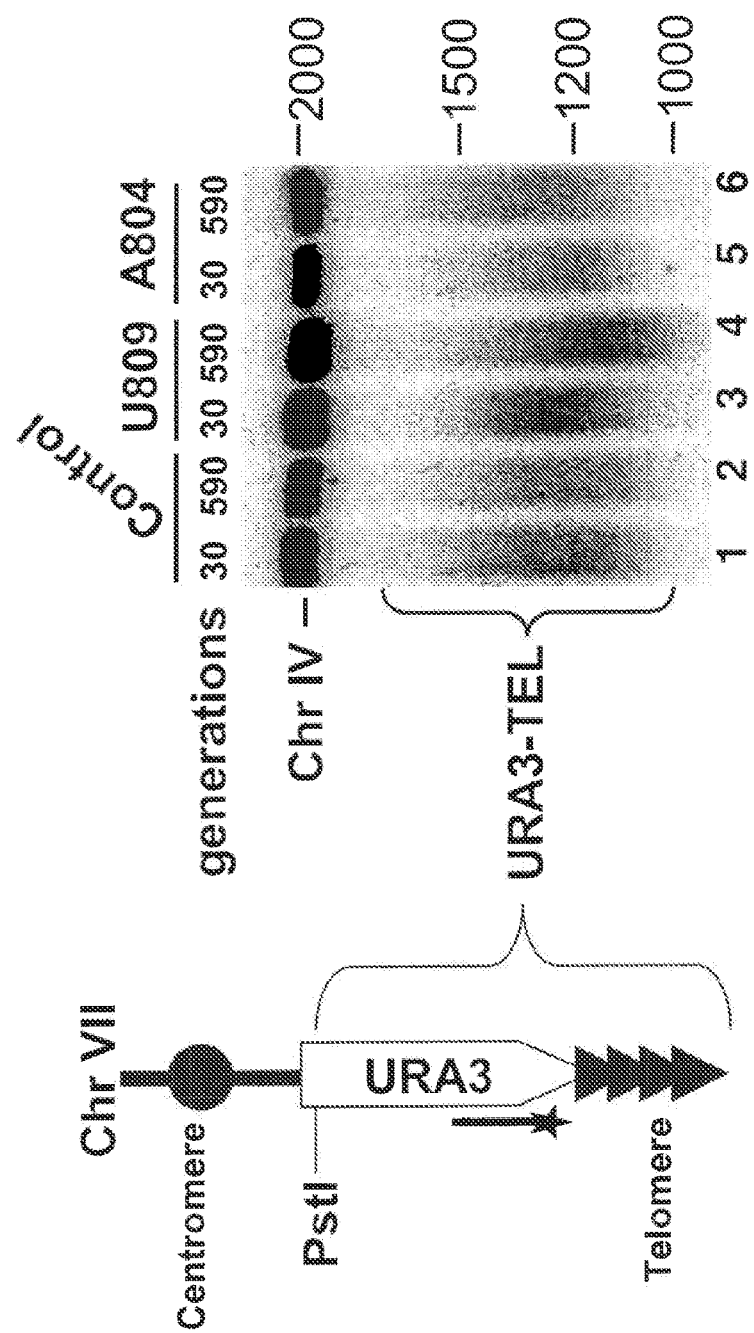

To confirm this observation, the telomere length of chromosome VII was measured using Southern analysis. Whereas no change in telomere length was detected when cells expressed a random (control) gRNA (FIG. 6B; compare lane 1 with lane 2), substantial telomere shortening was observed when cells were transformed with gRNAU809 (compare lane 3 with lane 4). Interestingly, a moderate lengthening of the end of chromosome VII was observed when cells received gRNA-A804 (compare lane 5 with lane 6), which is consistent with what was observed in other experiments (see FIGS. 4 and 5). Taken together, these results indicate that targeted telomerase RNA 2'-O-methylation is a very effective strategy for blocking telomerase activity in vivo.

Discussion

Using RNA-guided RNA modification, 2'-O-methylation sites were introduced into specific nucleotides in or adjacent to the triple-helix structure of *S. cerevisiae* TLC1 RNA, thereby affecting telomerase activity in vivo. Specifically, 2'-O-methylation at U809 resulted in telomere shortening, whereas 2'-O-methylation at A804 and A805 led to moderate lengthening of telomeres. These results appear to be consistent with the notion that the 2'-OH groups of the nucleotides within the triple-helix and the nearby stem contribute to function (directly or indirectly) (Qiao, F., et al., *Nat. Struct. Mol. Biol.* 15:634-40 (2008)). These results also suggest that RNA-guided RNA modification can serve as an effective tool for regulating telomerase activity (and RNA function in general) in vivo. With respect to telomerase function, Qiao, et al. demonstrated, using an in vitro system, that the 2'-OH groups of nucleotides in the triple-helix region, which are proximal to the catalytic active site, contribute to telomerase activity in vitro (Qiao, F., et al., *Nat. Struct. Mol. Biol.* 15:634-40 (2008)). Specifically, they show that the simultaneous changing of the 2'-OH groups of the triple-helix nucleotides (A804, A805, and A806) to 2'-H groups results in a substantial reduction in telomerase activity.

When the nucleotides (U809, A810 and U811) adjacent to the triple-helix structure are simultaneously changed to 2'-deoxy nucleotides, a substantial reduction of in vitro telomerase activity was observed. The above results show a clear reduction of telomerase activity both in vitro (FIG. 4) and in vivo (FIGS. 5 and 6) when U809, one of the three nucleotides adjacent to the triple-helix structure, was targeted for 2'-O-methylation, although targeting of either A810 or U811 did not lead to the reduction of telomerase activity. The above results thus suggest that it is the 2'-OH group of U809, rather than the 2'-OH groups of A810 and U811, that contributes to function. This approach added a methyl group to the sugar ring, thus the possibility cannot be excluded that such a modification disrupted the local structure of the RNA, thereby resulting in the reduction of telomerase activity.

Rather surprisingly, telomere lengthening was detected when 2'-O-methylation was introduced into either A804 or A805, two of the three triple-helix nucleotides (FIG. 5). This enhancing effect is in contrast to the inhibitory effect previously observed when the 2'-OH groups of the triple-helix nucleotides were changed to 2'-H groups (Qiao, F., et al., *Nat. Struct. Mol. Biol.* 15:634-40 (2008)). It is conceivable that if the 2'-OH group of A804 and/or A805 contributes directly to catalysis (as U809 does), changing the 2'-OH group to either 2'-H or 2'-OMethyl should dramatically alter its chemical properties (e.g., preventing hydrogen bond donation), thus resulting in a reduction (rather than an enhancement) of telomerase activity. Without wishing to be bound by theory, one possible explanation is that the 2'-OH groups of the triple-helix nucleotides may indirectly contribute to function (or catalysis): modifications at the 2' position may influence the configuration of the sugar pucker, either C3'-endo or C2'-endo configuration, which may in turn affect its function. A sugar pucker with a 2'-OH favors the C3'-endo conformation when compared with a sugar pucker with a 2'-H. However, when the 2'-OH of the sugar pucker is methylated (2'-OMethyl), the C3'-endo conformation becomes even more favorable (Hou, Y. M., et al., *Nucleic Acids Res.* 29:976-85 (2001); Uesugi, S., et al., *Tetrahedron Letters* 20:4073 (1979)). This order of preference (2'-OMethyl>2'-OH>2'-H) for the C3'-endo conformation would be consistent with the observed effect of different 2' moieties on telomerase activity if the C3'-endo (rather than C2'-endo) is the more functionally favorable conformation. Specifically, relative to 2'-OH, 2'-OMethyl enhances, while 2'-H inhibits, telomerase activity.

It is possible that it is the extensive base-pairing interactions between the guide sequence of gRNA and the target sequence of TLC RNA, rather than 2'-O-methylation per se, that has influenced telomerase activity. For instance, the base-pairing may have altered TLC RNA folding, localization and even telomerase RNP assembly. However, this possibility is unlikely for at least two reasons. First, clean and specific 2'-O-methylation at target sites was detected (FIG. 2B and FIG. 3E). Second, not all gRNAs, which targeted different nucleotides in the same region, exhibited an inhibitory or enhancing effect on telomerase activity. For instance, gRNA-U809 and gRNA-A810 targeted nucleotides adjacent to each other, but only gRNA-U809 exhibited an inhibitory effect on telomerase activity. Because both gRNAs maintained almost identical complementarity with TLC1 RNA, these results suggest that the observed inhibitory effect of targeting U809 was truly 2'-O-methylation-specific rather than an antisense effect that could impact TLC1 RNA folding, localization or RNP assembly.

Likewise, the same reasoning can be used to explain the enhancing effect of targeting A804 or A805 (comparing gRNA-A804 or gRNA-A805 with gRNA-A806). It should also be noted that the artificial guide RNAs used in this study may have unintended target(s), thus raising concerns about substrate specificity. To address this issue, the guide sequences (12 nt) were used to conduct a BLAST search against the yeast genome, with an attempt to identify other potential target RNAs. This search generated only few such candidates: Six (STE24, PRM4, NAM7, SMI1, PUF3 and TUS1) for gRNA-A804 and gRNA-A805, and one (STB4) for U809. None of these potential targets have known functions in telomere maintenance. Thus, it is unlikely that the observed effects are due to the non-specific effect of modifications of unintended off-targets.

With regard to the application of RNA-guided RNA modification, it is shown herein that an artificial box C/D guide RNA can efficiently target TLC1 2'-O-methylation at specific sites. The artificial guide RNA can be constructed according to a naturally occurring box C/D snoRNA (e.g., snR52). According to the sequence/site to be targeted, only the short guide sequences of the original box C/D snoRNA need to be altered, and the remaining sequences do not have to be changed. Such an approach to target an RNA at a specific site appears to be straightforward and effective and should be applicable to many different RNA types.

Although any nucleotides of an RNA can, in theory, be targeted in vivo, control of RNA localization remains a major issue that must be addressed. It is known that box C/D snoRNA (or RNP) is localized to the nucleoli and/or Cajal bodies (Kiss, T. et al., *Embo J* 20:3617-22 (2001)); however, some potential target RNAs (for example, mRNA) do not co-localize with snoRNA. The distinct localization of RNAs raises the question of whether all nuclear RNAs (including those that are temporarily present in the nucleus) can be targeted for modification. Although localization studies detect snoRNAs in the nucleoli and/or Cajal bodies (Balakin, et al., *Cell* 86:823-34 (1996), Darzacq, X., et al., *Embo J* 21:2746-56 (2002)), such studies do not exclude the possibility that snoRNAs may exist in the nucleoplasm as well. Perhaps the failure to detect snoRNAs in the nucleoplasm merely reflects the fact that snoRNAs are too dilute to be detected in this subnuclear compartment. In this regard, two reports have suggested that a U2-specific guide RNA (Zhao, X., et al., *Rna* 8:1515-25 (2002)) and a guide RNA specific for spliced-leader RNA (a special type of spliceosomal snRNA involved in trans-splicing) (Liang, X. H., et al., *Rna* 8:237-46 (2002)) may both reside within the nucleoplasm rather than within the nucleolus or Cajal bodies. Such conclusions are bolstered by a recent finding that suggests the presence of a number of *Drosophila melanogaster* snRNA-specific guide RNAs in the nucleoplasm as well as in Cajal bodies (Deryusheva, S., et al., Mol. Biol. Cell 20(24):5250-9 (2009)). In this regard, the present inventors and others have shown that mRNA as well as pre-mRNA can be targeted by artificial guide RNAs for modification in vivo (Cavaille, J., M. et al., *Nature* 383:732-5 (1996); Zhao, X., et al., *Nat. Methods* 5:95-100 (2008)); (Karijolich and Yu, unpublished data). Thus, it appears that RNA-guided RNA modification can occur in one or a few different nuclear subcompartments, including the nucleolus, Cajal bodies and/or even the nucleoplasm, and that RNA-guided RNA modification is a highly useful approach for regulating RNA function in eukaryotic cells.

Methods

Plasmids and *S. cerevisiae* Strains pSEC (snoRNA expression cassette) was constructed based on the parental yEPlac181 (a 2μ LEU2 vector kindly provided by Dr. E. M. Phizicky at University of Rochester) (Culver, G. M., et al., *J Biol. Chem.* 272:13203-10 (1997)). The GPD promoter region (a sequence corresponding to nucleotides –655 to 0 of TDH3) was inserted between EcoRI and BamH1. A 65-nt RNT1 element sequence (5'-TTTT-TATTTCTTTCTAAGTGGGTACTGGCAG-GAGTCGGGGCCTAGTTTAGAGA GAAGTAGACTCA-3') (SEQ ID NO: 327), corresponding to part of 35S pre-rRNA 3' ETS that is recognized by endonuclease RNT1 (RNase III activity) (Fatica, A., et al., *Embo J* 19:6218-29 (2000)), was inserted between BamH1 and SalI; a 55-nt snR13 termination sequence (5'-AGTAATCCTTCTTACAT-TGTATCGTAGCGCTGCATATATAATGCGTAAAATTT TC-3') (SEQ ID NO: 328), corresponding to nucleotides 26 to 80 downstream of snR13, was inserted between PstI and HindIII. The pSEC cassette thus constructed contains a pair of restriction sites (SalI and PstI) flanked by the RNT1 element on the 5' side and the snR13 termination sequence on the 3' side (Fatica, A., et al., *Embo J* 19:6218-29 (2000)). These two restriction sites were then used for insertion of an snR52-based artificial box C/D RNA gene (in which one of the guide sequences was altered), resulting in the production of pSEC-gRNA-A804, pSEC-gRNA-A805, pSECgRNA-A806, pSEC-gRNA-U809, pSEC-gRNA-A810, pSEC-gRNA-U811. Upon transformation into yeast cells, the mature artificial box C/D RNA (gRNA) was efficiently expressed (FIG. 2A).

Strain yCH-001 (snR52Δ::URA3, BY4741 background) was used for analyzing the expression of snR52-based artificial gRNAs. In addition, using the KanMX4 cassette (Ma, X., et al., *Embo J* 24:2403-13 (2005)), deleted RAD52 was deleted from another haploid strain yHK53 (Yu, Q., et al., *J. Biol. Chem.* 284:740-50 (2009)) (BY4741 background; MATa his3Δ1 leu2Δ0 met15Δ0 ura3Δ0 Tel VII-URA3; kindly provided by Dr. X. Bi at the University of Rochester), generating a new strain (yCH-002) that no longer had the Rad52-mediated alternative telomere maintenance pathway. yCH-002 was then used for both the telomere length assay (see below) and the telomere position effect assay (see below).

A yeast strain YKF103 (kindly provided by the Cech group), in which the chromosomal EST2 gene is fused with a protein A tag, was used for IgG Immunoprecipitation assay (Friedman, K. L., et al., *Genes Dev.* 13:2863-74 (1999)) (see below).

Northern Blot Assay

To examine gRNA expression, total RNAs isolated from cells (yCH-001) expressing no gRNA, a control gRNA, gRNA-A804, gRNA-A805, gRNA-A806, gRNA-U809, gRNAA810, or gRNA-U811 were used for Northern blot analysis (FIG. 2A). The hybridization was performed using two 5' end—radiolabeled DNA oligos: the first one was complementary to a snR52 sequence between box C' and box D' (5'-GTTTTTCTAATCCTAAAATCTTTCGATTTT-3') (SEQ ID NO: 329), and the second one was complementary to U1 snRNA (5'-AACGTCCTTCTACTATTGGAA-3') (SEQ ID NO: 330).

To check whether 2'-O-methylation affects TLC1 levels, yeast strain yCH-002 was transformed with pSEC-gRNA-Control, pSEC-gRNA-A804, pSEC-gRNA-A805, pSECgRNA-A806, pSEC-gRNA-U809, pSEC-gRNA-A810, or pSEC-gRNA-U811. After 30, 310, or 590 generations, cells were collected, total RNAs isolated, and Northern blotting performed. In brief, upon electrophoresis on a 4% polyacrylamide/8 M urea gel, RNAs were transferred to a HYBOND-N+ membrane (Amersham Pharmacia), and hybridized at room temperature with two 5' end-labeled DNA oligo probes; one was complementary to TLC1 RNA (5'-TTCTCTGTCACATCGTTCGATGTAC-3') (SEQ ID NO: 331), and the other was complementary to U1 snRNA (5'-AACGTCCTTCTACTATTGGAA-3') (SEQ ID NO: 332). After an overnight hybridization, the membrane was extensively washed, and TLC1 and U1 signals were revealed by autoradiography.

Northern analysis was also carried out to check whether 2'-O-methylated TLC1 RNA associated with Est2p (or was assembled onto RNP) (see Co-immunoprecipitation and Glycerol gradient assay below), Primer Extension-Based 2'-O-Methylation Assay A standard primer extension-based modification assay (with high and low dNTP concentrations) was performed essentially as described (42) to detect RNA 2'-O-methylation. Briefly, ~6 μg of total RNA, or ~200 ng of Co-immunoprecipitated TLC1 RNA (see below), was mixed with 5'-radiolabeled DNA oligonucleotide Detect-TLC-2Ome (5'-TTCTCTGTCACATCGTTCGATGTAC-3') (SEQ ID NO 333), and the primer extension reaction was carried out in the presence of either 1 mM dNTPs (high) or 0.01 mM dNTPs (low).

The reactions were incubated at 42° C. for 30 min and resolved on an 8% polyacryamide/8 M urea gel.

Ligation-Based Quantitative 2'-O-Methylation Assay

Using biotinylated antisense TLC1 DNA oligonucleotide (5'-biotin-TCAATCCGAAATCCGACACTATCTC-3') (SEQ ID NO: 334) and biotin-streptavidin affinity chromatography (Zhao, X., et al., *Rna* 8:1515-25 (2002), Zhao, X., et al., *Rna* 10:681-90 (2004)), TLC1 RNA was purified from 1 L yeast cells (OD600=7.0) that expressed no gRNA, a random (control) gRNA or gRNA targeting the nucleotides in and adjacent to the triple-helix region. Purified cellular TLC1 RNA served as the template in the subsequent ligation reaction.

To quantify the 2'-O-methylation at any particular site of TLC1 RNA, two parallel ligation reactions (discriminating and non-discriminating reactions) with two different site specific pairs of oligodeoxynucleotides were carried out at 37° C. for 30 min in the presence of 66 mM Tris-HCl (pH 7.6), 6.6 mM MgCl2, 10 mM dithiothreitol, 66 mM ATP, 15% DMSO, 0.125 U/μL T4 DNA ligase (Saikia, M., et al., *Rna* 12:2025-33 (2006)).

In the discriminating ligation reaction, a pair of discriminating DNA oligonucleotides (D oligo pair) was used to hybridize with TLC1 RNA. Consequently, the two oligos were precisely aligned, placing a nick or the ligation junction (between the two oligos) on the 3' side of U809. In the non-discriminating ligation reaction, a pair of nondiscriminating DNA oligonucleotides (ND oligo pair) was used. Upon hybridization with TLC1 RNA, the oligos were aligned, leaving a nick or the ligation junction on the 5' side of U809. It is well established that if the target nucleotide (U809) is 2'-O- methylated, only the non-discriminating oligo pair will be ligated; however, if U809 is not 2'-O-methylated, both pairs of oligos will be ligated (Saikia, M., et al., *Rna* 12:2025-33 (2006)), thus providing a quantitative measurement of 2'-O-methylation at U809.

For position 804 (A804), the D oligo pair were DF-804, 5'-GAAATTTCATCAGTAAGTTCAGTGAATAGATT-3' (SEQ ID NO: 335), and DA-804, 5'-[32P]TTTTATTTTAC-CTTTTTGTAGTGGG-3'(SEQ ID NO: 336); the ND oligo pair were NF-804, 5'-GAAATTTCATCAGTAAGTTCAGT-GAATAGATTT-3'(SEQ ID NO: 337), and NA-804, 5'-[32P]TTTATTTTACCTTTTTGTAGTGGG-3'(SEQ ID NO: 338). Similarly, for positions 805, 806, 809, 810 and 811, the D oligo pairs were, respectively, DF-805, 5'-GGAAATTTCAT-CAGTAAGTTCAGTGAATAGAT-3'(SEQ ID NO: 339), and DA-805, 5'-[32P]TTTTTATTTTACCTTTTTGTAGTGG-3' (SEQ ID NO: 340), DF-806, 5'-TGGAAATTTCATCAG-TAAGTTCAGTGAATAGA-3'(SEQ ID NO: 341), and DA-806, 5'-[32P]TTTTTTATTTTACCTTTTTGTAGTG-3' (SEQ ID NO: 342), DF-809, 5'-AATTTCATCAGTAAGT-TCAGTGAAT-3'(SEQ ID NO: 343), and DA-809, 5'-[32P] AGATTTTTTATTTTACCTTTTTGTA-3'(SEQ ID NO: 344), DF-810, 5'-AAATTTCATCAGTAAGTTCAGTGAA-3'(SEQ ID NO: 345), and DA-810, 5'-[32P]TAGATTTTT-TATTTTACCTTTTTGT-3'(SEQ ID NO: 346), and DF-811, 5'-GAAATTTCATCAGTAAGTTCAGTGA-3'(SEQ ID NO: 347), and DA-811, 5'-[32P]ATAGATTTTTTATTTTAC-CTTTTTG-3'(SEQ ID NO: 348); the ND oligo pairs were, respectively, NF-805, 5'-GGAAATTTCATCAGTAAGT-TCAGTGAATAGATT-3'(SEQ ID NO: 349), and NA-805, 5'-[32P]TTTTATTTTACCTTTTTGTAGTGG-3'(SEQ ID NO: 350), NF-806, 5'-TGGAAATTTCATCAGTAAGT-TCAGTGAATAGAT-3'(SEQ ID NO: 351), and NA-806, 5'-[32P]TTTTTATTTTACCTTTTTGTAGTG-3'(SEQ ID NO: 352), NF-809, 5'-AATTTCATCAGTAAGTTCAGT-GAATA-3'(SEQ ID NO: 353), and NA-809, 5'-[32P] GATTTTTTATTTTACCTTTTTGTA-3'(SEQ ID NO: 354), NF-810, 5'-AAATTTCATCAGTAAGTTCAGTGAAT-3' (SEQ ID NO: 355), and NA-810, 5'-[32P]AGATTTTT-TATTTTACCTTTTTGT-3'(SEQ ID NO: 356), and NF-811, 5'-GAAATTTCATCAGTAAGTTCAGTGAA-3'(SEQ ID NO: 357), and NA-811, 5'-[32P]TAGATTTTTTATTTTAC-CTTTTTG-3'(SEQ ID NO: 358). For sites U809, A810, and U811, the ligation products were 50 nucleotides long, and for sites A804, A805, and A806, the ligation products were 57 nucleotides long.

In all ligation reactions, another pair of DNA oligonucleotides (NF-1145, 5'-TTCCAAAAATTATCTAAA-3'(SEQ ID NO: 359); NA-1145, 5'-[321]TGCATCGAAGGCATT-AGGAGAAGTA-3') (SEQ ID NO: 360), which placed the ligation junction 5' of U1145 (a non-targeting site) of TLC1 RNA, was used as a loading control.

After the ligation reaction, the radioactively labeled oligos (ligated and unligated) were resolved on an 8% polyacryla-mide/8 M urea gel and quantified using a PhosphorImager (Molecular Dynamics).

Glycerol Gradient Assay

The procedure was essentially as described (Lingner, J., et al., *Science* 276:561-7 (1997)). Briefly, yeast cells from 2 L overnight cultures (SD leucine drop-out medium) were harvested at OD600=1.0. Pelleted cells were suspended in 4 mL of extraction buffer (20 mM Tris-acetate (pH 7.5), 300 mM potassium glutamate, 1.1 mM MgCl2, 0.1 mM EDTA, 5% glycerol, 1 mM dithiothreitol and 0.5 mM phenylmethylsulfonyl fluoride), placed in liquid nitrogen and ground with a mortar and pestle for 30 min. The lysate was concentrated three-fold in a Vivaspin ultrafiltration spin column and then loaded on the top of a 15-40% continuous glycerol gradient prepared with the extraction buffer. Ultracentrifugation (SW41Ti rotor, 150,000×g) was performed at 4° C. for 18 h. Nineteen fractions were collected, and RNA was extracted from each fraction for northern analysis (see above).

Co-Immunoprecipitation

Extracts were prepared from yeast cells (strain YKF103) expressing a control gRNA, gRNA-A804, gRNA-A805, gRNA-A806, gRNA-U809, gRNA-A810 or gRNAU811, according to the glass-bead lysis method (Friedman, K. L., et al., *Genes Dev.* 13:2863-74 (1999)). Briefly, 500 mL yeast cells (OD600=1.0) were lysed, by glass-bead beating, in TMG-300 NaCl buffer containing 10 mM Tris-HCl, pH 8.0, 1 mM MgCl2, 10% glycerol, 0.1 mM DTT, and 300 mM NaCl. After clarification by brief centrifugation (15,000×g at 4° C. for 5 min, repeated 3 times), total protein concentration was adjusted to 5 mg/mL. Upon addition of Tween-20 (to a final concentration of 0.5%), 500 µL of extract was mixed with 10 µL IgG Sepharose 6 Fast flow beads (GE healthcare). After overnight nutation at 4° C., the beads were collected, washed 3 times with TMG-200 NaCl-Tween buffer (10 mM Tris-HCl, pH 8.0, 1 mM MgCl2, 10% glycerol, 0.1 mM DTT, 200 mM NaCl, and 0.5 Tween) and one time with TMG-50 NaCl buffer (10 mM Tris-HCl, pH 8.0, 1 mM MgCl2, 10% glycerol, 0.1 mM DTT, 50 mM NaCl), and then resuspended in 20 µL TMG-50 NaCl buffer with 0.5 mM DTT. The beads were split into two equal aliquots of 10 µl each. One aliquot was used for in vitro telomerase activity assay (see below), and the other for TLC1 RNA extraction and analysis.

For TLC1 RNA extraction, 10 µL beads were treated with proteinase K at 37° C. for 30 min in a 200 µL reaction (10 mM Tris-HCl pH 8.0, 0.5% SDS, 0.4 mg/ml proteinase K). RNA was then PCA extracted and ethanol precipitated. Recovered TLC1 RNA was subsequently subjected to primer extension analysis (2'-O-methylation assay) and Northern blot analysis (see above).

Western Blot Assay

Western blot was performed essentially as previously described (Seto, A. G., et al., *Rna* 9:1323-32 (2003)). Briefly, 10 µL of immunoprecipitated beads were mixed with 10 µL 2× Laemmli loading buffer (125 mM Tris-HCl, pH 6.8, 4% SDS, 50% glycerol, 5% β-mercaptoethanol, 0.02% bromophenol blue). Upon incubation at 95° C. for 5 min, the supernatant was resolved on a 4-15% Tris-glycine gel (Bio-Rad). Protein was then transferred to a Protran nitrocellulose membrane (Whatman) and probed with antibodies. The primary antibody was rabbit IgG (Sigma), and the secondary was goat anti-rabbit IgG-AP conjugated antibody (BioRad).

Telomerase Activity Assay

In vitro telomerase activity assay was carried out as previously described (Seto, A. G., et al., *Rna* 9:1323-32 (2003)). Briefly, 2 µl of Est2p-bound beads derived from immunoprecipitation (see above) were added to a final 10 µl of reaction containing 40 mM Tris-HCl, pH 8.0, 50 mM NaCl, 5% glycerol, 2.5 mM MgCl2, 0.5 mM spermidine, 0.5 mM DTT, 2.5 µM telomerase substrate (5'-TGTGGTGTGTGTGGG-3') (SEQ ID NO: 361), 1 µL [α-32P] dGTP (10 µCi/µL), 1 µL [α-32P] dTTP (10 µCi/µL). After incubation at 30° C. for 20 min, the reaction was terminated by addition of 200 µL of proteinase K buffer (10 mM Tris-HCl pH 8.0, 0.5 SDS) and 4 µl, of proteinase K (20 mg/mL). The mixture was then incubated at 60° C. for 30 min. Nucleic acids were recovered by PCA extraction and ethanol precipitation. The primer-extended DNA products were resolved on a 14% polyacrylamide denaturing gel, and visualized by autoradiography.

Southern Analysis to Measure Telomere Length

For Southern blotting, yeast cells were grown to saturation in 20 mL SD leucine drop-out medium. The genomic DNA was subsequently extracted. Briefly, yeast cells were suspended in extraction buffer (10 mM Tris-HCl pH 8.0, 2% Triton X-100, 1% SDS, 1 mM EDTA). Upon the addition of saturated phenol and glass beads, cells were broken by vigorous vortexing. Cell extracts were treated with proteinase K (~0.4 mg/mL) at 55° C. for 2 h, and genomic DNA was subsequently purified via PureLink genomic DNA spin columns (Invitrogen). The purified genomic DNA was digested with XhoI, resolved on a 0.8% agarose gel, transferred onto a HYBOND-N+ membrane (Amersham Pharmacia) and hybridized with two radiolabeled probes, one against the telomeric repeat sequence probe (5'-TGTGGGTGTGGTGT-GTGGGTGTGGTG-3') (SEQ ID NO: 362) and the other (as a control) against chromosome IV (nucleotides 31051-31075; 5'-GTCTGGCCTATGGTGCTAGTAGTAC-3') (SEQ ID NO: 363).

For detecting URA3 integrated into chromosome VII (yCH-002 strain), purified genomic DNA was digested with PstI and hybridized with a URA3-specific probe (5'-ACAT-TATTATTGTTGGAAGAGGACT-3') (SEQ ID NO: 364) and a control probe against chromosome IV (nucleotides 194700-194676; 5'-GATACACCTTCCGTTTCTGACCCAT-3') (SEQ ID NO: 365).

Telomere Position Effect Assay

After transformation with various pSEC-gRNA plasmids, cells were plated onto solid medium, and a single colony was picked and grown to saturation in 5 mL of SD leucine drop-out medium. One microliter of the liquid culture was then withdrawn, placed in 5 mL of fresh SD leucine drop-out medium and grown to saturation again. This cycle was repeated until the cells reached 590 generations. At 310, 450 and 590 generations, an aliquot of cells was saved and stored at −80° C. for future use. To assay growth phenotype, cells from different generations were first diluted to OD600=0.1 and then plated with a series of five-fold dilutions on the SD leucine drop-out solid medium with or without 5-FOA (1 mg/mL) The growth phenotype was monitored at 30° C.

What is claimed is:

1. A method for increasing telomere length comprising:
   providing a yeast cell expressing a telomerase ribonucleoprotein comprising a yeast telomerase RNA;
   providing a nucleic acid encoding, a C/D box snoRNA guide RNA that causes a 2'-O-methylation modification of nucleotide A804 or A805 in the yeast telomerase RNA to the cell in a manner that causes the guide RNA to be expressed in the cell.

2. The method of claim 1, wherein the yeast telomerase RNA is encoded by a nucleic acid comprising SEQ ID NO: 282.

3. The method of claim 1, where in the C/D box snoRNA is transcribed from a nucleic acid sequence comprising a sequence selected from SEQ ID NOs: 321 or 322.

4. The method of claim 1, wherein the process is performed in vivo.

* * * * *

```
                        SEQUENCE LISTING

<160> NUMBER OF SEQ ID NOS: 433

<210> SEQ ID NO 1
<211> LENGTH: 91
<212> TYPE: DNA
<213> ORGANISM: Homo sapiens

<400> SEQUENCE: 1
tcactgtgat gatggttttc caacattcgc agtttccacc agaaaggttt tccttagtgt      60
tgggtaaacc ttccttggat gtctgagtga g                                     91

<210> SEQ ID NO 2
<211> LENGTH: 92
<212> TYPE: DNA
<213> ORGANISM: Homo sapiens

<400> SEQUENCE: 2
tcactatgat gattggttgc cagacattcg cagtttccac cagaaatgtt tttccttatg      60
ttggccagtt cttccttgga tgtctgagtg ag                                    92

<210> SEQ ID NO 3
<211> LENGTH: 148
<212> TYPE: DNA
<213> ORGANISM: Homo sapiens

<400> SEQUENCE: 3
cttcgatgaa gagatgatga cgagtctgac ttggggatgt tctctttgcc caggtggcct      60
actctgtgct gcgttctgtg gcacagttta aagagccctg gttgaagtaa tttcctaaag     120
atgacttaga ggcatttgtc tgagaagg                                        148

<210> SEQ ID NO 4
<211> LENGTH: 146
<212> TYPE: DNA
<213> ORGANISM: Homo sapiens

<400> SEQUENCE: 4
cttcagtgat gacacgatga cgagtcagaa aggtcacgtc ctgctcttgg tccttgtcag      60
tgccatgttc tgtggtgctg tgcacgagtt cctttggcag aagtgtccta tttattgatc     120
gatttagagg catttgtctg agaagg                                          146
```

<210> SEQ ID NO 5
<211> LENGTH: 101
<212> TYPE: DNA
<213> ORGANISM: Homo sapiens

<400> SEQUENCE: 5
ttgcaatgat gtcgtaattt gcgtcttact ctgttctcag cgacagttgc ctgctgtcag    60
taagctggta cagaaggttg acgaaaattc ttactgagca a                       101

<210> SEQ ID NO 6
<211> LENGTH: 237
<212> TYPE: DNA
<213> ORGANISM: Homo sapiens

<400> SEQUENCE: 6
gtgaaatgat gattcagttt atccattcgc tgagtgcgct gcactgacct tcttccaagc    60
ctcagttcct gttctaggaa cttgaggcta tgtagcctga aaatgccctg cagtctgcag   120
tgttctactg tgaactgctt gtgtgttggc aggctaccgg taagaatggt tggtgtcagc   180
agggacgggg ccctctgaga cccatctcac aaagatgagt ggtgaaaatc tgatcac      237

<210> SEQ ID NO 7
<211> LENGTH: 70
<212> TYPE: DNA
<213> ORGANISM: Homo sapiens

<400> SEQUENCE: 7
cagtagtgat gaaattccac ttcattggtc cgtgtttctg aaccacatga ttttctcgga    60
tgttctgatg                                                           70

<210> SEQ ID NO 8
<211> LENGTH: 70
<212> TYPE: DNA
<213> ORGANISM: Homo sapiens

<400> SEQUENCE: 8
tcaaaatgat gagattccac ttaattggtc cgtgtttctg aaacacatga tatttgtgga    60
aattctgact                                                           70

<210> SEQ ID NO 9
<211> LENGTH: 67
<212> TYPE: DNA
<213> ORGANISM: Homo sapiens

<400> SEQUENCE: 9
ttgttatgat gagattccac ttaaggtccg tgtttctgaa acaaatgatt ttgtggaagt    60
tctgatt                                                              67

<210> SEQ ID NO 10
<211> LENGTH: 76
<212> TYPE: DNA
<213> ORGANISM: Homo sapiens

<400> SEQUENCE: 10
acatgggtga ggtacgagga aacagtctga tagtcactga agactgatta gatccaactc    60
tgatctcagc aaagcc                                                    76

<210> SEQ ID NO 11

```
<211> LENGTH: 84
<212> TYPE: DNA
<213> ORGANISM: Homo sapiens

<400> SEQUENCE: 11
ttttggttga aatatgatga gtgtacaaaa tcttgattta agtgaatgaa aaattacaag    60
atccaactct gatttcagcc agag                                          84

<210> SEQ ID NO 12
<211> LENGTH: 80
<212> TYPE: DNA
<213> ORGANISM: Homo sapiens

<400> SEQUENCE: 12
tggatatgat gactgattac ctgagaaata attgatgaaa tctcaagaaa attcctctag    60
atagtcaagt tctgatccag                                               80

<210> SEQ ID NO 13
<211> LENGTH: 95
<212> TYPE: DNA
<213> ORGANISM: Homo sapiens

<400> SEQUENCE: 13
gctgaatgat gatatcccac taactgagca gtcagtagtt ggtcctttgg ttgcatatga    60
tgcgataatt gtttcaagac gggactgatg gcagc                              95

<210> SEQ ID NO 14
<211> LENGTH: 126
<212> TYPE: DNA
<213> ORGANISM: Homo sapiens

<400> SEQUENCE: 14
tcccaatgaa gaaactttca catgtcttac tctctgtcct agtcccagag cctgtaaagg    60
tgaacccact gggactggct gggggagaag aggaagattt gttccagaag gaactgtctg   120
agggat                                                             126

<210> SEQ ID NO 15
<211> LENGTH: 110
<212> TYPE: DNA
<213> ORGANISM: Homo sapiens

<400> SEQUENCE: 15
tgcccagtga tgacaccatc cttgctcccc gtgccccca ggggctatgg gcgacaccat     60
ggctgcccct gggctgggcc agtggggcca atgcccaggg gctgagggca              110

<210> SEQ ID NO 16
<211> LENGTH: 75
<212> TYPE: DNA
<213> ORGANISM: Homo sapiens

<400> SEQUENCE: 16
tgcagatgat gtaaaagaat atttgctatc tgagagatgg tgatgacatt ttaaaccacc    60
aagatcgctg atgca                                                   75

<210> SEQ ID NO 17
<211> LENGTH: 67
<212> TYPE: DNA
<213> ORGANISM: Homo sapiens

<400> SEQUENCE: 17
```

```
ttcctatgat gaggaccttt tcacagacct gtactgagct ccgtgaggat aaataactct    60
gaggaga                                                              67

<210> SEQ ID NO 18
<211> LENGTH: 75
<212> TYPE: DNA
<213> ORGANISM: Homo sapiens

<400> SEQUENCE: 18
ctacggggat gattttacga actgaactct ctctttctga tggattagtg gagaaaacag    60
aaaattctga gtagc                                                     75

<210> SEQ ID NO 19
<211> LENGTH: 72
<212> TYPE: DNA
<213> ORGANISM: Homo sapiens

<400> SEQUENCE: 19
actccatgat gaacacaaaa tgacaagcat atggctgaac tttcaagtga tgtcatctta    60
ctactgagaa gt                                                        72

<210> SEQ ID NO 20
<211> LENGTH: 75
<212> TYPE: DNA
<213> ORGANISM: Homo sapiens

<400> SEQUENCE: 20
gtcagatgat ttgaattgat aagctgatgt tctgtgaggt acaaaagtta atagcatgtt    60
agagttctga tggca                                                     75

<210> SEQ ID NO 21
<211> LENGTH: 65
<212> TYPE: DNA
<213> ORGANISM: Homo sapiens

<400> SEQUENCE: 21
tttctatgat gaatcaaact agctcactat gaccgacagt gaaaatacat gaacacctga    60
gaaac                                                                65

<210> SEQ ID NO 22
<211> LENGTH: 70
<212> TYPE: DNA
<213> ORGANISM: Homo sapiens

<400> SEQUENCE: 22
gtttgtgatg acttacatgg aatctcgttc ggctgatgac ttgctgttga gactctgaaa    60
tctgattttc                                                           70

<210> SEQ ID NO 23
<211> LENGTH: 71
<212> TYPE: DNA
<213> ORGANISM: Homo sapiens

<400> SEQUENCE: 23
ctcaccagtg atgagttgaa taccgcccca gtctgatcaa tgtgtgactg aaaggtattt    60
tctgagctgt g                                                         71

<210> SEQ ID NO 24
```

```
<211> LENGTH: 77
<212> TYPE: DNA
<213> ORGANISM: Homo sapiens

<400> SEQUENCE: 24
gtcagtgatg agcaacattc accatctttc gtttgagtct cacggccatg agatcaaccc    60
catgcaccgc tctgaga                                                   77

<210> SEQ ID NO 25
<211> LENGTH: 77
<212> TYPE: DNA
<213> ORGANISM: Homo sapiens

<400> SEQUENCE: 25
attggtgatg agcaacaatc accatctttc gtttgagtct catggccatg agaccaaccc    60
catgcactgc tctgaga                                                   77

<210> SEQ ID NO 26
<211> LENGTH: 66
<212> TYPE: DNA
<213> ORGANISM: Homo sapiens

<400> SEQUENCE: 26
cgtccatgat gttccgcaac tacctacatt gtttgatcct catgaaagca gcactggctg    60
agacgc                                                               66

<210> SEQ ID NO 27
<211> LENGTH: 86
<212> TYPE: DNA
<213> ORGANISM: Homo sapiens

<400> SEQUENCE: 27
ggcagatgat gtccttatct cacgatggtc tgcggatgtc cctgtgggaa tggcgacaat    60
gccaatggct tagctgatgc caggag                                         86

<210> SEQ ID NO 28
<211> LENGTH: 88
<212> TYPE: DNA
<213> ORGANISM: Homo sapiens

<400> SEQUENCE: 28
tggcagatga tgtttgtttt cacgatggtc ttcagatgcc cacgtgggca ctgctgagaa    60
agccacttgg taaaactgat gccggaaa                                       88

<210> SEQ ID NO 29
<211> LENGTH: 72
<212> TYPE: DNA
<213> ORGANISM: Homo sapiens

<400> SEQUENCE: 29
ttgcaatgat gtgaatctct cactgaattc aaccttgaag tgcgaatcca tgagcttttt    60
aaccctgagc aa                                                        72

<210> SEQ ID NO 30
<211> LENGTH: 71
<212> TYPE: DNA
<213> ORGANISM: Homo sapiens

<400> SEQUENCE: 30
gttgcagtga tgtaaaattt cttggcctga aattactgtg aagagtaaaa ccgagctttt    60
```

```
taacactgag t                                                           71

<210> SEQ ID NO 31
<211> LENGTH: 68
<212> TYPE: DNA
<213> ORGANISM: Homo sapiens

<400> SEQUENCE: 31
ttgccaatga tggttaagaa tttcttcacc tgaataaacc atgtggtcag cattgcatct      60
gaggcaaa                                                               68

<210> SEQ ID NO 32
<211> LENGTH: 66
<212> TYPE: DNA
<213> ORGANISM: Homo sapiens

<400> SEQUENCE: 32
attcgtgatg actgatcatt tcttcacttt gaccagatgt ctactgaaga aagcctgcgt      60
ctgagg                                                                 66

<210> SEQ ID NO 33
<211> LENGTH: 71
<212> TYPE: DNA
<213> ORGANISM: Homo sapiens

<400> SEQUENCE: 33
ttctcgtgat gaaaactctg tccagttctg ctactgaagg gagagagatg agagcctttt      60
aggctgagga a                                                           71

<210> SEQ ID NO 34
<211> LENGTH: 69
<212> TYPE: DNA
<213> ORGANISM: Homo sapiens

<400> SEQUENCE: 34
tctcagtgat gaaaactttg tccagttctg ctactgacag taagtgaaga taaagtgtgt      60
ctgaggaga                                                              69

<210> SEQ ID NO 35
<211> LENGTH: 70
<212> TYPE: DNA
<213> ORGANISM: Homo sapiens

<400> SEQUENCE: 35
tgggaagtga tgacacctgt gactgttgat gtggaactga tttatcgcgt attcgtactg      60
gctgatcctg                                                             70

<210> SEQ ID NO 36
<211> LENGTH: 58
<212> TYPE: DNA
<213> ORGANISM: Homo sapiens

<400> SEQUENCE: 36
aatgatggaa aaatcattat tggaaaagaa tgacatgaac aaaggaacca ctgaagtg        58

<210> SEQ ID NO 37
<211> LENGTH: 67
<212> TYPE: DNA
<213> ORGANISM: Homo sapiens
```

<400> SEQUENCE: 37
gtgcatatga tggaaaagtt ttaatctcct gacacttgtg atgtcttcaa aggaaccact    60
gatgcac                                                              67

<210> SEQ ID NO 38
<211> LENGTH: 62
<212> TYPE: DNA
<213> ORGANISM: Homo sapiens

<400> SEQUENCE: 38
cacagatgat gaacttattg acgggcggac agaaactgtg tgctgattgt cacgttctga    60
tt                                                                   62

<210> SEQ ID NO 39
<211> LENGTH: 63
<212> TYPE: DNA
<213> ORGANISM: Homo sapiens

<400> SEQUENCE: 39
cctggatgat gataagcaaa tgctgactga acatgaaggt cttaattagc tctaactgac    60
taa                                                                  63

<210> SEQ ID NO 40
<211> LENGTH: 83
<212> TYPE: DNA
<213> ORGANISM: Homo sapiens

<400> SEQUENCE: 40
ggtcaatgat gtgttggcat gtattatctg aatctattgc tgatgtgtaa taacactta    60 gctctagaat tactctgaga cct                                            83

<210> SEQ ID NO 41
<211> LENGTH: 71
<212> TYPE: DNA
<213> ORGANISM: Homo sapiens

<400> SEQUENCE: 41
ggtcaatgat gtaatggcat gtattagctg aatctaaagt tgatgtgagt tctaaaatta    60
cactgagacc t                                                         71

<210> SEQ ID NO 42
<211> LENGTH: 78
<212> TYPE: DNA
<213> ORGANISM: Homo sapiens

<400> SEQUENCE: 42
ggtcaatgat gagttggcat gtattctgaa tctaaagttg attattacta ctttagctct    60
agaattactc tgagacct                                                  78

<210> SEQ ID NO 43
<211> LENGTH: 98
<212> TYPE: DNA
<213> ORGANISM: Homo sapiens

<400> SEQUENCE: 43
gtagggtgat gaaaaagaat ccttaggcgt ggttgtggcc gtcttggtca cctgtgtgcc    60
acttgccaat gcaaggactt gtcatagtta cactgact                            98

```
<210> SEQ ID NO 44
<211> LENGTH: 65
<212> TYPE: DNA
<213> ORGANISM: Homo sapiens

<400> SEQUENCE: 44
taatgattct gccaaatgaa atataatgat atcactgtaa aaccgttcca ttttgattct    60
gaggt                                                                65

<210> SEQ ID NO 45
<211> LENGTH: 64
<212> TYPE: DNA
<213> ORGANISM: Homo sapiens

<400> SEQUENCE: 45
agtgatgatg accccaggta actcttgagt gtgtcgctga tgccatcacc gcagcgctct    60
gacc                                                                 64

<210> SEQ ID NO 46
<211> LENGTH: 71
<212> TYPE: DNA
<213> ORGANISM: Homo sapiens

<400> SEQUENCE: 46
tgctctgatg aaatcactaa taggaagtgc cgtcagaagc gataactgac gaagactact    60
cctgtctgat t                                                         71

<210> SEQ ID NO 47
<211> LENGTH: 48
<212> TYPE: DNA
<213> ORGANISM: Homo sapiens

<400> SEQUENCE: 47
ctgatgatac ttgtaatagg aagtgccgtc agaagcgata actgacga                 48

<210> SEQ ID NO 48
<211> LENGTH: 75
<212> TYPE: DNA
<213> ORGANISM: Homo sapiens

<400> SEQUENCE: 48
tatctgtgat gatcttatcc cgaacctgaa cttctgttga aaaaaaaaa cttttacgga    60 tctggcttct gagat                                                     75

<210> SEQ ID NO 49
<211> LENGTH: 71
<212> TYPE: DNA
<213> ORGANISM: Homo sapiens

<400> SEQUENCE: 49
taatcaatga tgaaacctat cccgaagctg ataacctgaa gaaaaataag tacggattcg    60
gcttctgaga t                                                         71

<210> SEQ ID NO 50
<211> LENGTH: 70
<212> TYPE: DNA
<213> ORGANISM: Homo sapiens

<400> SEQUENCE: 50
gttgcatgat gaataaaatc aaatcaccat ctttcggctg agttcgtgat ggatttgctt    60
```
ttttctgatt 70

<210> SEQ ID NO 51
<211> LENGTH: 64
<212> TYPE: DNA
<213> ORGANISM: Homo sapiens

<400> SEQUENCE: 51
gggaatgatg atttcacaga ctagagtctc cgatgctggt catgatgtca aaactaagtt 60
ctga 64

<210> SEQ ID NO 52
<211> LENGTH: 78
<212> TYPE: DNA
<213> ORGANISM: Homo sapiens

<400> SEQUENCE: 52
atgctatgat gacatccata tggtttcgct gctggctgag tttcagagat gacacctttc 60
tcttggctgt ctgagcat 78

<210> SEQ ID NO 53
<211> LENGTH: 63
<212> TYPE: DNA
<213> ORGANISM: Homo sapiens

<400> SEQUENCE: 53
tggcgatgag gaggtaccta ttgtgttgag taacggtgat aattttatac gctattctga 60
gcc 63

<210> SEQ ID NO 54
<211> LENGTH: 71
<212> TYPE: DNA
<213> ORGANISM: Homo sapiens

<400> SEQUENCE: 54
ccacaatgat ggcaatattt ttcgtcaaca gcagttcacc tagtgagtgt tgagactctg 60
ggtctgagtg a 71

<210> SEQ ID NO 55
<211> LENGTH: 72
<212> TYPE: DNA
<213> ORGANISM: Homo sapiens

<400> SEQUENCE: 55
tggaggtgat gaactgtctg agcctgacct tgtagaatgg aggcaaaaaa actgatttaa 60
tgagcctgat cc 72

<210> SEQ ID NO 56
<211> LENGTH: 65
<212> TYPE: DNA
<213> ORGANISM: Homo sapiens

<400> SEQUENCE: 56
ctgcagtgat gactttctta ggacaccttt ggatttaccg tgaaaattaa taaattctga 60
gcagc 65

<210> SEQ ID NO 57
<211> LENGTH: 66
<212> TYPE: DNA
<213> ORGANISM: Homo sapiens

```
<400> SEQUENCE: 57
ctgcgatgat ggcatttctt aggacacctt tggattaata atgaaaacaa ctactctctg    60
agcagc                                                               66

<210> SEQ ID NO 58
<211> LENGTH: 65
<212> TYPE: DNA
<213> ORGANISM: Homo sapiens

<400> SEQUENCE: 58
ttgctgtgat gactatctta ggacaccttt ggaataacta tgaaagaaaa ctattctgag    60
caacc                                                                65

<210> SEQ ID NO 59
<211> LENGTH: 75
<212> TYPE: DNA
<213> ORGANISM: Homo sapiens

<400> SEQUENCE: 59
ccttctatga tgattttatc aaaatgactt tcgttcttct gagtttgctg aagccacatt    60
taggtactga gaagg                                                     75

<210> SEQ ID NO 60
<211> LENGTH: 75
<212> TYPE: DNA
<213> ORGANISM: Homo sapiens

<400> SEQUENCE: 60
tattcctcac tgatgagtac gttctgactt tcgttcttct gagtttgctg aagccagatg    60
caatttctga gaagg                                                     75

<210> SEQ ID NO 61
<211> LENGTH: 83
<212> TYPE: DNA
<213> ORGANISM: Homo sapiens

<400> SEQUENCE: 61
agtctgtgat gaattgcttt gacttctgac acctcgtatg aaaactgcac gtgcagtctg    60
attatttagc aagactgagg ctt                                            83

<210> SEQ ID NO 62
<211> LENGTH: 73
<212> TYPE: DNA
<213> ORGANISM: Homo sapiens

<400> SEQUENCE: 62
gctatgatga atttgattgc attgatcgtc tgacatgata atgtattttt gtcctctaag    60
aagttctgag ctt                                                       73

<210> SEQ ID NO 63
<211> LENGTH: 86
<212> TYPE: DNA
<213> ORGANISM: Homo sapiens

<400> SEQUENCE: 63
tctcagtgat gtaattccaa tagatccttc tgaccctcca ctgtggactc aatagcaggg    60
agatgaagag gacagtgact gagaga                                         86
```

```
<210> SEQ ID NO 64
<211> LENGTH: 86
<212> TYPE: DNA
<213> ORGANISM: Homo sapiens

<400> SEQUENCE: 64
tctcagtgat gtaattccaa tagatccttc tgaccctcca ctgtggactc aatagcaggg    60
agatgaagag gacagtgact gagaga                                        86

<210> SEQ ID NO 65
<211> LENGTH: 68
<212> TYPE: DNA
<213> ORGANISM: Homo sapiens

<400> SEQUENCE: 65
gtgcaatgat gtattttatt caacacatca ttctgaaaga acgtgtggaa aactaatgac    60
tgagcaca                                                            68

<210> SEQ ID NO 66
<211> LENGTH: 67
<212> TYPE: DNA
<213> ORGANISM: Homo sapiens

<400> SEQUENCE: 66
ggatttgtga tgagctgtgt ttactgagca tgatgaagta aagctcaacg tgattactct    60
gaagtcc                                                             67

<210> SEQ ID NO 67
<211> LENGTH: 73
<212> TYPE: DNA
<213> ORGANISM: Homo sapiens

<400> SEQUENCE: 67
aaatgatgaa atcacccaaa atagctggaa ttaccggcag attgtgtagt ggtgaaccta    60
tggttttctg aag                                                      73

<210> SEQ ID NO 68
<211> LENGTH: 76
<212> TYPE: DNA
<213> ORGANISM: Homo sapiens

<400> SEQUENCE: 68
ttcctctgat gacttcctgt tagtgccacg tgtctgggcc actgagacac catgatggaa    60
ctgaggatct gaggaa                                                   76

<210> SEQ ID NO 69
<211> LENGTH: 111
<212> TYPE: DNA
<213> ORGANISM: Homo sapiens

<400> SEQUENCE: 69
tgtgagagtg atgagttgca cactggtgga gccatggtat caggtgatac aggcaccact    60
cagtatcacc ctggtgacaa aatcaagtgc acaggggcca tctgactcac a            111

<210> SEQ ID NO 70
<211> LENGTH: 77
<212> TYPE: DNA
<213> ORGANISM: Homo sapiens

<400> SEQUENCE: 70
```

```
aatgtgaagc aaatgatgat aaactggatc tgactgactg tgctgagtct gttcaatcca    60
accctgagct tcatgtt                                                   77

<210> SEQ ID NO 71
<211> LENGTH: 88
<212> TYPE: DNA
<213> ORGANISM: Homo sapiens

<400> SEQUENCE: 71
ttcgttgttg tcaatgatgt attcttcttg gaactgaatc taagtgatct gactcaatat    60
tcgtcactac cactgagaca acgatgaa                                       88

<210> SEQ ID NO 72
<211> LENGTH: 86
<212> TYPE: DNA
<213> ORGANISM: Homo sapiens

<400> SEQUENCE: 72
tgtgtgttgg aggatgaaag tacggagtga tccatcggct aagtgtcttg tcacaatgct    60
gacactcaaa ctgctgacag cacacg                                         86

<210> SEQ ID NO 73
<211> LENGTH: 80
<212> TYPE: DNA
<213> ORGANISM: Homo sapiens

<400> SEQUENCE: 73
agcttatcag tgatgttgta aaaataaatg tctgaacata tgaatgcagt attgatttca    60
gcatttaact gagataagcg                                                80

<210> SEQ ID NO 74
<211> LENGTH: 65
<212> TYPE: DNA
<213> ORGANISM: Homo sapiens

<400> SEQUENCE: 74
aataagtgat gaaaaaagtt tcggtcccag atgatggcca gtgataacaa cattttctg    60 atgtt                                                                65

<210> SEQ ID NO 75
<211> LENGTH: 75
<212> TYPE: DNA
<213> ORGANISM: Homo sapiens

<400> SEQUENCE: 75
aatgaatgat gacaaaatgt ttcagtccca aatgatacat actgattata ccattatatt    60
tatcctgaca ttcct                                                     75

<210> SEQ ID NO 76
<211> LENGTH: 72
<212> TYPE: DNA
<213> ORGANISM: Homo sapiens

<400> SEQUENCE: 76
ctgcctctga tgaagcctgt gttggtaggg acatctgaga gtaatgatga atgccaaccg    60
ctctgatggt gg                                                        72

<210> SEQ ID NO 77
```

```
<211> LENGTH: 60
<212> TYPE: DNA
<213> ORGANISM: Homo sapiens

<400> SEQUENCE: 77
agcctgtgat gctttaagag tagtggacag aagggatttc tgaaattcta ttctgaggct    60

<210> SEQ ID NO 78
<211> LENGTH: 80
<212> TYPE: DNA
<213> ORGANISM: Homo sapiens

<400> SEQUENCE: 78
gccacaatga tgacagttta tttgctactc ttgagtgcta aatgatgag gatcttaacc    60 accattatct taactgaggc                                                80

<210> SEQ ID NO 79
<211> LENGTH: 70
<212> TYPE: DNA
<213> ORGANISM: Homo sapiens

<400> SEQUENCE: 79
agatactatg atggttgcat agttcagcag atttaatcat gaagagatgt actatctgtc    60
tgatgtatct                                                           70

<210> SEQ ID NO 80
<211> LENGTH: 65
<212> TYPE: DNA
<213> ORGANISM: Homo sapiens

<400> SEQUENCE: 80
gtgtaatgat gttgatcaaa tgtctgacct gaaatgagca tgtagacaaa ggtaacactg    60
aagaa                                                                65

<210> SEQ ID NO 81
<211> LENGTH: 85
<212> TYPE: DNA
<213> ORGANISM: Homo sapiens

<400> SEQUENCE: 81
tactgttagt gatgatttta aaattaaagc agatgggaat ctctctgaga aagaaaatgg    60
agattaatct taaactgaaa cagta                                          85

<210> SEQ ID NO 82
<211> LENGTH: 78
<212> TYPE: DNA
<213> ORGANISM: Homo sapiens

<400> SEQUENCE: 82
gatacaatga tgataacata gttcagcaga ctaacgctga tgagcaatat taagtctttc    60
gctcctatct gatgtatc                                                  78

<210> SEQ ID NO 83
<211> LENGTH: 77
<212> TYPE: DNA
<213> ORGANISM: Homo sapiens

<400> SEQUENCE: 83
cagaatacat gatgatctca atccaacttg aactctctca ctgattactt gatgacaata    60
aaatatctga tattctg                                                   77
```

<210> SEQ ID NO 84
<211> LENGTH: 75
<212> TYPE: DNA
<213> ORGANISM: Homo sapiens

<400> SEQUENCE: 84
acagcacaaa tgatgaataa caaagggact taatactgaa acctgatgtt acattgtagt    60
gtgctgatgt gctgt    75

<210> SEQ ID NO 85
<211> LENGTH: 95
<212> TYPE: DNA
<213> ORGANISM: Homo sapiens

<400> SEQUENCE: 85
gctgttcgtt gatgaggctc agagtgagcg ctgggtacag cgcccgaatc ggacagtgta    60
gaaccattct ctactgcctt ccttctgaga acagc    95

<210> SEQ ID NO 86
<211> LENGTH: 93
<212> TYPE: DNA
<213> ORGANISM: Homo sapiens

<400> SEQUENCE: 86
gctgttcagt gatgaggcct ggaatgtgcg ctgggcacag cgcccgagac agactgcgga    60
accgttcctt gttgccttcc ttctgagaac agc    93

<210> SEQ ID NO 87
<211> LENGTH: 78
<212> TYPE: DNA
<213> ORGANISM: Homo sapiens

<400> SEQUENCE: 87
gccatatgat gttttctttt cgaaaggtga gcgctttgcg cagtgatgac cctcatctat    60
cacccttgac tgatggct    78

<210> SEQ ID NO 88
<211> LENGTH: 75
<212> TYPE: DNA
<213> ORGANISM: Homo sapiens

<400> SEQUENCE: 88
gactggcaag gatgatacac acttgccctc acttagacta tagttcactg atgagagcat    60
tgttctgagc cagtc    75

<210> SEQ ID NO 89
<211> LENGTH: 86
<212> TYPE: DNA
<213> ORGANISM: Homo sapiens

<400> SEQUENCE: 89
gatcacggtg atggctgacc agggctccct gacctataca ggcctctgct atggggtga    60 tggccagtcc tggtgtctga gtgatt    86

<210> SEQ ID NO 90
<211> LENGTH: 76
<212> TYPE: DNA
<213> ORGANISM: Homo sapiens

```
<400> SEQUENCE: 90
acaatgatga cttaaattac tttttgccgt ttacccagct gaggttgtct ttgaagaaat      60
aattttaaga ctgaga                                                     76

<210> SEQ ID NO 91
<211> LENGTH: 97
<212> TYPE: DNA
<213> ORGANISM: Homo sapiens

<400> SEQUENCE: 91
ccggggcctc catgatgtcc agcactgggc tccgactgcc actgaggaca cggtgccccc      60 cgggacctttt gacacccggg ggtctgaggg gccctgg                             97

<210> SEQ ID NO 92
<211> LENGTH: 97
<212> TYPE: DNA
<213> ORGANISM: Homo sapiens

<400> SEQUENCE: 92
ttggggaccc cgtgatgtcc agcactgggc tctgactgcc cctgaggaca cggtgcaccc      60
cgggaccttt gacatccggg gttctgaggg gccccac                              97

<210> SEQ ID NO 93
<211> LENGTH: 97
<212> TYPE: DNA
<213> ORGANISM: Homo sapiens

<400> SEQUENCE: 93
ctggggctcc catgatgtcc agcactgggc tctgatcacc cctgaggaca cagtgcaccc      60
caggaccttt gacacctggg ggtctgaggg gccccag                              97

<210> SEQ ID NO 94
<211> LENGTH: 114
<212> TYPE: DNA
<213> ORGANISM: Homo sapiens

<400> SEQUENCE: 94
actgaggaat gatgacaaga aaaggccgaa ttgcagtgtc tccatcagca gtttgctctc      60
catgggcaca cgatgacaaa atatcctgaa gcgaaccact agtctgacct cagt          114

<210> SEQ ID NO 95
<211> LENGTH: 107
<212> TYPE: DNA
<213> ORGANISM: Homo sapiens

<400> SEQUENCE: 95
aagttttcta agtgtctaat gatgaatttc atagggcaga ttctgaggtg aaaatttaat      60
tcatcactga tactcctact gtggaatctg aagacacttg aaaacgt                  107

<210> SEQ ID NO 96
<211> LENGTH: 92
<212> TYPE: DNA
<213> ORGANISM: Homo sapiens

<400> SEQUENCE: 96
tagagaagtc aatgatggtt ttattcatat cgtctgaacc tgtctgaagc atctcagtga      60
tgcaatctct gtgtggttct gagacttctc ca                                   92
```

```
<210> SEQ ID NO 97
<211> LENGTH: 86
<212> TYPE: DNA
<213> ORGANISM: Homo sapiens

<400> SEQUENCE: 97
aagagccaat gatgttttta ttcaaaatgt ctgaacctgt ctgaagcatc ccagtgatgc    60
aacttctgtg tgatactgag gctttt                                        86

<210> SEQ ID NO 98
<211> LENGTH: 89
<212> TYPE: DNA
<213> ORGANISM: Homo sapiens

<400> SEQUENCE: 98
tggtgctgtg atgatgcctt aatattgtgg tttcgactca ctgagagtaa aatgaggacc    60
tacaattcct tggctgtgtc tgagcaccc                                     89

<210> SEQ ID NO 99
<211> LENGTH: 74
<212> TYPE: DNA
<213> ORGANISM: Homo sapiens

<400> SEQUENCE: 99
tggccaagga tgagaactct aatctgattt tatgtgcttc tgctgtgatg gattaaagga    60
tttacctgag gcca                                                     74

<210> SEQ ID NO 100
<211> LENGTH: 137
<212> TYPE: DNA
<213> ORGANISM: Homo sapiens

<400> SEQUENCE: 100
caggctgtga tgattggcgc aggggtacgg acctcagctg agtcatggga gctgaatgta    60
tgtgtttctc ctttgtcctg catgtggcag gctgatgggg agcacttaca tgagactgtt   120
gcctcaatct gagcctg                                                  137

<210> SEQ ID NO 101
<211> LENGTH: 63
<212> TYPE: DNA
<213> ORGANISM: Homo sapiens

<400> SEQUENCE: 101
gcggtgatga ccccaacatg ccatctgagt gtcggtgctg aaatccagag gctgtttctg    60
agc                                                                 63

<210> SEQ ID NO 102
<211> LENGTH: 72
<212> TYPE: DNA
<213> ORGANISM: Homo sapiens

<400> SEQUENCE: 102
cctggtgatg acagatggca ttgtcagcca atccccaagt gggagtgagg acatgtcctg    60
caattctgaa gg                                                       72

<210> SEQ ID NO 103
<211> LENGTH: 72
<212> TYPE: DNA
<213> ORGANISM: Homo sapiens
```

```
<400> SEQUENCE: 103
cctggtgatg acagacgaca ttgtcagcca atccccatgt ggtagtgagg acatgtcctg    60
cagttctgaa gg                                                        72

<210> SEQ ID NO 104
<211> LENGTH: 142
<212> TYPE: DNA
<213> ORGANISM: Homo sapiens

<400> SEQUENCE: 104
ttgcccgatg attataaaaa gacgcgttat taagaggact ttatgctgga gttcttgacg    60
tttttctctc ttttctatac ttcttttct ttctttgaat gtccagcgtc ctgtgagcga    120
agattatgag atatgagggc aa                                             142

<210> SEQ ID NO 105
<211> LENGTH: 67
<212> TYPE: DNA
<213> ORGANISM: Homo sapiens

<400> SEQUENCE: 105
gagttatgat gtgtgtaaat cctattccat tgctgaaatg cagtgtggaa cacaatgaac    60
tgaactc                                                              67

<210> SEQ ID NO 106
<211> LENGTH: 80
<212> TYPE: DNA
<213> ORGANISM: Homo sapiens

<400> SEQUENCE: 106
actggtccag gatgaaacct aatttgagtg gacatccatg gatgagaaat gcggatatgg    60
gactgagacc agctcctagg                                                80

<210> SEQ ID NO 107
<211> LENGTH: 76
<212> TYPE: DNA
<213> ORGANISM: Homo sapiens

<400> SEQUENCE: 107
gctgtacatg atgacaactg gctccctcta ctgaactgcc atgaggaaac tgccatgtca    60
cccttctgat tacagc                                                    76

<210> SEQ ID NO 108
<211> LENGTH: 73
<212> TYPE: DNA
<213> ORGANISM: Homo sapiens

<400> SEQUENCE: 108
gtttgaatga tgactttaat tgtcggatac cccttcactc cttttatgag tgaaacataa    60
gagtctgaca aac                                                       73

<210> SEQ ID NO 109
<211> LENGTH: 72
<212> TYPE: DNA
<213> ORGANISM: Homo sapiens

<400> SEQUENCE: 109
agcttaatga tgactgtttt ttttgattgc ttgaagcaat gtgaaaaaca catttcaccg    60
gctctgaaag ct                                                        72
```

<210> SEQ ID NO 110
<211> LENGTH: 91
<212> TYPE: DNA
<213> ORGANISM: Homo sapiens

<400> SEQUENCE: 110
ttgtctggca atgatgaccc acttgccctc actgagaaca aagttcggta atgagaatct    60
ttgttaatgg actcaagttc tgagccagac a                                  91

<210> SEQ ID NO 111
<211> LENGTH: 91
<212> TYPE: DNA
<213> ORGANISM: Homo sapiens

<400> SEQUENCE: 111
ttgtctggca atgatgaccc acttgccctc actgagaaca aagttcggta atgagaatct    60
ttgttaatgg actcaagttc tgagccagac a                                  91

<210> SEQ ID NO 112
<211> LENGTH: 80
<212> TYPE: DNA
<213> ORGANISM: Homo sapiens

<400> SEQUENCE: 112
ggcctgctgt gatgacattc caattaaagc acgtgttaga ctgctgacgc gggtgatgcg    60
aactggagtc tgagcctgcc                                               80

<210> SEQ ID NO 113
<211> LENGTH: 85
<212> TYPE: DNA
<213> ORGANISM: Homo sapiens

<400> SEQUENCE: 113
cccctatctc tcatgatgaa cacatatgcc tctgagctgc tgtgatttct ggcttcaaag    60
taaacgctct gaagaagaga tgggg                                         85

<210> SEQ ID NO 114
<211> LENGTH: 79
<212> TYPE: DNA
<213> ORGANISM: Homo sapiens

<400> SEQUENCE: 114
ccacatgcgg ctgatgacag cacttctgct gagacgctgt gattgctctg tccaaagtaa    60
acgccctgac gcactgtgg                                                79

<210> SEQ ID NO 115
<211> LENGTH: 75
<212> TYPE: DNA
<213> ORGANISM: Homo sapiens

<400> SEQUENCE: 115
ggttcatgat gacacaggac cttgtctgaa cataatgatt tcaaaatttg agcttaaaaa    60
tgacactctg aaatc                                                    75

<210> SEQ ID NO 116
<211> LENGTH: 71
<212> TYPE: DNA
<213> ORGANISM: Homo sapiens

<400> SEQUENCE: 116
gcttaatgat gagaatcatt atttcttgaa ttggatgaca ctttccattc ctgcaaaggg    60
agcgtgaggt c    71

<210> SEQ ID NO 117
<211> LENGTH: 67
<212> TYPE: DNA
<213> ORGANISM: Homo sapiens

<400> SEQUENCE: 117
ggatcgatga tgagaataat tgtctgagga tgctgaggga ctcattccag atgtcaatct    60
gaggtcc    67

<210> SEQ ID NO 118
<211> LENGTH: 67
<212> TYPE: DNA
<213> ORGANISM: Homo sapiens

<400> SEQUENCE: 118
ggatcgatga tgagaataat tgtctgagga tgctgaggga ctcattccag atgtcaatct    60
gaggtcc    67

<210> SEQ ID NO 119
<211> LENGTH: 75
<212> TYPE: DNA
<213> ORGANISM: Homo sapiens

<400> SEQUENCE: 119
ttgcagtgat gacttgcgaa tcaaatctgt caatcccctg agtgcaatca ctgatgtctc    60
catgtctctg agcaa    75

<210> SEQ ID NO 120
<211> LENGTH: 94
<212> TYPE: DNA
<213> ORGANISM: Homo sapiens

<400> SEQUENCE: 120
cagcctgaaa tgatgactct ttaaaaaatt tcatgtctct tctctgacat ttttctctgg    60
acacagtttt tgccttatga atctgatcag gctg    94

<210> SEQ ID NO 121
<211> LENGTH: 87
<212> TYPE: DNA
<213> ORGANISM: Homo sapiens

<400> SEQUENCE: 121
cagcctgaag tgatgattca cattcatgtc tcttctctga taaattcttg aagaaaattt    60
ttgtgtgtct gatcaggcct ctagagg    87

<210> SEQ ID NO 122
<211> LENGTH: 77
<212> TYPE: DNA
<213> ORGANISM: Homo sapiens

<400> SEQUENCE: 122
tggaccaatg atgagacagt gtttatgaac aaagatcat gattaatcca gttctgcaca    60
aaacactgag gtccatt    77

<210> SEQ ID NO 123
<211> LENGTH: 70
<212> TYPE: DNA
<213> ORGANISM: Homo sapiens

<400> SEQUENCE: 123
aaagtgagtg atgaatagtt ctgtggcata tgaatcatta attttgatta aaccctaaac    60
tctgaagtcc                                                          70

<210> SEQ ID NO 124
<211> LENGTH: 71
<212> TYPE: DNA
<213> ORGANISM: Homo sapiens

<400> SEQUENCE: 124
atagccaatc attagtattc tgagctgtag gaatcaaaga ttttgattag attctgtaac    60
tcagaggttt a                                                        71

<210> SEQ ID NO 125
<211> LENGTH: 71
<212> TYPE: DNA
<213> ORGANISM: Homo sapiens

<400> SEQUENCE: 125
tagaccaatg atgagtattc tggggtgtct gaatcaatga ttttgattaa accctgtaac    60
tctgaggtcc a                                                        71

<210> SEQ ID NO 126
<211> LENGTH: 74
<212> TYPE: DNA
<213> ORGANISM: Homo sapiens

<400> SEQUENCE: 126
tggaccaatg atgagtacca tggggtatct gaaacaggat ttttgattaa acccatatgc    60
aattctgagg tcca                                                     74

<210> SEQ ID NO 127
<211> LENGTH: 77
<212> TYPE: DNA
<213> ORGANISM: Homo sapiens

<400> SEQUENCE: 127
tggatcaatg atgagtattg gtggaggtgt ctgaatcaac acttttgatt aagccctctg    60
tgtaactctg agatctg                                                  77

<210> SEQ ID NO 128
<211> LENGTH: 74
<212> TYPE: DNA
<213> ORGANISM: Homo sapiens

<400> SEQUENCE: 128
tggaccagtg atgaatatca tggggtttct gaaacaacat ttttgattaa acccatctgc    60
aactctgagg tcca                                                     74

<210> SEQ ID NO 129
<211> LENGTH: 76
<212> TYPE: DNA
<213> ORGANISM: Homo sapiens

<400> SEQUENCE: 129

-continued

```
tggatcaatg atgagtatgc gtggggcatc tgaatcaaat attctgatta taccctgtct    60
gtatctctga ggtcca                                                    76

<210> SEQ ID NO 130
<211> LENGTH: 73
<212> TYPE: DNA
<213> ORGANISM: Homo sapiens

<400> SEQUENCE: 130
tggaccaatg atgagattgg agggtgtctg aatcaaaaat tttgattaaa gccatctgta    60
actctgaggt cca                                                       73

<210> SEQ ID NO 131
<211> LENGTH: 71
<212> TYPE: DNA
<213> ORGANISM: Homo sapiens

<400> SEQUENCE: 131
tggatcaatg atgagtaccc tggggtgtct gaatcttgga ttttgattaa accctataac    60
tctgaggtcc a                                                         71

<210> SEQ ID NO 132
<211> LENGTH: 71
<212> TYPE: DNA
<213> ORGANISM: Homo sapiens

<400> SEQUENCE: 132
tggacctatg atgatgactg gtggcgtatg agtcattgac ggtgaataca ggtctggaag    60
tctgaggtcc a                                                         71

<210> SEQ ID NO 133
<211> LENGTH: 77
<212> TYPE: DNA
<213> ORGANISM: Homo sapiens

<400> SEQUENCE: 133
gggaccaatg ataatgactg ttggggtatg agtcagtgag gttgaataac agtttgtatc    60
tggaaatctg aggtcca                                                   77

<210> SEQ ID NO 134
<211> LENGTH: 74
<212> TYPE: DNA
<213> ORGANISM: Homo sapiens

<400> SEQUENCE: 134
tggaccaatg atgaccactg gtggcgtttg agtcatggac gatgaatact acgtgtctga    60
aactctgagg tcca                                                      74

<210> SEQ ID NO 135
<211> LENGTH: 74
<212> TYPE: DNA
<213> ORGANISM: Homo sapiens

<400> SEQUENCE: 135
tgagccagtg atgaaaactg gtggcataga agtcaaggat gctgaataat gtgtgtctag    60
aactctgagg ttca                                                      74

<210> SEQ ID NO 136
<211> LENGTH: 69
```

<212> TYPE: DNA
<213> ORGANISM: Homo sapiens

<400> SEQUENCE: 136

```
tggattgatg atgaccactg gtggcctatg agtcatacaa tgaatacgtg tctagaactc    60
tgaggtcca                                                           69
```

<210> SEQ ID NO 137
<211> LENGTH: 71
<212> TYPE: DNA
<213> ORGANISM: Homo sapiens

<400> SEQUENCE: 137

```
tggatcaatg atgtccactg gtggcgtata aatcatattt ggtgaatata tgtctggaac    60
tctgaggtcc a                                                        71
```

<210> SEQ ID NO 138
<211> LENGTH: 76
<212> TYPE: DNA
<213> ORGANISM: Homo sapiens

<400> SEQUENCE: 138

```
tgaactagtg gtgatggctt gtggcatatt tagtcacaga tgatgaataa atacatgcct    60
gagactctga ggttag                                                   76
```

<210> SEQ ID NO 139
<211> LENGTH: 71
<212> TYPE: DNA
<213> ORGANISM: Homo sapiens

<400> SEQUENCE: 139

```
tgatgatatg atggccactg gtggcttatg agtcttatac agtgaataca tgtttgaaac    60
tctgaggtct g                                                        71
```

<210> SEQ ID NO 140
<211> LENGTH: 71
<212> TYPE: DNA
<213> ORGANISM: Homo sapiens

<400> SEQUENCE: 140

```
tggatcgatg atgactgctg gtggcgtatg agtcttacat gatgaatacg tgtctggaac    60
tctgaggtcc a                                                        71
```

<210> SEQ ID NO 141
<211> LENGTH: 71
<212> TYPE: DNA
<213> ORGANISM: Homo sapiens

<400> SEQUENCE: 141

```
aagatcaatg atgactactg ttagtgtatg agttacacat gatgaataca tgtctgaaac    60
tctgaggtcc a                                                        71
```

<210> SEQ ID NO 142
<211> LENGTH: 74
<212> TYPE: DNA
<213> ORGANISM: Homo sapiens

<400> SEQUENCE: 142

```
tggaccagtg atggtgactg gtggtgtgtg agtcatgcac agtgaatatc atgtgtctgg    60
```
aactctgagg tcca                                                74

<210> SEQ ID NO 143
<211> LENGTH: 74
<212> TYPE: DNA
<213> ORGANISM: Homo sapiens

<400> SEQUENCE: 143
tggaccaatg atgacaaata ccggcgtatg agtcttggat gatgaataat acgtgtctgg    60
aactctgagg tcca                                                74

<210> SEQ ID NO 144
<211> LENGTH: 73
<212> TYPE: DNA
<213> ORGANISM: Homo sapiens

<400> SEQUENCE: 144
tggaccagtg atgaccactg gtggcatatg agtcatacac atgaacacca tgtttctaga    60
actctgaggt cca                                                 73

<210> SEQ ID NO 145
<211> LENGTH: 74
<212> TYPE: DNA
<213> ORGANISM: Homo sapiens

<400> SEQUENCE: 145
tggaccaatg atgacaactg ccggcgtatg agtgttgggt gatgaataat acgtgtctag    60
aactctgagg tcca                                                74

<210> SEQ ID NO 146
<211> LENGTH: 71
<212> TYPE: DNA
<213> ORGANISM: Homo sapiens

<400> SEQUENCE: 146
tggatcgatg atgaccactg gtggcgtatg agtcatacat gatgaatatg tgtctggaac    60
tctgaggtcc t                                                   71

<210> SEQ ID NO 147
<211> LENGTH: 69
<212> TYPE: DNA
<213> ORGANISM: Homo sapiens

<400> SEQUENCE: 147
tggaccaatt atgactactg gtgtgagtca cgcataatga acaccacgtg tctggaactc    60
tgaggtcca                                                      69

<210> SEQ ID NO 148
<211> LENGTH: 74
<212> TYPE: DNA
<213> ORGANISM: Homo sapiens

<400> SEQUENCE: 148
tggaccaatg atgacaaatg gtggcattgg agttatggac gatgaatgat atgtgtctga    60
aactctgagg tcca                                                74

<210> SEQ ID NO 149
<211> LENGTH: 71
<212> TYPE: DNA
<213> ORGANISM: Homo sapiens

<400> SEQUENCE: 149
tagatcagtg atgactactg ttggtgtatg agtcatatac gatgaataca tgtctgaaat    60
tctgaggtcc a                                                         71

<210> SEQ ID NO 150
<211> LENGTH: 74
<212> TYPE: DNA
<213> ORGANISM: Homo sapiens

<400> SEQUENCE: 150
tggatcaatg ataaaacttg ctggcatatg aatcttggat aatggatgat acgtgtgtgg    60
aactctgagg tcca                                                      74

<210> SEQ ID NO 151
<211> LENGTH: 71
<212> TYPE: DNA
<213> ORGANISM: Homo sapiens

<400> SEQUENCE: 151
tggatcgatg atgactactg gtggcgtatg agtcatctac agtgaatacg tctctggaac    60
tctgaggtct g                                                         71

<210> SEQ ID NO 152
<211> LENGTH: 71
<212> TYPE: DNA
<213> ORGANISM: Homo sapiens

<400> SEQUENCE: 152
tggatcaatg atgaccactg gtggcgtatg agtcatatgt gatgaatacg tgtctggaac    60
tctgaggtcc a                                                         71

<210> SEQ ID NO 153
<211> LENGTH: 71
<212> TYPE: DNA
<213> ORGANISM: Homo sapiens

<400> SEQUENCE: 153
tggatcgatg atgactaccg gtggcgtatg agtcatatgt gatgaatacg tgtttggaac    60
tctgaggtcc a                                                         71

<210> SEQ ID NO 154
<211> LENGTH: 71
<212> TYPE: DNA
<213> ORGANISM: Homo sapiens

<400> SEQUENCE: 154
tggatcgatg atgactactg gtggcgtatg agtcatagac aatgaatacg tgtctggaac    60
tctgaggtcc a                                                         71

<210> SEQ ID NO 155
<211> LENGTH: 71
<212> TYPE: DNA
<213> ORGANISM: Homo sapiens

<400> SEQUENCE: 155
tggatcgatg gtgactgttg atggcatatg actcacatat gatgagtacg tatctggaac    60
tctgaggtct g                                                         71

```
<210> SEQ ID NO 156
<211> LENGTH: 71
<212> TYPE: DNA
<213> ORGANISM: Homo sapiens

<400> SEQUENCE: 156
tggatcgatg atgactactg gtggcgtatg agtctttttgc gatgaatacg tgtctagaac      60
tctgaggtcc g                                                           71

<210> SEQ ID NO 157
<211> LENGTH: 71
<212> TYPE: DNA
<213> ORGANISM: Homo sapiens

<400> SEQUENCE: 157
tggatcgatg atgagcactg gtggagtatg agtcacatac gatgaatacg tgtctggaac      60
tctgaggtcc a                                                           71

<210> SEQ ID NO 158
<211> LENGTH: 69
<212> TYPE: DNA
<213> ORGANISM: Homo sapiens

<400> SEQUENCE: 158
tggttcagtg ttgactactg gtgtcgtgtg agtcatacaa tgaatacatg tctggaactc      60
tgaggccca                                                              69

<210> SEQ ID NO 159
<211> LENGTH: 71
<212> TYPE: DNA
<213> ORGANISM: Homo sapiens

<400> SEQUENCE: 159
tggatcgatg atgactgctg gtggcgtatg agtcatatgc gatgaatacg tgtctagaac      60
tctgaggtcc a                                                           71

<210> SEQ ID NO 160
<211> LENGTH: 69
<212> TYPE: DNA
<213> ORGANISM: Homo sapiens

<400> SEQUENCE: 160
tggatcgatg atgactactg gtagcatgag tcatatacag tgaatacatg tctggaactc      60
tgaggtctg                                                              69

<210> SEQ ID NO 161
<211> LENGTH: 71
<212> TYPE: DNA
<213> ORGANISM: Homo sapiens

<400> SEQUENCE: 161
tggatcaatc atgactactg gtattggatg ggtcttcgtc agtgaatgcc tatctggaac      60
tctgaggtcc a                                                           71

<210> SEQ ID NO 162
<211> LENGTH: 74
<212> TYPE: DNA
<213> ORGANISM: Homo sapiens

<400> SEQUENCE: 162
```
tgagcaagcg atgacagccg gtggtgtgtg agtcatggag gatgaatact aagtgcctgg    60
aactctgagg ttca                                                      74

<210> SEQ ID NO 163
<211> LENGTH: 97
<212> TYPE: DNA
<213> ORGANISM: Homo sapiens

<400> SEQUENCE: 163
tggatcgatg atgagtcccc tataaaaaca ttccttggaa aagctgaaca aaatgagtga    60
gaactcataa cgtcattctc atcggaactg aggtcca                             97

<210> SEQ ID NO 164
<211> LENGTH: 97
<212> TYPE: DNA
<213> ORGANISM: Homo sapiens

<400> SEQUENCE: 164
tggatcgatg atgagtcccc aaaaaaaaca ttccttggaa aagctgaaca aaatgagtga    60
aaactcatac cgtcattctc atcggaactg aggtcca                             97

<210> SEQ ID NO 165
<211> LENGTH: 97
<212> TYPE: DNA
<213> ORGANISM: Homo sapiens

<400> SEQUENCE: 165
tggatcgatg atgagtcccc cataaaaaca ttccttggaa aagctgaaca aaatgagtga    60
gaactcatac cgtcgttctc atcggaactg aggtcca                             97

<210> SEQ ID NO 166
<211> LENGTH: 98
<212> TYPE: DNA
<213> ORGANISM: Homo sapiens

<400> SEQUENCE: 166
tggatcgatg atgagtcccc ccaaaaaaac attccttgga aaagctgaac aaaatgagtg    60
aaaactcata ccgtcgttct cagcggaact gaggtcca                            98

<210> SEQ ID NO 167
<211> LENGTH: 97
<212> TYPE: DNA
<213> ORGANISM: Homo sapiens

<400> SEQUENCE: 167
tggatcgatg atgagtcccc cataaaaaca ttccttggaa aagctgaaca aaatgagtga    60
gaactcatac cgtcgttctc atcagaactg aggtcca                             97

<210> SEQ ID NO 168
<211> LENGTH: 97
<212> TYPE: DNA
<213> ORGANISM: Homo sapiens

<400> SEQUENCE: 168
tggatcgatg atgagtcccc cataaaaaca ttccttggaa aagctgaaca aaatgagtga    60
gaactcatac cgtcgttctc atcagaactg aggtcca                             97

<210> SEQ ID NO 169

```
<211> LENGTH: 97
<212> TYPE: DNA
<213> ORGANISM: Homo sapiens

<400> SEQUENCE: 169
tggatcgatg atgagtcctc caaaaaaaca ttccttggaa aagctgaaca aaatgagtga      60
gaactcatac cgtcgttctc atcggaactg aggtcca                              97

<210> SEQ ID NO 170
<211> LENGTH: 97
<212> TYPE: DNA
<213> ORGANISM: Homo sapiens

<400> SEQUENCE: 170
tggatcgatg atgagtcccc cataaaaaca ttccttggaa aagctgaaca aaatgagtga      60
gaactcatac cgtcgttctc atcggaactg aggtcca                              97

<210> SEQ ID NO 171
<211> LENGTH: 104
<212> TYPE: DNA
<213> ORGANISM: Homo sapiens

<400> SEQUENCE: 171
taggttgatg atgacttaca tatatacgtt ttttttttt tttggaaag gtgaacaaaa        60 tgagtgaaaa ctcagtacca tcatcctcat ctaactgagg tcca                      104

<210> SEQ ID NO 172
<211> LENGTH: 94
<212> TYPE: DNA
<213> ORGANISM: Homo sapiens

<400> SEQUENCE: 172
tggatcaatg atgacttcca tacgtgggtt ccttggaaag ttgaacaaaa tgagtgaaaa      60
ctttatactg tcatcctctt caaactgagg tcca                                 94

<210> SEQ ID NO 173
<211> LENGTH: 94
<212> TYPE: DNA
<213> ORGANISM: Homo sapiens

<400> SEQUENCE: 173
tggatcaatg atgacttcca tatatacatt ccttggaaag ctgaataaaa tgaatgaaaa      60
ctctatacca tcatcctcat tgaactgagg tccc                                 94

<210> SEQ ID NO 174
<211> LENGTH: 94
<212> TYPE: DNA
<213> ORGANISM: Homo sapiens

<400> SEQUENCE: 174
tggaccaatg atgacttcca tacatgcatt ccttggaaag ctgaacaaaa tgagtgggaa      60
ctctgtacta tcatcttagt tgaactgagg tcca                                 94

<210> SEQ ID NO 175
<211> LENGTH: 94
<212> TYPE: DNA
<213> ORGANISM: Homo sapiens

<400> SEQUENCE: 175
tggatcgatg atgacttcca tatatacatt ccttggaaag ctgaacaaaa tgagtgaaaa      60
```
ctctataccg tcattctcgt cgaactgagg tcca        94

<210> SEQ ID NO 176
<211> LENGTH: 94
<212> TYPE: DNA
<213> ORGANISM: Homo sapiens

<400> SEQUENCE: 176
tggatcgatg atgacttcca tatatacatt ccttggaaag ctgaacaaaa tgagtgaaaa        60
ctctataccg tcatcctcgt caaactgagg tcca        94

<210> SEQ ID NO 177
<211> LENGTH: 94
<212> TYPE: DNA
<213> ORGANISM: Homo sapiens

<400> SEQUENCE: 177
tggatcgatg atgactttca tacatgcatt ccttggaaag ctgaacaaaa tgagtgaaaa        60
ctctataccg tcatcctcgt cgaactgagg tcca        94

<210> SEQ ID NO 178
<211> LENGTH: 94
<212> TYPE: DNA
<213> ORGANISM: Homo sapiens

<400> SEQUENCE: 178
tggatcgatg atgacttcca tatatacatt ccttggaaag ctgaacaaaa tgagtgaaaa        60
ctctataccg tcatcctcgt cgaactgagg tcca        94

<210> SEQ ID NO 179
<211> LENGTH: 94
<212> TYPE: DNA
<213> ORGANISM: Homo sapiens

<400> SEQUENCE: 179
tggatcgatg atgacttcct tatatacatt ccttggaaag ctgaacaaaa tgagtgaaaa        60
ctctataccg tcatcctcgt cgaactgagg tcca        94

<210> SEQ ID NO 180
<211> LENGTH: 94
<212> TYPE: DNA
<213> ORGANISM: Homo sapiens

<400> SEQUENCE: 180
tggatcgatg atgacttcca tatatacatt ccttggaaag ctgaacaaaa tgagtgaaaa        60
ctctataccg tcatcctcgt cgaactgagg tcca        94

<210> SEQ ID NO 181
<211> LENGTH: 94
<212> TYPE: DNA
<213> ORGANISM: Homo sapiens

<400> SEQUENCE: 181
tggatcgatg atgacttcca tatatacatt ccttggaaag ctgaacaaaa tgagtgaaaa        60
ctctatactg tcatcctcgt cgaactgagg tcca        94

<210> SEQ ID NO 182
<211> LENGTH: 94
<212> TYPE: DNA

<213> ORGANISM: Homo sapiens

<400> SEQUENCE: 182
tggatcgatg atgacttcca catatacatt ccttggaaag ctgaacaaaa tgagtgaaaa    60
ctctataccg tcatcctcgt cgaactgagg tcca                              94

<210> SEQ ID NO 183
<211> LENGTH: 94
<212> TYPE: DNA
<213> ORGANISM: Homo sapiens

<400> SEQUENCE: 183
tggatcgatg atgacttcca tatgtacatt ccttggaaag ctgaacaaaa tgagtgaaaa    60
ctctataccg tcatcctcgt cgaactgagg tcca                              94

<210> SEQ ID NO 184
<211> LENGTH: 94
<212> TYPE: DNA
<213> ORGANISM: Homo sapiens

<400> SEQUENCE: 184
tggatcgatg atgacctcaa tacatgcatt ccttggaaag ctgaacaaaa tgagtgaaaa    60
ctctataccg tcgtcctcgt caaactgagg tcca                              94

<210> SEQ ID NO 185
<211> LENGTH: 94
<212> TYPE: DNA
<213> ORGANISM: Homo sapiens

<400> SEQUENCE: 185
tggatcgatg atgactttta tacatgcatt ccttggaaag ctgaacaaaa tgagtgaaaa    60
ctctataccg tcatcttcgt tgaactgagg tcca                              94

<210> SEQ ID NO 186
<211> LENGTH: 94
<212> TYPE: DNA
<213> ORGANISM: Homo sapiens

<400> SEQUENCE: 186
tggatcgatg atgactttaa aatggatctc atcggaatct gaacaaaatg agtgaccaaa    60
tcacttctgt gccacttctg tgagctgagg tcca                              94

<210> SEQ ID NO 187
<211> LENGTH: 98
<212> TYPE: DNA
<213> ORGANISM: Homo sapiens

<400> SEQUENCE: 187
tggatcgatg atgactataa aaaaaatgga tctcatcgga atctgaacaa aatgagtgac    60
caaatcattt ctgtgccact tctgtgagct gaggtcca                          98

<210> SEQ ID NO 188
<211> LENGTH: 94
<212> TYPE: DNA
<213> ORGANISM: Homo sapiens

<400> SEQUENCE: 188
tggatcgatg atgacttaaa gatttatcta atttaaatct gaacaaaatg agtgaccaaa    60
acacttctgt accacttctg tgagctgagg tcca                              94

<210> SEQ ID NO 189
<211> LENGTH: 93
<212> TYPE: DNA
<213> ORGANISM: Homo sapiens

<400> SEQUENCE: 189
tggatggatg acgacttaaa aatgaatctc gttggaatct gagcaaaacg agtgagcaaa        60
ccacttctgt gcagttctgt gaactgaggt caa                                     93

<210> SEQ ID NO 190
<211> LENGTH: 85
<212> TYPE: DNA
<213> ORGANISM: Homo sapiens

<400> SEQUENCE: 190
tggatcgatg atgacttaaa aaaatggaaa ccttggaaat ctgaacaaaa tgagtgacca        60
agacacttct gtgagctgag gtcca                                              85

<210> SEQ ID NO 191
<211> LENGTH: 98
<212> TYPE: DNA
<213> ORGANISM: Homo sapiens

<400> SEQUENCE: 191
tggatcgatg atgagtcctc caaaaaaaac attccttgga aaagctgaac aaaatgagtg        60
aaaactcata ccgtcattct catcggaact gaggtcca                                98

<210> SEQ ID NO 192
<211> LENGTH: 76
<212> TYPE: DNA
<213> ORGANISM: Homo sapiens

<400> SEQUENCE: 192
gccaaatgat gtttatttga aacaggagca cctcagtgca aggacgactc ttatctatca        60
cccatgactg atggct                                                        76

<210> SEQ ID NO 193
<211> LENGTH: 136
<212> TYPE: DNA
<213> ORGANISM: Homo sapiens

<400> SEQUENCE: 193
atcgtcaggt gggataatcc ttacctgttc ctcctccgga gggcagatta gaacatgatg        60
attggagatg catgaaacgt gattaacgtc tctgcgtaat caggacttgc aacaccctga       120
ttgctcctgt ctgatt                                                       136

<210> SEQ ID NO 194
<211> LENGTH: 82
<212> TYPE: DNA
<213> ORGANISM: Homo sapiens

<400> SEQUENCE: 194
gctggattaa tgatgagata taaccttgac tgaagctgat gatgagtttg tataattaag        60
caggattact ctgagatcca gc                                                 82

<210> SEQ ID NO 195
<211> LENGTH: 90
<212> TYPE: DNA

<213> ORGANISM: Homo sapiens

<400> SEQUENCE: 195
cttagtccag aaaacaatga tgtggtaatt tccaagcaca tatctgatga ttccatgtgg    60
aatttaacta cctgagtttc ctggacaaag    90

<210> SEQ ID NO 196
<211> LENGTH: 79
<212> TYPE: DNA
<213> ORGANISM: Homo sapiens

<400> SEQUENCE: 196
tggaaaagac aatgatgttt tatttccaag cacatatctg agttgtatgt gtggacagca    60
ctgagactga gtctttcca    79

<210> SEQ ID NO 197
<211> LENGTH: 70
<212> TYPE: DNA
<213> ORGANISM: Homo sapiens

<400> SEQUENCE: 197
ggtgaaaatg atgaattctg gggcgctgat tcatgtgact tgaaaaatgc catccatttc    60
ctgattcacc    70

<210> SEQ ID NO 198
<211> LENGTH: 104
<212> TYPE: DNA
<213> ORGANISM: Homo sapiens

<400> SEQUENCE: 198
tggtctcaag gaagggatga tgttccagtt gagactcaag aaaaggattc tgagcctcag    60
agctttgaag gagccacttg gtccctgacc ttcctagagg caaa    104

<210> SEQ ID NO 199
<211> LENGTH: 96
<212> TYPE: DNA
<213> ORGANISM: Homo sapiens

<400> SEQUENCE: 199 accccctggca gccctcctg atgattcttc ttcctgagca cgctcatgat gagcaaactg    60
agcctctaag aagttgactg aaggggctgc ttcccc    96

<210> SEQ ID NO 200
<211> LENGTH: 77
<212> TYPE: DNA
<213> ORGANISM: Homo sapiens

<400> SEQUENCE: 200
agtttgccat gatgaaatgc atgttaagtc cgtgtttcag ctgatcagcc tgattaaaca    60
catgctctga gcagact    77

<210> SEQ ID NO 201
<211> LENGTH: 86
<212> TYPE: DNA
<213> ORGANISM: Homo sapiens

<400> SEQUENCE: 201
tggcaactgt gatgaaagat ttggtctgta tgtaatagat tttattacta aatgaggaca    60
acagtccctc taaactgatg ttgcca    86

<210> SEQ ID NO 202
<211> LENGTH: 70
<212> TYPE: DNA
<213> ORGANISM: Homo sapiens

<400> SEQUENCE: 202
aagtgaaatg atggcaatca tctttcggga ctgacctgaa atgaagagaa tactcattgc     60
tgatcacttg                                                           70

<210> SEQ ID NO 203
<211> LENGTH: 217
<212> TYPE: DNA
<213> ORGANISM: Homo sapiens

<400> SEQUENCE: 203
aagactatac tttcagggat catttctata gtgtgttact agagaagttt ctctgaacgt     60
gtagagcacc gaaaaccacg aggaagagag gtagcgtttt ctcctgagcg tgaagccggc    120
tttctggcgt tgcttggctg caactgccgt cagccattga tgatcgttct tctctccgta    180
ttggggagtg agagggagag aacgcggtct gagtggt                             217

<210> SEQ ID NO 204
<211> LENGTH: 217
<212> TYPE: DNA
<213> ORGANISM: Homo sapiens

<400> SEQUENCE: 204
aagactatac tttcagggat catttctata gtgtgttact agagaagttt ctctgaacgt     60
gtagagcacc gaaaaccccg aggaagagag gtagcgtttt ctcctgagcg tgaagccggc    120
tttctggcgt tgcttggctg caactgccgt cagccattga tgatcgttct tctctccgta    180
ttggggagtg agagggagag aacgcggtct gagtggt                             217

<210> SEQ ID NO 205
<211> LENGTH: 217
<212> TYPE: DNA
<213> ORGANISM: Homo sapiens

<400> SEQUENCE: 205
aagactatac tttcagggat catttctata gtgtgttact agagaagttt ctctgaacgt     60
gtagagcacc gaaaaccccg aggaagagag gtagcgtttt ctcctgagcg tgaagccggc    120
tttctggcgt tgcttggctg caactgccgt cagccattga tgatcgttct tctctccgta    180
ttggggagtg agagggagag aacgcggtct gagtggt                             217

<210> SEQ ID NO 206
<211> LENGTH: 217
<212> TYPE: DNA
<213> ORGANISM: Homo sapiens

<400> SEQUENCE: 206
aagactatac tttcagggat catttctata gtgtgttact agagaagttt ctctgaacgt     60
gtagagcacc gaaaaccacg aggaagagag gtagcgtttt ctcctgaacg tgaagccggc    120
tttctggcgt tgcttggctg caactgccgt cagccattga tgatcgttct tctctccgta    180
ttggggagtg agagggagag aacgcggtct gagtggt                             217

<210> SEQ ID NO 207

```
<211> LENGTH: 217
<212> TYPE: DNA
<213> ORGANISM: Homo sapiens

<400> SEQUENCE: 207
aaggctatac tttcagggat catttctata gtgtgttact agagaagttt ctttgaacgt    60
gtagagcacc gaaaacccccg aggaagagag gtagcgtttt ctcctgagcg tgaagccggc   120
tttctggcgt tgcttggctg caactgccgt cagccattga tgatcgttct tctctccgta   180
ttggggagtg agagggagag aacgcggtct gagtggt                            217

<210> SEQ ID NO 208
<211> LENGTH: 72
<212> TYPE: DNA
<213> ORGANISM: Homo sapiens

<400> SEQUENCE: 208
ggtgcagatg atgacactgt aaagcgacca aagtctgaac aaagtgattg gtacctcgtt    60
gtctgatgca cc                                                       72

<210> SEQ ID NO 209
<211> LENGTH: 74
<212> TYPE: DNA
<213> ORGANISM: Homo sapiens

<400> SEQUENCE: 209
gggtgcaaat gatgcatatg ttagcgacca aagcctgatc tttgctgatt agtcataatt    60
aactgactgc accc                                                     74

<210> SEQ ID NO 210
<211> LENGTH: 73
<212> TYPE: DNA
<213> ORGANISM: Homo sapiens

<400> SEQUENCE: 210
gttcagatga tgaatttaac tgttcaactg ctgaatgata acgggcatga actaaaactt    60
aattctgaca gag                                                      73

<210> SEQ ID NO 211
<211> LENGTH: 71
<212> TYPE: DNA
<213> ORGANISM: Homo sapiens

<400> SEQUENCE: 211
gatgttatga tgatgggcga aatgttcaac tgctctgaag gggctgaatg aaaatggcct    60
ttctgaacat c                                                        71

<210> SEQ ID NO 212
<211> LENGTH: 97
<212> TYPE: DNA
<213> ORGANISM: Homo sapiens

<400> SEQUENCE: 212
atgcgatgat gagtgaagta gagcctgacc tggtattgcc attgcttcac tgttggcttt    60
gaccagggta tgatctctta atcttctctc tgagctg                            97

<210> SEQ ID NO 213
<211> LENGTH: 109
<212> TYPE: DNA
<213> ORGANISM: Homo sapiens
```

<400> SEQUENCE: 213
tcccaatgat gagttgccat gctaatactg agccaccagg tagggcagtg ttgccctggt    60
ttgggtgcca gtgagtttaa caaaacttct cacatgaaga tctgagggg              109

<210> SEQ ID NO 214
<211> LENGTH: 103
<212> TYPE: DNA
<213> ORGANISM: Homo sapiens

<400> SEQUENCE: 214
cccctgtgat gagttgccat gctaatacgg agacaccagg tagggagttt taccctaact    60
tgggtgttgt tgaaataaac tctttctcgt aaatgctgag ggg                    103

<210> SEQ ID NO 215
<211> LENGTH: 148
<212> TYPE: DNA
<213> ORGANISM: Homo sapiens

<400> SEQUENCE: 215
gctctgtgat ggagcccatg cgtgtcatct gagcctctgg cttccctgcc agtgcagccc    60
tggcagtgtc ctacttccca gggctgttgt ctgcctggcg ggaaggtcct gggcaaagga   120
tcagtctttg tactctgaga gcagacta                                    148

<210> SEQ ID NO 216
<211> LENGTH: 84
<212> TYPE: DNA
<213> ORGANISM: Homo sapiens

<400> SEQUENCE: 216
gtgttcaatg atgatttcta tttgtttgcc tgatttcctt ttggataatg aaggcatctt    60
tagtcactac ctcttctgag acac                                         84

<210> SEQ ID NO 217
<211> LENGTH: 90
<212> TYPE: DNA
<213> ORGANISM: Homo sapiens

<400> SEQUENCE: 217
gcctttgcag ctgatgatac agcttctttc cccatcagat cgaccctgtt gatctctaca    60
ctattggcca gttttgtctg atgcattggc                                   90

<210> SEQ ID NO 218
<211> LENGTH: 91
<212> TYPE: DNA
<213> ORGANISM: Homo sapiens

<400> SEQUENCE: 218
gctggcatat atgatgactt agcttttttc cccgacagat cgactatgtt gatctaactt    60
ttctaagcca gtttctgtct gatatgccag c                                 91

<210> SEQ ID NO 219
<211> LENGTH: 79
<212> TYPE: DNA
<213> ORGANISM: Homo sapiens

<400> SEQUENCE: 219
tgtaaatgat gacttcactt ttttccccat cagatcgaca atgctgacgt cttatatttt    60

```
gccagttagt tctgataca                                              79
```

```
<210> SEQ ID NO 220
<211> LENGTH: 104
<212> TYPE: DNA
<213> ORGANISM: Homo sapiens

<400> SEQUENCE: 220
atccttttgt agttcatgag cgtgatgatt gggtgttcat acgcttgtgt gagatgtgcc    60
acccttgaac cttgttacga cgtgggcaca ttacccgtct gacc                   104

<210> SEQ ID NO 221
<211> LENGTH: 126
<212> TYPE: RNA
<213> ORGANISM: Saccharomyces cerevisiae

<400> SEQUENCE: 221
ucacggugau gaaagacugg uuccuuaaca uucgcaguuu ccacgguagg aguacgcuua    60
cgaacccauc guuaguacuc ucggugaccg cucuucuuua gagaccuucc uaggaugucu   120
gaguga                                                             126

<210> SEQ ID NO 222
<211> LENGTH: 102
<212> TYPE: RNA
<213> ORGANISM: Saccharomyces cerevisiae

<400> SEQUENCE: 222
gugaaugaug aauuuaauuc uuuggaccgu guuuaugaug ggaaguaaga cccccgauau    60
gagugacaaa agagaugugg uugacuauca caguaucuga cg                     102

<210> SEQ ID NO 223
<211> LENGTH: 89
<212> TYPE: RNA
<213> ORGANISM: Saccharomyces cerevisiae

<400> SEQUENCE: 223
ucaaaugaug uaauaacaua uuugcuacuu cagauggaac uuugaguucc gaaugagaca    60
uaccaauuau caccaagauc ucugaugaa                                     89

<210> SEQ ID NO 224
<211> LENGTH: 186
<212> TYPE: RNA
<213> ORGANISM: Saccharomyces cerevisiae

<400> SEQUENCE: 224
aacuauuaca gucgaugagg auagguuaua guucaugugu aacaucugug uuuuaaaaua    60 acucaguua uccggggcgu uuuucacaaa guuuguguaa gaugcuuucc ugggucgaug   120
uggauugugc cguggccuuu uucaccaccu uuauagcggu gcuuaacua uuaauaacug   180 aggcug                                                             186

<210> SEQ ID NO 225
<211> LENGTH: 124
<212> TYPE: RNA
<213> ORGANISM: Saccharomyces cerevisiae

<400> SEQUENCE: 225
aggaaguuuu uuccuuuuua uaugaugaau augagugcau uuggcucgag uugcuguuug    60
gcuuuugcca aaucaguaac ggguguggaaa aacucaagcu accuuuuuuu acuuuuaucu  120
```

```
gacc                                                                      124

<210> SEQ ID NO 226
<211> LENGTH: 95
<212> TYPE: RNA
<213> ORGANISM: Saccharomyces cerevisiae

<400> SEQUENCE: 226
cauaaugaug aaaaaaaauu uuaucaaaca guuaucccug ucugaauggg uaauaauagg          60
uaaccucuca uauguugaua uuuguauuuc ugaua                                    95

<210> SEQ ID NO 227
<211> LENGTH: 89
<212> TYPE: RNA
<213> ORGANISM: Saccharomyces cerevisiae

<400> SEQUENCE: 227
uuuuaugaug aaaauccauu guacccaau acauauucga cuagucauug acgaugcugu           60
cguaacuuau caccaucuuu cgacugauu                                           89

<210> SEQ ID NO 228
<211> LENGTH: 95
<212> TYPE: RNA
<213> ORGANISM: Saccharomyces cerevisiae

<400> SEQUENCE: 228
uuuagugaug auacugccga uucuggcauu ccaaaaagug acuagcaaaa uugcgauguu          60
gucaacuuaa auuacaccau cuuucggggc ugaua                                    95

<210> SEQ ID NO 229
<211> LENGTH: 97
<212> TYPE: RNA
<213> ORGANISM: Saccharomyces cerevisiae

<400> SEQUENCE: 229
guaaaugacg agaaaaaagc ugugcaccag ucugaacaug gaugccacaa guacucaggu          60
guccuaugaa gcauuaagua uacccaaauu ucugauc                                  97

<210> SEQ ID NO 230
<211> LENGTH: 110
<212> TYPE: RNA
<213> ORGANISM: Saccharomyces cerevisiae

<400> SEQUENCE: 230
uccccuauga uuaaaaauua uuaaucauau accaauuguu ccgacugaau agugguuaa           60 cuacaugucg acaacccuuu uucguuaagu uucagccuug uaugaggggu                    110

<210> SEQ ID NO 231
<211> LENGTH: 172
<212> TYPE: RNA
<213> ORGANISM: Saccharomyces cerevisiae

<400> SEQUENCE: 231
aaugaccuuc caaguuuuua aaagaauacg augauauuau uugcguuuca aaucgaacaa          60
uucuucucgg agcgaucuga gguuuaaaug gagauagcgg uuccugcgca acccauugau         120
cuuguuacau ucuuaagaau gacaaggacg cuuuuauaaa auucugauuc uu                 172

<210> SEQ ID NO 232
```

```
<211> LENGTH: 99
<212> TYPE: RNA
<213> ORGANISM: Saccharomyces cerevisiae

<400> SEQUENCE: 232
auauaugaug auauccuaua acaacaacaa caugaauuuc uucguccgaa uccuuuauag    60
guggaaacaa acuuugacaa uagcuuuuua acacugaua                          99

<210> SEQ ID NO 233
<211> LENGTH: 112
<212> TYPE: RNA
<213> ORGANISM: Saccharomyces cerevisiae

<400> SEQUENCE: 233
cauaaugaug auuucacuua uaccuauaug uuuuuucugg caucucuaau guuaggaugu    60
gaaguuuaag uacucuccau ucaaugaaua caauuuuuga caauaucuga uu           112

<210> SEQ ID NO 234
<211> LENGTH: 89
<212> TYPE: RNA
<213> ORGANISM: Saccharomyces cerevisiae

<400> SEQUENCE: 234
uagaaugaug aaagagguag caauuugcag cagauuuuuc gugauugaau caaacaaaga    60
uuaaccuuua cagaaccgcu acacugaua                                     89

<210> SEQ ID NO 235
<211> LENGTH: 107
<212> TYPE: RNA
<213> ORGANISM: Saccharomyces cerevisiae

<400> SEQUENCE: 235
uauuaugaug auuuuuuuau auucacacug acuagauug gucucuuuaa cgaaggggcu    60
aauugaugac uacaaaauaa aaaauaacug auuuaaugac ucgaaa                  107

<210> SEQ ID NO 236
<211> LENGTH: 92
<212> TYPE: RNA
<213> ORGANISM: Saccharomyces cerevisiae

<400> SEQUENCE: 236
uacuaugaug aaugacauua gcgugaacaa ucucugauac aaaaucgaaa gauuuuagga    60
uuagaaaaac uuauguugcc uuccuucuga aa                                 92

<210> SEQ ID NO 237
<211> LENGTH: 91
<212> TYPE: RNA
<213> ORGANISM: Saccharomyces cerevisiae

<400> SEQUENCE: 237
uuugaugaug auuacacucc augcuaauca ugaacguguu cgauguaaau uugaauacga    60
ugauuaaaau uguuguuuac gcuuucgaa a                                   91

<210> SEQ ID NO 238
<211> LENGTH: 86
<212> TYPE: RNA
<213> ORGANISM: Saccharomyces cerevisiae

<400> SEQUENCE: 238
uaagaugaug aucaacuuuu uauaucaaua acuuucguuc uacugacugu gaucaaacga    60
```
ucuuguagag aacuuuuacu cugaau         86

<210> SEQ ID NO 239
<211> LENGTH: 98
<212> TYPE: RNA
<213> ORGANISM: Saccharomyces cerevisiae

<400> SEQUENCE: 239
uuauuugaug aauagacacc acaaucgucu uuuuuuauc cggcgaugau uccuuuggaa         60
uaugugccau ggauuacauc augcaucacc aucgauu         98

<210> SEQ ID NO 240
<211> LENGTH: 87
<212> TYPE: RNA
<213> ORGANISM: Saccharomyces cerevisiae

<400> SEQUENCE: 240
uaacaugaug aaaaaauaua uuaacacaga ccuguacuga acuuuucgaa guuuugcaga         60
uaacaauauu gcuuuuuuc ucugacu         87

<210> SEQ ID NO 241
<211> LENGTH: 88
<212> TYPE: RNA
<213> ORGANISM: Saccharomyces cerevisiae

<400> SEQUENCE: 241
aagcgugauu auaaaaaaug auuuaaauau uuuucugagg aaguauaugc aggacauauu         60
gugaauuagg aauucuucgu uuaugauc         88

<210> SEQ ID NO 242
<211> LENGTH: 96
<212> TYPE: RNA
<213> ORGANISM: Saccharomyces cerevisiae

<400> SEQUENCE: 242
cuuuaugaug auauucuuua cgaacuuuua gacguuagac uucgaagga gauuagaccc         60 uccuauggaa gagaaacucg uuaaacuuau cgagu         96

<210> SEQ ID NO 243
<211> LENGTH: 78
<212> TYPE: RNA
<213> ORGANISM: Saccharomyces cerevisiae

<400> SEQUENCE: 243
cuuaaugaug aaaacuauuc cuuauucucg acuagucuuu gacaaugcug ucguuuaauc         60
accaucuuuc ggcugacu         78

<210> SEQ ID NO 244
<211> LENGTH: 103
<212> TYPE: RNA
<213> ORGANISM: Saccharomyces cerevisiae

<400> SEQUENCE: 244
guuaaugaug auaaccaaag augcauaguu caacgauug aacauacuau cgaaaugaag         60
auaaaaauuu ccaucgaaau uagucuuucg cuccuaucug aac         103

<210> SEQ ID NO 245
<211> LENGTH: 89
<212> TYPE: RNA

<213> ORGANISM: Saccharomyces cerevisiae

<400> SEQUENCE: 245

| uacaaugaug auaaaauuua cuauucaguu cugcuucuga accaaaauaa uaggaagaua | 60 |
|---|---|
| accaauuuua ccaaagcuca aaucugauu | 89 |

<210> SEQ ID NO 246
<211> LENGTH: 100
<212> TYPE: RNA
<213> ORGANISM: Saccharomyces cerevisiae

<400> SEQUENCE: 246

| uuuuaugaug aauuuauguu uucaaucuua ucuacauuau cugaauuaau agcuaacaau | 60 |
|---|---|
| aguuauaaug gaagauauac gacuaucaac aauucugaaa | 100 |

<210> SEQ ID NO 247
<211> LENGTH: 255
<212> TYPE: RNA
<213> ORGANISM: Saccharomyces cerevisiae

<400> SEQUENCE: 247

| uuuaaugaug aagauuuuaa uuuuccguug gucuauaaag aacagaagua cuucaaaacu | 60 |
|---|---|
| acuuuuaag accauccuuu uacaguauuu uuucaauauu guaaaacuuc ucauuuacuu | 120 |
| ugugucuuua ugaucucauc guucggugg accauaauca gacgcacggu auacuucguu | 180 |
| ucuguuggag aauauuggga gucuuuuaau gugaugagug gccaacauaa ccuuauaguc | 240 |
| auaguuacac ugauu | 255 |

<210> SEQ ID NO 248
<211> LENGTH: 101
<212> TYPE: RNA
<213> ORGANISM: Saccharomyces cerevisiae

<400> SEQUENCE: 248

| uuguaugaug aggaaccaga uagggacaac agauucucaa gugacgagga acaucuuuua | 60 |
|---|---|
| aagcccaguu uuuaguagag cuuagggcgc cuuuacugac u | 101 |

<210> SEQ ID NO 249
<211> LENGTH: 100
<212> TYPE: RNA
<213> ORGANISM: Saccharomyces cerevisiae

<400> SEQUENCE: 249

| uaaaaugaug auuuuuuuaa acacaauuua ugcuagauag uaucugaaag cauucaaacu | 60 |
|---|---|
| uuaugauuac aguguuucg acaguuuuaa aucucugaac | 100 |

<210> SEQ ID NO 250
<211> LENGTH: 85
<212> TYPE: RNA
<213> ORGANISM: Saccharomyces cerevisiae

<400> SEQUENCE: 250

| ucaaaugaug aaauaccaau gcaacagagu caagcucuga guucaaaaa gaaacaugga | 60 |
|---|---|
| cgagauugcu uuuuuauuac ugacc | 85 |

<210> SEQ ID NO 251
<211> LENGTH: 82
<212> TYPE: RNA
<213> ORGANISM: Saccharomyces cerevisiae

<400> SEQUENCE: 251
uaacaugaug acuaaguugu cgccccaagc ggaucuuuga aaugacugau uuuacaaaca    60
acaaacacug aaaauucuga aa                                            82

<210> SEQ ID NO 252
<211> LENGTH: 136
<212> TYPE: RNA
<213> ORGANISM: Saccharomyces cerevisiae

<400> SEQUENCE: 252
uaucaugaug agcauuuauu uuacugcguu aucguauuga cggggggcugu uuaaguacag    60 ucuguuuuau aaucuauauu cauuuauauu uuauauuucu uaccgaggaa auugacucuu   120
aacagauuug cugaaa                                                  136

<210> SEQ ID NO 253
<211> LENGTH: 101
<212> TYPE: RNA
<213> ORGANISM: Saccharomyces cerevisiae

<400> SEQUENCE: 253
guuuaugaug agaccacguc cuuagugaca augcuauaaa cccagcucuu cgauucguuu    60
uuaaugaaag ggagaagauu uuuuugucaa acgcucugag u                      101

<210> SEQ ID NO 254
<211> LENGTH: 164
<212> TYPE: RNA
<213> ORGANISM: Saccharomyces cerevisiae

<400> SEQUENCE: 254
ugauaugaug auuuguuguc gaccgggcgg acauauuagu aucguuaaaa gggucgccgu    60
cuacucucau cguucuuuug uguacaaauu uuuuaaagga gcgauguuga uggcauuaug   120
guucuuuagu ggagaauuga ugauugguca caagacaucu gauu                   164

<210> SEQ ID NO 255
<211> LENGTH: 89
<212> TYPE: RNA
<213> ORGANISM: Saccharomyces cerevisiae

<400> SEQUENCE: 255
uuauaugaug auaaccuucu cagcucacuc agaucuuuug auaugauuga uaaaaauuuc    60
cuauccaaca uucaucaauu uaucugacc                                     89

<210> SEQ ID NO 256
<211> LENGTH: 91
<212> TYPE: RNA
<213> ORGANISM: Saccharomyces cerevisiae

<400> SEQUENCE: 256
ugaugugaug acaacuucuu gagcuauaua uuuucuugag aacaucaaug aagaaaacgu    60
cucaucaaau gauuugcacg ucagucugau c                                  91

<210> SEQ ID NO 257
<211> LENGTH: 103
<212> TYPE: RNA
<213> ORGANISM: Saccharomyces cerevisiae

<400> SEQUENCE: 257

```
guuuaugaug auuccacau ucacgacgg ucaacugcgu uuuucgaaug uuuaucgauu    60
aacuuugaug auauucgcc ugugacaggg cgugguacug agc                    103

<210> SEQ ID NO 258
<211> LENGTH: 80
<212> TYPE: RNA
<213> ORGANISM: Saccharomyces cerevisiae

<400> SEQUENCE: 258
gcagaagaug aaacaaauua cucaaauaga caagcauaug ucgaucuuc augauugaaa   60 agagcaauua gugucugaug                                              80

<210> SEQ ID NO 259
<211> LENGTH: 85
<212> TYPE: RNA
<213> ORGANISM: Saccharomyces cerevisiae

<400> SEQUENCE: 259
uuuuaugaug agauauuuau agaugacgag ucgaucauu cgugaagaca caacuauuaa   60
aauuaccauu caugccuuuc ugaag                                        85

<210> SEQ ID NO 260
<211> LENGTH: 104
<212> TYPE: RNA
<213> ORGANISM: Saccharomyces cerevisiae

<400> SEQUENCE: 260
uggaaaugag gauccacagc acugggcacu gagggggaaa caaauauccu uucaaaugag  60
ugacaaugcu uuagcgggcc uagaaaaccc gcgcaacuga ucca                   104

<210> SEQ ID NO 261
<211> LENGTH: 84
<212> TYPE: RNA
<213> ORGANISM: Saccharomyces cerevisiae

<400> SEQUENCE: 261
ucauaugaug auuauaacaa aaacaaaagc uggaauuacu ggcugaacga guauauguug  60
auacguuuuu gcacuauccu gacc                                         84

<210> SEQ ID NO 262
<211> LENGTH: 82
<212> TYPE: RNA
<213> ORGANISM: Saccharomyces cerevisiae

<400> SEQUENCE: 262
ucccuugaug accaaaauaa auuuuuacaa acuagaguuu cugaaucuuu ugugauuaga  60
acguuuauuc uuauuucuga gg                                           82

<210> SEQ ID NO 263
<211> LENGTH: 85
<212> TYPE: RNA
<213> ORGANISM: Saccharomyces cerevisiae

<400> SEQUENCE: 263
uuuaaugaug auagcaugau uuauguugcu cgaaguuaau cgaugugagc acaaugauuu  60
cucaagacua caacgguauc ugaau                                        85

<210> SEQ ID NO 264
<211> LENGTH: 109
```

<212> TYPE: RNA
<213> ORGANISM: Saccharomyces cerevisiae

<400> SEQUENCE: 264
guaacugaau gaugauauaa uuugcgaucu agggcuaauc acuuggaaca ccgccauguu    60
cuauaugggu gauuagcgaa gugcgaaaaa uuuuuuaucu gauauuuuc              109

<210> SEQ ID NO 265
<211> LENGTH: 190
<212> TYPE: RNA
<213> ORGANISM: Saccharomyces cerevisiae

<400> SEQUENCE: 265
ggcccugaug auaauggugu cucuucuuuc cucguccgau cgaccauga cgacaaggga    60 uuuuaucucg uucucuuaau gcgaaugauu uugaaaagau guugcuucug ugacauuuuu  120
uuuuaaucau uuguguuugc aaacgggaac uuuucuugcc aguguuauac aacacaugca  180
gaucugagcc                                                        190

<210> SEQ ID NO 266
<211> LENGTH: 451
<212> TYPE: DNA
<213> ORGANISM: Homo sapiens

<400> SEQUENCE: 266
gggttgcgga gggtgggcct gggaggggtg gtggccattt tttgtctaac cctaactgag    60
aagggcgtag gcgccgtgct tttgctcccc gcgcgctgtt tttctcgctg actttcagcg   120
ggcggaaaag cctcggcctg ccgccttcca ccgttcattc tagagcaaac aaaaaatgtc   180
agctgctggc ccgttcgccc ctcccgggga cctgcggcgg gtcgcctgcc cagcccccga   240
accccgcctg gaggccgcgg tcggcccggg gcttctccgg aggcacccac tgccaccgcg   300
aagagttggg ctctgtcagc cgcgggtctc tcggggcga gggcgaggtt caggcctttc    360
aggccgcagg aagaggaacg gagcgagtcc ccgcgcgcgg cgcgattccc tgagctgtgg   420
gacgtgcacc caggactcgg ctcacacatg c                                 451

<210> SEQ ID NO 267
<211> LENGTH: 547
<212> TYPE: DNA
<213> ORGANISM: Oryctolagus cuniculus

<400> SEQUENCE: 267
ttggaaaacc tcgcgatagc cggggacgct cggcctcggc caatccgcgc gcgcagcgcc    60
gctcccttta taagacgact ccggccggcg cgcggcgggc tgaggagggt gggctcggga   120
ggggcccggt catttctcat ctaaccctaa ctgagcaggg cgtaggcgcc gcgcttttgt   180
ttccccgcgc gctgtttttc tcgctgactt tcagcgcgtg ggaaaagcct tggcctaccg   240
ccgtccaccg ttcatttcgc agtaaacaaa aatgtcagc cgctggcgg ttcgcccttc    300 ccggggacct gcggtggctc gcccgcccgg ccccgtgcc ccgcctgagg ccgcggtcgg   360
cccgggcgtt ctccggaggt gcccaatgcc gccgcgaaga gttaggctct gtcagccgcg   420
ggtccctcgg gggccaaggg cgaggcgcag gccgtctggc cgcagggaga ggaacggagc   480
gggtccccca gcgtggtgcg cttccctgag ctgtgggact tgcacccggg actcggctca   540
aacacgc                                                            547

<210> SEQ ID NO 268

```
<211> LENGTH: 517
<212> TYPE: DNA
<213> ORGANISM: Cavia porcellus

<400> SEQUENCE: 268
cctgagactc agtctcgcga cagccgtggc aggcgtcagc caatccgcgc gggcgccgac    60
cactgtttta taaggagcct ctgcgagccg ctgggccggg aggggtggtg gtcttccctg   120
tctaacccta aggtgaagag gacgtgggtg ccgtgttttt cgctcccgca cgctgttttt   180
ctcgctgact ttcagcgtgc agaaaagcct tggcctaccg tcggttattg tctaattaga   240
agcaaacaaa aaatgtcagc gtggccgggc cgccccctccc ggatacctgc ggcggctcgt   300
ccaccggccc ccgagccccg cctaggccgc ggccggcgcg gggcttccct ggaggcgccc   360
atggccgccg cgaagagttc gtctctgtca gctgcgggtc gcccggggggc cgcgggagag   420 tcccaggcct tggccgcagg gagagaaacg gagcaggtcc tcgcgcggtg cactcccctg   480
agctgtggga agtgcaccgg gacgggctcc tacaagc                           517

<210> SEQ ID NO 269
<211> LENGTH: 476
<212> TYPE: DNA
<213> ORGANISM: Cricetulus griseus

<400> SEQUENCE: 269
gcgcgcgaga gttcgagctc cagcgagagc cggcgccggc caatcagcgc gcgccacccc    60
gggtacttaa gggcgacctg gcgggcggct gccagtctaa ccctgaattc tgagagctgt   120
gggtactgtg ctttcgtctc cgcccgctgt ttttctcgct gacttccagc gggcgggaaa   180
gtccagacct gcagcgggcc atcgcgcgtt ttccaccaca aaaaaatgtc agcgctgggc   240
tcatgtgcct ggagccttgc ggccggccgc ccagccccgc accgcctga ggccgcggtc   300 ggcctggagt cctcgggctc cgctgccgcc gcgaagagct agactctgtc agccgcgggg   360
cgtcaggggc tggggcgagc cccggcagcg ccgcaagcag agaaacggag ctggtcccgt   420
gaacggtgac ttccctgagt tgtgggaaat gcaccaggaa ctcggttccc acaacc       476

<210> SEQ ID NO 270
<211> LENGTH: 397
<212> TYPE: DNA
<213> ORGANISM: Mus musculus

<400> SEQUENCE: 270
acctaaccct gattttcatt agctgtgggt tctggtcttt tgttctccgc ccgctgtttt    60
tctcgctgac ttccagcggg ccaggaaagt ccagacctgc agcgggccac cgcgcgttcc   120
cgagcctcaa aaacaaacgt cagcgcagga gctccaggtt cgccgggagc tccgcggcgc   180
cgggccgccc agtcccgtac ccgcctacag gccgcggccg gctggggtc ttaggactcc    240 gctgccgccg cgaagagctc gcctctgtca gccgcgggc gccgggggct ggggccaggc    300
cgggcgagcg ccgcgaggac aggaatgaa ctggtccccg tgttcggtgt cttacctgag   360
ctgtgggaag tgcacccgga actcggttct cacaacc                            397

<210> SEQ ID NO 271
<211> LENGTH: 388
<212> TYPE: DNA
<213> ORGANISM: Rattus norvegicus

<400> SEQUENCE: 271
gtctaaccct attgttatag ctgtgggttc tgttcttttg ttctccgccc gctgtttttc    60
```

```
tcgctgactt tcagcgggcc tggaaagttc agacctgcag cgggtcaccg cgcattctgg      120
aacctcaaaa aatgtcagcg taggagctct ggtgccagag ctccgcggcg ctgggccgcc      180
cagcccggta cccgcctgga ggccgcggac ggcctggggt cttagaactc cgctgccgcc      240
gtgaagagct agtctctgtt agctacgggg caccgggcgc tggggtcagg ccgggagagc      300
gccgcaagga cagtaacgga actggtccct gagttcggtg gctttcctga gatgtgggaa      360
gtgcacctgg aactcagttc ctacaacc                                         388

<210> SEQ ID NO 272
<211> LENGTH: 544
<212> TYPE: DNA
<213> ORGANISM: Felis catus

<400> SEQUENCE: 272
gaggacggat ctcgcgagaa ccgtgacggg agggcttaag ccaatcggcg cgtacggcgg       60
ccgctgtctt tagggagc cgcggcgttt tgcacctcgg gttgtggagg gtgggcctgg        120
gaggggaagc ggtcagtttt tgtctaaccc taactgagaa gggcgtaggc gccgcgcttt      180
tgtttcccgc acgctgtttt tttcgctgac tttcagcggg cggaaaagcc tcggcctacc      240
gccgtccacc gtacagtttg gagcaaacaa aaaatgtcag ctgctgactt gctcgcccct      300
cccaggaccc tgcggtggct cgcctcctta gcccccgcgt cccgcctaga ggccgcggtc      360
ggcccggggc ttctccggag gcacccattg ccgtcgcgaa gagttgggct ctgtcagccg      420 cgggtcccctt gggggggccg agggcgaggc tctgaccgca gggagagaaa cgggagcagg    480
tccccgcgcg cggtgcgctt ccctgagctg tgggacttgc acccgggact gggctcagac     540
acat                                                                  544

<210> SEQ ID NO 273
<211> LENGTH: 443
<212> TYPE: DNA
<213> ORGANISM: Bos taurus

<400> SEQUENCE: 273
gggttgcgga gggtgggccc cgggttggtg gcagccattt ctcatctaac cctaattgag       60
acaggcgtag gcgctgtgct tttggttacc gcgcgctgtt tttctcgctg actttcagcg      120
ggcggaaaag cctcggccta ccgccatcca ccatccagtc tgcaacaaac aaaaaatgtc      180
agccgctggc tcgctcacct ctcccgggaa cctgcggtgg tccgcccgcc cagccccagt     240
gccccgccta ggccgcggt cggccccgtg cttctccgga ggtgtccatt gccgcgtga       300 agagttgggc tctgtcagcc gcgggtcgct cggtgggccg aggcatggct gtaaccgcag     360
ggaaaggaac ggagtggggt ccccgcgcgc ggtgcgcttc cctgagctgt gggacttgca     420
cccgggactc ggctcagaca tcc                                              443

<210> SEQ ID NO 274
<211> LENGTH: 482
<212> TYPE: DNA
<213> ORGANISM: Sus scrofa

<400> SEQUENCE: 274
gagagctgcc ttattctgaa ttcccaaaat gttcagtaaa ttatgatcta aacaggagct       60
gttttcacct attaaaagat gttatcaggc gggttgcaga gggcaggccg ggagaggagt      120
ggccattttt aaaatctgac cctaactgaa acaggtgtag gcactgcact tttgcttcct     180
```

```
cgagcgctgt ttttcttgct gactttcagc ggatggaaga gccaccatcc agtctgaaac    240
aaacaaaaaa tgtcagccac tggctcggtc actgctcccg ggaacctaag agtctcgccc    300
gcccagcccc ccgcttctcc caaagggccc actgcctccg cgaagagttg ggctgtgtca    360
gccgcgggtt tctcggggcc aaggcgaggc tctgaccgca gggaaaggaa gagttcccta    420
agctgtggca tgtgcagcca ggacttggct cagatacttg caaagaaaaa aaaaaaaacc    480
cc                                                                  482
```

<210> SEQ ID NO 275
<211> LENGTH: 540
<212> TYPE: DNA
<213> ORGANISM: Equus caballus

<400> SEQUENCE: 275

```
gagggcggct ctcgcgatag ctccggcagg cgggcctcgg ccaatgggcg cgggcggcgg     60
tgctcccttt ataaggaggt gcggccaggc acgcggcggg tgggggagag tgggtctggg    120
cggggcggcg gtcacgtttt gtctaaccct aactgagctg gcggaggcg ccgcgctttt    180 gctccccgcg cgctgttttt ctcgctgact ttcagcgggc ggaaaagcct cggtctaccg    240
ccacttacca tccagtctgg agtaaacaaa aaatgtcagc cgctggctcg ctcgcccctc    300
ccgggaccct gcgacggctc gcccgcccag ccccgcgcc ccgcctggag gccgcggtcg    360
gcccggggct tctccggagg cgcccaatgc cgccgcgaag agttgggctc tgtcagccgc    420
gggtgcctcg ggggccaggg acgaggctct ggccgcaggg agaggaacgg agcgggtccc    480
cgcgcgcggt gcgcttccct gagctgtggg acgtgcaccc gggactcggc tcaaacacgt    540
```

<210> SEQ ID NO 276
<211> LENGTH: 549
<212> TYPE: DNA
<213> ORGANISM: Elephas maximus

<400> SEQUENCE: 276

```
ggctcagctc tcgcgagagc cagtgggaga aggccttggc caatccgcgc ggtggcggtc     60
tctcccttta taagaggtg cggcggcgcg gctggtgcgg tgggttgagg agggtacgcc    120
cgggagggcg gtggtctgtt ctgttctaac cctaactgat aagggcgtag cgccgtgct    180 tttgttcccc gcgcgttgtt tttctcgctg actttcagcg ggcgggaaaa gcctcggtct    240
accgccgtct accgatagcc tggagcaaac aaaaaaatgt cagccgccgg ccgctcgccc    300
ctcccgggaa cctgcagtgg ctcgcccgcc cagccccgct ccccgcctgg aggccgcggt    360
cggcctgggg cttctccgga ggttcccgct gccgccgcga agagttgggc tctgtcagcc    420
gcgggtcccg cgggaaccaa gggcgaggct ggggcctcct gaacgcaggg agagaaacgg    480
agcggttccc cgcgtgcgtg cgcttccctg agttgtggga tgtgcgctcg ggctcagct    540 ccgacaggt                                                          549
```

<210> SEQ ID NO 277
<211> LENGTH: 465
<212> TYPE: DNA
<213> ORGANISM: Gallus gallus

<400> SEQUENCE: 277

```
acgcgtggcg ggtggaaggc tccgctgtgc ctaaccctaa tcgggggaat tgatggtgct     60
gtcgccgcgc tccctccgcc cgcccgctgt tttactcgct gactttcagc gggcgagagg    120
agccgccccg ggggggaggc gggcggcggg aggggccgg ggcgccgcgg cggtgggggt    180
```

```
cgggggggggg agagaaaggg ccgaaagggg ctccgcggcc aaaaaaacgt cagcgagggg      240
tccgctcgcc ccgatccgcc ctggggtccc cgctcgcgtg gccgcggtcg gccggcaccc      300
gccattgccg ccgcgaagag ttcgcctctg tcagcctcgg cggcgcgcgg gaggtgcggc      360
gcgcggcccc gcgcccccag cagagcaaac gggagcggcg ccccgggggt aaccccgcg      420 ctccccctgcg ccgtggggcg cgcggacggc gtcgctccca cacgc                    465
```

```
<210> SEQ ID NO 278
<211> LENGTH: 520
<212> TYPE: DNA
<213> ORGANISM: Bufo japonicus

<400> SEQUENCE: 278
gaacgcaacg ctacgggtag cagtaagggt agaccgataa ccaatcaaat ggtaatacat       60
acattacgta attttatgta taaatacgta tgttttttta ccggtagttt aattagaggg      120
attggaaggt tccgcttatg ctaaccctaa tattgggggt ctgttgaaaa cctctttaag      180
atatgcgtgt tgttttattg gctgactttc agcgcgcatt gagaggagtt gctgcccagg      240
actaaaaaat gtcagctggg agtccttcct ctcccttatt tctgcctcac aacctggact      300
ctttatttag cggtgcccca tttgtcgagg ccgcagtcag tcttgttctt atacgctgct      360
gttgcgaaga gttcgtctct gtcagcctcc ggggcaacgc cttgaatttg gagagcctgg      420
gaatgtaaca aggggtaggg aaaataacga gagctgagtt ggcttctcct gtgctgttcc      480
tgagctgtgg aacttgcaat cgcagtcggc tctgacactt                             520
```

```
<210> SEQ ID NO 279
<211> LENGTH: 584
<212> TYPE: DNA
<213> ORGANISM: Xenopus laevis

<400> SEQUENCE: 279
ttgccaaggt tacagagcgc gcccccttaa cgcagaagaa ccaatcgact ccctcgaatt       60
gacaggattt cattggctgg aataaagtag gcgggaatcg gcagctactt tttagccagc      120
gtcggaaagt ctttgaatca gcgtttaaag ctcaatgtgg acggaggtct ctgtttcgct      180
aaccctaata cactggcttc agggcgatgg ctcttcgcgg cggtgcctgt tgttttactt      240
gctgactttc agcgggcacg gagagcaagc gtagacgacg actaaaaaac gtcagctggg      300
agactcctcc gttcgcacag cccgacctgc tccattgccc aagagccccg gttttctct      360 gtggaatgta tcaggcgctc cccggtcgt ctgtctgggg ccgcggtcgg catcatctgc       420
tgtcgcgaag agttcgtctc tgttagccct tgggggccct ggtgcggagt ggagagtccg      480
ggtctggggg gtcgggagaa caaaaggggg cgcgctggtg ctcaggctca gtcatgcttt      540
cccttagttg tgggatatgc gtgttcagcc agtccccgac atgt                       584
```

```
<210> SEQ ID NO 280
<211> LENGTH: 317
<212> TYPE: DNA
<213> ORGANISM: Danio rerio

<400> SEQUENCE: 280
gcagagtact ttctctaacc ctaacgcttc tttgcttcct gtacggcttg tatgctgttt       60
tgtcttaagc tttcagcata ttacatgaag ctttccgcgg tttcgatact ttaaaaaagc      120
tatagagtac tctggcgctc ggtctcacag gtttggctgt ttgtacgcgg acagtttgac      180
```

```
tgccgccaag agttcggctc tgctgcacat tcggcaggtc tgtggactgc acaacactga      240
gcagattaac ttgagcatgg cgaaggtttg cggacctcaa acactgatcc tgcaaatacg      300
ccaccgctca gacatgc                                                     317

<210> SEQ ID NO 281
<211> LENGTH: 1413
<212> TYPE: DNA
<213> ORGANISM: Schizosaccharomyces pombe

<400> SEQUENCE: 281
aacgcaacgc ccatgcttag aaggttgaca aggaaaatta atcaaacggt tcttgagggc       60
ttggtgattg atttgaaagt ttgaaggaaa tgattcatag gccttaagta tagtttgcta      120
ttccaaaacc tgtatactgt ctactagaaa gaacgagtag tctgtttagc ttttcagttt      180
gtctggatag ttgttttcga tggatttcga attcctgtac tgcttcgtgt aaccgtactc      240
ttcaactttt cagcattgcg aaattattct ttttagcttt ttttagagtt ttgatcatta      300
ggaatattca taagagaggc tcttcatgga atcgttgacg cgttgcggaa acatagatc       360 attcctaccg ctttttattat ggctgcagac ttcatacttc tgtatacagt aggaaaaaag    420
aggcctggac atcaattgaa tcgctgggtg cagtgtacgt gagtcttctg cctttaaaat      480
tcatttacag tttaatccta cctttcattt gtataaaatc tgtatccatc atttaagtgc      540
ttgtcagatc acaacgaatt tttggtagaa gagtctcgtt tgaattactg aacgttacta      600
aaaatcaagc aatgaagaaa gttttataga tagtttcaat tccccataca aatattaaat      660
tgtattggta acaattttg cttgtgcaaa tttgttggct gaatgctctc gtctatacta       720
gcttcttttg gcatttgtta cggagataaa aagtatggaa cttaaaagag ctattataaa      780
aaaaatgact tgaaggtttt ccttctacat ttaattttgg ttttttggtc gattctttgt      840
ccgtgctaaa tgtacaactt cgtgttgaag gtactatttg gaaggaaaca aaaaccgact      900
tgtggtcaca atgtacattc aaacgaatag caactctggt ctgtattcaa tttccttgaa      960
cttggattct ttgcggcaaa caataatgaa cgtcctgttt ctcaaaaaaa taatgcttag     1020
ggtaagatac tattttacat tacgtgagat ccatggatca aagcttttgc ttgttcgcta     1080
gtaaaatagt tgactaccca ttcattaata ttttgagtgt agctcgtccg ttgttcctct     1140
tgagcgcgtt ttaggttttt ttcacttggt ctgagcaaaa tgttaaaagg aacgggccca     1200 tttttggta tgttttaatg attaaattta aaattactaa ctattcaatt cccaaattat      1260
cagaattgcg tatttagtaa gaacgcggtt gctcatcttt ttattaaaac atgctgaatt     1320
ccgtttccgg tttcaaaatt ttgagaaagt gatgaatctt attataatgt aaaataaatt     1380 taatgtatttt atttgcgtac tagaagagat gaa                                 1413

<210> SEQ ID NO 282
<211> LENGTH: 1301
<212> TYPE: DNA
<213> ORGANISM: Saccharomyces cerevisiae

<400> SEQUENCE: 282
aataaaacta gagaggaaga taggtaccct atgaaaatgt caatggctgt tgcgtttgct       60
taatcgtatt tttttttttt tcagtccgtg ttttttgtac attctacgtt tgagttttcc      120
atcatgcagg cctcagaaat ttggtaggca ctcgatggtg aagagatagt gtcggatttc      180
ggattgatct ttcagttgat agcctgctgc tctttttcttt tccaaagaat ttcgagtatg     240
ctggtgtcag tgtagatgct tgtgtgtgcg caatttgtgg ttttttattg tgtttctact      300
```

```
tatagatggc taaaatctga gtttagaaaa tgcaaaccgt aaattcttaa acactgctat      360
tgcatttagt tgctaaagca gtgttttga  acttattcct gttattcctt cttcgtaccg      420
atcctcttct cgacctaacc ttttaattac catgggaagc ctaccatcac cacacccaca      480
cacaaatgtt acagctaatt gtttattagc aaagtttgca cgagttcgct gtttattttt      540
ttctcgtttt cttataccta gtattttttc tgacactgtt taaggtgaca gaaaaaaagg      600
agtttaagtt agatttgcaa acagacggtg ctaagcgctg tcactttatg tctatcttat      660
cgttaactct ggaaaagaa  aaaggaaaaa gaacgtcagg gaacatgagt atatatagaa      720
atggtttatt ctagtttttt ccgttttttc agtagatttt tgcctttaaa agaataaatc      780
ccactacaaa aagtaaaat  aaaaaatcta ttcactgaac ttactgatga aatttccaaa      840
tgtgccccgt acatcgaacg atgtgacaga gaaaaatacg agtaggtaaa taagccaaaa      900
ggcaagggtg tcctttctta agcatcggtt aggtttgcgg gcgatcagta actgaacaat      960
gacacaagat caagaacgta atttgagatt tttcaagatg gttttttttag gtatctatta     1020 aaactacttt gatgatcaat acggtatttt tgtcgcatta ttttccaagc ggaaggaacc     1080
gtgtgttcat tttatgaatc ttggtgttgt attcacagct acttctccta atgccttcga     1140
tgcatttaga taattttttgg aaacattttt tttcttgatg tatatttttt gtattgtaga     1200
aatcgcgcgt actgtacttg tatatcgctt tataagcgct tttaattgat tgttcatgac     1260 gaggatagg  ggataggcgg aggtatgcct cttaatattt a                         1301

<210> SEQ ID NO 283
<211> LENGTH: 1190
<212> TYPE: DNA
<213> ORGANISM: Saccharomyces pastorianus

<400> SEQUENCE: 283
gagaggaagg tggtaaccta ataacacgtc agcgactggt atgtttgctt gcccttttt       60 aatttgcttc tcaatgtatt ttttccattt gagttttctg ttgataagcc tcagagtttt     120
ggtaggcgcc tagtggtgga acggttgagc cggaatcgcg attgagatgt gatgttagtg     180
ggccattgtg catctttttt atattttggg caatgcgagc acgctagtgc cagtatgcgc     240
ggtttctgtt cttaacgtac ttatagatcg ctacgttatt tcattttga  aaatctgagc     300 ccggggagtg cggatccata catacatgta atttgttgtt gcagtattgc tagagtacat     360
ttttctccgc gattgtctgt cttctttaca ccagttctgt tttccgtctc aacctcttca     420
ttattatgga aagcatctac cattaccaca cccacacacg aacgttaagg ctaatcgtta     480
ttagttgaat ctccatagcc aagctctttt tttttcaat  gttttccgtc gctttccaag     540
tgacagaaaa aaaggagttt gaattaggct tgcaaaggg  gcaatatcaa tgatactgtc     600
acccttaatg tctgatttat cgtcaactct gtaaaggaaa caagagagag aaaggttggt     660
ggagattaaa tctgtagaaa gaggaaggtt tattctagtt attccatttt tcagtagatt     720
tttgcctttt actagaatta atttaaccaa tataaaaggt tcaaggaaaa atctattcac     780
tgaacttatt agaaaacctc aaatgtgttg gatgcattga aaagattaac caaaaaaaaa     840
aaggcacgca agcaggtcaa aagactagga ctcccttcgt ttccttttcc cattttgcctc    900 aagcatcgaa taagtttgcg agcaaaacat aaccgggcaa atgttacaag agaaaataca     960
tgatttggga tcttccttga tggatttgtt tacatatttc tttactcatt ttttgaggat    1020
caatacaata ttcttgtccc atccttgcta agtaaagaa  cgggcattaa tttccgaaca    1080
```

```
gaaagaattg tgtgttcact ttatggtttt cgcattgtac ttttcctact tgcattagca    1140
gttgtttggc tcactacttt tttcgatgct cacgaataat ttttggaacc               1190
```

<210> SEQ ID NO 284
<211> LENGTH: 1544
<212> TYPE: DNA
<213> ORGANISM: Candida albicans

<400> SEQUENCE: 284

```
gtagccattc attattctaa cccatattca atgctcttgg agtgtgaata tactcggtac      60
atgctatttc attaaaggca ttacttcttt tcgttaccat aatcactaac agtttatttg     120
tttatgctgg ttaagacaag tacatgtcca gaatataata ataaccgat tgaaaacccc      180 aggggtctag tgaatcatct gaaagaagca tgtgctttat tgatagtgta tcttttaaat    240
tgagacctac ttcatgtaca ccaagaagtt agacatccgt acatcaaatc aatgtcttga    300
cattgagttg actcctccca ttttgtgaa aagaattgtt cttccataat ttgtatgata    360
ccttgtggag cacaagcagc atagtctttt gcttcgccaa tcacaaatgt tgcatatcca    420
agaatgcaaa tgattgtttt tcaaaaggaa attaaaaacc aagatattgt taatgggttt    480
gaaaatttca tgtttattat ttgcaatcat tagtcattcc ggcggattac ttcatcttag    540
tcactgcatg gtgttattat ctactttgga ggtacttctt ttcattggag ttcaacaacc    600
cccattccca tgctttcttt ttggtttatt gtgattcttt tttagtttga agggaattaa    660
aatatttatc aaacaaaaat agggtagagg ttccctttta tgatgagaaa ctgaaattgg    720
atgttgtgtt tttggtgaaa ttatttttag caggtgtttt ataatggttg aactggagag    780
ccaatgtgga aattgatctg aggttttcaa aacttggggt gcttttttt tcaactaaag     840 tgtccgatcc aagttatctc atctatctgt tgacacattc tctttcttg gcgttttgt     900 cagataaaag gtttaccatt cactttgctg aagttatttt gatactggaa atgcaaccct    960 cttttcattgc actgtctcgt cggcctctgt ccctgcttta agaatccaaa cggtctggtg  1020
aaaagagtca ctctatcaat tgtcattgtt ttctcatatg agtttcacaa atttgtccga  1080
gatttgggtt tatgttattt agaaaacttt tcttttccaa tccagtcaac tcttttgat  1140 gcgacattgt tgggtcataa aagtgtgagt taaattgtgt tgaataaaat cactagccat  1200
gcttctttgg gagtactggt ggatttcccc tgtttacttg tgttttatgt gatttctat   1260 ctaagggctt cccgaattgt ggatagtttc aatactcgaa aaaattggaa gtagggtatg  1320
ttgggtgtga acagatagc attacgtaat tgcaggtaaa gtggttcaca atttgactt   1380 tcgcgctgga ttggtatgaa gaagctctgg agtacgagtt ttatcacata agcatagtat  1440
ctgttggaaa ggtaacattg cacaagaaga atgttgagtg tgaatgtgtg ttatgagatg  1500
agttggattt gagtgactcc tttctattac attttttctt ttct                    1544
```

<210> SEQ ID NO 285
<211> LENGTH: 17
<212> TYPE: DNA
<213> ORGANISM: Homo sapiens
<220> FEATURE:
<221> NAME/KEY: misc_feature
<222> LOCATION: (13)..(13)
<223> OTHER INFORMATION: n is a, c, g, or t

<400> SEQUENCE: 285

```
acatttttg ttnctga                                                     17
```

-continued

```
<210> SEQ ID NO 286
<211> LENGTH: 17
<212> TYPE: DNA
<213> ORGANISM: Homo sapiens
<220> FEATURE:
<221> NAME/KEY: misc_feature
<222> LOCATION: (13)..(13)
<223> OTHER INFORMATION: n is a, c, g, or t

<400> SEQUENCE: 286
gacatttttt gtnctga                                                17

<210> SEQ ID NO 287
<211> LENGTH: 17
<212> TYPE: DNA
<213> ORGANISM: Homo sapiens
<220> FEATURE:
<221> NAME/KEY: misc_feature
<222> LOCATION: (13)..(13)
<223> OTHER INFORMATION: n is a, c, g, or t

<400> SEQUENCE: 287
tgacattttt tgnctga                                                17

<210> SEQ ID NO 288
<211> LENGTH: 17
<212> TYPE: DNA
<213> ORGANISM: Homo sapiens
<220> FEATURE:
<221> NAME/KEY: misc_feature
<222> LOCATION: (13)..(13)
<223> OTHER INFORMATION: n is a, c, g, or t

<400> SEQUENCE: 288
ctgacatttt ttnctga                                                17

<210> SEQ ID NO 289
<211> LENGTH: 17
<212> TYPE: DNA
<213> ORGANISM: Homo sapiens
<220> FEATURE:
<221> NAME/KEY: misc_feature
<222> LOCATION: (13)..(13)
<223> OTHER INFORMATION: n is a, c, g, or t

<400> SEQUENCE: 289
gctgacattt ttnctga                                                17

<210> SEQ ID NO 290
<211> LENGTH: 17
<212> TYPE: DNA
<213> ORGANISM: Homo sapiens
<220> FEATURE:
<221> NAME/KEY: misc_feature
<222> LOCATION: (13)..(13)
<223> OTHER INFORMATION: n is a, c, g, or t

<400> SEQUENCE: 290
agctgacatt ttnctga                                                17

<210> SEQ ID NO 291
<211> LENGTH: 17
<212> TYPE: DNA
<213> ORGANISM: Homo sapiens
<220> FEATURE:
<221> NAME/KEY: misc_feature
<222> LOCATION: (13)..(13)
<223> OTHER INFORMATION: n is a, c, g, or t
```

<400> SEQUENCE: 291
cagctgacat ttnctga                                                                      17

<210> SEQ ID NO 292
<211> LENGTH: 17
<212> TYPE: DNA
<213> ORGANISM: Homo sapiens
<220> FEATURE:
<221> NAME/KEY: misc_feature
<222> LOCATION: (13)..(13)
<223> OTHER INFORMATION: n is a, c, g, or t

<400> SEQUENCE: 292
gcagctgaca ttnctga                                                                      17

<210> SEQ ID NO 293
<211> LENGTH: 17
<212> TYPE: DNA
<213> ORGANISM: Homo sapiens
<220> FEATURE:
<221> NAME/KEY: misc_feature
<222> LOCATION: (13)..(13)
<223> OTHER INFORMATION: n is a, c, g, or t

<400> SEQUENCE: 293
tgcagctgac atnctga                                                                      17

<210> SEQ ID NO 294
<211> LENGTH: 17
<212> TYPE: DNA
<213> ORGANISM: Homo sapiens
<220> FEATURE:
<221> NAME/KEY: misc_feature
<222> LOCATION: (13)..(13)
<223> OTHER INFORMATION: n is a, c, g, or t

<400> SEQUENCE: 294
ctgcagctga canctga                                                                      17

<210> SEQ ID NO 295
<211> LENGTH: 17
<212> TYPE: DNA
<213> ORGANISM: Homo sapiens
<220> FEATURE:
<221> NAME/KEY: misc_feature
<222> LOCATION: (13)..(13)
<223> OTHER INFORMATION: n is a, c, g, or t

<400> SEQUENCE: 295
cctgcagctg acnctga                                                                      17

<210> SEQ ID NO 296
<211> LENGTH: 17
<212> TYPE: DNA
<213> ORGANISM: Homo sapiens
<220> FEATURE:
<221> NAME/KEY: misc_feature
<222> LOCATION: (13)..(13)
<223> OTHER INFORMATION: n is a, c, g, or t

<400> SEQUENCE: 296
gcctgcagct ganctga                                                                      17

<210> SEQ ID NO 297
<211> LENGTH: 17
<212> TYPE: DNA
<213> ORGANISM: Homo sapiens

```
<220> FEATURE:
<221> NAME/KEY: misc_feature
<222> LOCATION: (13)..(13)
<223> OTHER INFORMATION: n is a, c, g, or t

<400> SEQUENCE: 297
ggcctgcagc tgnctga                                                        17

<210> SEQ ID NO 298
<211> LENGTH: 17
<212> TYPE: DNA
<213> ORGANISM: Homo sapiens
<220> FEATURE:
<221> NAME/KEY: misc_feature
<222> LOCATION: (13)..(13)
<223> OTHER INFORMATION: n is a, c, g, or t

<400> SEQUENCE: 298
gggcctgcag ctnctga                                                        17

<210> SEQ ID NO 299
<211> LENGTH: 17
<212> TYPE: DNA
<213> ORGANISM: Homo sapiens
<220> FEATURE:
<221> NAME/KEY: misc_feature
<222> LOCATION: (13)..(13)
<223> OTHER INFORMATION: n is a, c, g, or t

<400> SEQUENCE: 299
cgggcctgca gcnctga                                                        17

<210> SEQ ID NO 300
<211> LENGTH: 12
<212> TYPE: DNA
<213> ORGANISM: Homo sapiens

<400> SEQUENCE: 300 acatttttg tt                                                              12

<210> SEQ ID NO 301
<211> LENGTH: 12
<212> TYPE: DNA
<213> ORGANISM: Homo sapiens

<400> SEQUENCE: 301 gacattttt gt                                                              12

<210> SEQ ID NO 302
<211> LENGTH: 12
<212> TYPE: DNA
<213> ORGANISM: Homo sapiens

<400> SEQUENCE: 302 tgacatttt tg                                                              12

<210> SEQ ID NO 303
<211> LENGTH: 12
<212> TYPE: DNA
<213> ORGANISM: Homo sapiens

<400> SEQUENCE: 303
ctgacatttt tt                                                             12

<210> SEQ ID NO 304
```

```
<211> LENGTH: 12
<212> TYPE: DNA
<213> ORGANISM: Homo sapiens

<400> SEQUENCE: 304
gctgacattt tt                                                           12

<210> SEQ ID NO 305
<211> LENGTH: 12
<212> TYPE: DNA
<213> ORGANISM: Homo sapiens

<400> SEQUENCE: 305
agctgacatt tt                                                           12

<210> SEQ ID NO 306
<211> LENGTH: 12
<212> TYPE: DNA
<213> ORGANISM: Homo sapiens

<400> SEQUENCE: 306
cagctgacat tt                                                           12

<210> SEQ ID NO 307
<211> LENGTH: 12
<212> TYPE: DNA
<213> ORGANISM: Homo sapiens

<400> SEQUENCE: 307
gcagctgaca tt                                                           12

<210> SEQ ID NO 308
<211> LENGTH: 12
<212> TYPE: DNA
<213> ORGANISM: Homo sapiens

<400> SEQUENCE: 308
tgcagctgac at                                                           12

<210> SEQ ID NO 309
<211> LENGTH: 12
<212> TYPE: DNA
<213> ORGANISM: Homo sapiens

<400> SEQUENCE: 309
ctgcagctga ca                                                           12

<210> SEQ ID NO 310
<211> LENGTH: 12
<212> TYPE: DNA
<213> ORGANISM: Homo sapiens

<400> SEQUENCE: 310
cctgcagctg ac                                                           12

<210> SEQ ID NO 311
<211> LENGTH: 12
<212> TYPE: DNA
<213> ORGANISM: Homo sapiens

<400> SEQUENCE: 311
gcctgcagct ga                                                           12
```

```
<210> SEQ ID NO 312
<211> LENGTH: 12
<212> TYPE: DNA
<213> ORGANISM: Homo sapiens

<400> SEQUENCE: 312
ggcctgcagc tg                                                          12

<210> SEQ ID NO 313
<211> LENGTH: 12
<212> TYPE: DNA
<213> ORGANISM: Homo sapiens

<400> SEQUENCE: 313
gggcctgcag ct                                                          12

<210> SEQ ID NO 314
<211> LENGTH: 12
<212> TYPE: DNA
<213> ORGANISM: Homo sapiens

<400> SEQUENCE: 314
cgggcctgca gc                                                          12

<210> SEQ ID NO 315
<211> LENGTH: 65
<212> TYPE: DNA
<213> ORGANISM: Homo sapiens

<400> SEQUENCE: 315
aataagtgat gaaaaaaagc tgacattttg atgatggcca gtgataacaa cattttctg       60 atgtt                                                                  65

<210> SEQ ID NO 316
<211> LENGTH: 65
<212> TYPE: DNA
<213> ORGANISM: Homo sapiens

<400> SEQUENCE: 316
aataagtgat gaaaaaacct gcagctgacg atgatggcca gtgataacaa cattttctg       60 atgtt                                                                  65

<210> SEQ ID NO 317
<211> LENGTH: 94
<212> TYPE: DNA
<213> ORGANISM: Homo sapiens

<400> SEQUENCE: 317
cagcctgaaa tgatgactct ttaaaaaatt agctgacatt tttctgacat ttttctctgg      60
acacagtttt tgccttatga atctgatcag gctg                                  94

<210> SEQ ID NO 318
<211> LENGTH: 94
<212> TYPE: DNA
<213> ORGANISM: Homo sapiens

<400> SEQUENCE: 318
cagcctgaaa tgatgactct ttaaaaaatt cctgcagctg actctgacat ttttctctgg      60
acacagtttt tgccttatga atctgatcag gctg                                  94

<210> SEQ ID NO 319
```

```
<211> LENGTH: 70
<212> TYPE: DNA
<213> ORGANISM: Homo sapiens

<400> SEQUENCE: 319
aaagtgagtg atgaatagtt ctgtggcata tgaatcatta attttgatag ctgacatttt    60
tctgaagtcc                                                          70

<210> SEQ ID NO 320
<211> LENGTH: 70
<212> TYPE: DNA
<213> ORGANISM: Homo sapiens

<400> SEQUENCE: 320
aaagtgagtg atgaatagtt ctgtggcata tgaatcatta attttgatcc tgcagctgac    60
tctgaagtcc                                                          70

<210> SEQ ID NO 321
<211> LENGTH: 17
<212> TYPE: DNA
<213> ORGANISM: Saccharomyces cerevisiae
<220> FEATURE:
<221> NAME/KEY: misc_feature
<222> LOCATION: (13)..(13)
<223> OTHER INFORMATION: n is a, c, g, or t

<400> SEQUENCE: 321
aatagatttt ttnctga                                                  17

<210> SEQ ID NO 322
<211> LENGTH: 17
<212> TYPE: DNA
<213> ORGANISM: Saccharomyces cevevisiae
<220> FEATURE:
<221> NAME/KEY: misc_feature
<222> LOCATION: (13)..(13)
<223> OTHER INFORMATION: n is a, c, g, or t

<400> SEQUENCE: 322
gaatagattt ttnctga                                                  17

<210> SEQ ID NO 323
<211> LENGTH: 17
<212> TYPE: DNA
<213> ORGANISM: Saccharomyces cerevisiae
<220> FEATURE:
<221> NAME/KEY: misc_feature
<222> LOCATION: (13)..(13)
<223> OTHER INFORMATION: n is a, c, g, or t

<400> SEQUENCE: 323
tgaatagatt ttnctga                                                  17

<210> SEQ ID NO 324
<211> LENGTH: 17
<212> TYPE: DNA
<213> ORGANISM: Saccharomyces cerevisiae
<220> FEATURE:
<221> NAME/KEY: misc_feature
<222> LOCATION: (13)..(13)
<223> OTHER INFORMATION: n is a, c, g, or t

<400> SEQUENCE: 324
cagtgaatag atnctga                                                  17
```

```
<210> SEQ ID NO 325
<211> LENGTH: 17
<212> TYPE: DNA
<213> ORGANISM: Saccharomyces cerevisiae
<220> FEATURE:
<221> NAME/KEY: misc_feature
<222> LOCATION: (13)..(13)
<223> OTHER INFORMATION: n is a, c, g, or t

<400> SEQUENCE: 325
tcagtgaata ganctga                                                    17

<210> SEQ ID NO 326
<211> LENGTH: 17
<212> TYPE: DNA
<213> ORGANISM: Saccharomyces cerevisiae
<220> FEATURE:
<221> NAME/KEY: misc_feature
<222> LOCATION: (13)..(13)
<223> OTHER INFORMATION: n is a, c, g, or t

<400> SEQUENCE: 326
ttcagtgaat agnctga                                                    17

<210> SEQ ID NO 327
<211> LENGTH: 65
<212> TYPE: DNA
<213> ORGANISM: Saccharomyces cerevisiae

<400> SEQUENCE: 327
tttttatttc tttctaagtg ggtactggca ggagtcgggg cctagtttag agagaagtag     60
actca                                                                 65

<210> SEQ ID NO 328
<211> LENGTH: 55
<212> TYPE: DNA
<213> ORGANISM: Saccharomyces cerevisiae

<400> SEQUENCE: 328
agtaatcctt cttacattgt atcgtagcgc tgcatatata atgcgtaaaa ttttc          55

<210> SEQ ID NO 329
<211> LENGTH: 55
<212> TYPE: DNA
<213> ORGANISM: Saccharomyces cerevisiae

<400> SEQUENCE: 329
agtaatcctt cttacattgt atcgtagcgc tgcatatata atgcgtaaaa ttttc          55

<210> SEQ ID NO 330
<211> LENGTH: 21
<212> TYPE: DNA
<213> ORGANISM: Saccharomyces cerevisiae

<400> SEQUENCE: 330
aacgtccttc tactattgga a                                               21

<210> SEQ ID NO 331
<211> LENGTH: 25
<212> TYPE: DNA
<213> ORGANISM: Saccharomyces cerevisiae

<400> SEQUENCE: 331
ttctctgtca catcgttcga tgtac                                           25
```

```
<210> SEQ ID NO 332
<211> LENGTH: 21
<212> TYPE: DNA
<213> ORGANISM: Saccharomyces cerevisiae

<400> SEQUENCE: 332
aacgtccttc tactattgga a                                              21

<210> SEQ ID NO 333
<211> LENGTH: 25
<212> TYPE: DNA
<213> ORGANISM: Saccharomyces cerevisiae

<400> SEQUENCE: 333
ttctctgtca catcgttcga tgtac                                          25

<210> SEQ ID NO 334
<211> LENGTH: 25
<212> TYPE: DNA
<213> ORGANISM: Saccharomyces cerevisiae

<400> SEQUENCE: 334
tcaatccgaa atccgacact atctc                                          25

<210> SEQ ID NO 335
<211> LENGTH: 32
<212> TYPE: DNA
<213> ORGANISM: Saccharomyces cerevisiae

<400> SEQUENCE: 335
gaaatttcat cagtaagttc agtgaataga tt                                  32

<210> SEQ ID NO 336
<211> LENGTH: 25
<212> TYPE: DNA
<213> ORGANISM: Saccharomyces cerevisiae

<400> SEQUENCE: 336
ttttatttta ccttttttgta gtggg                                         25

<210> SEQ ID NO 337
<211> LENGTH: 33
<212> TYPE: DNA
<213> ORGANISM: Saccharomyces cerevisiae

<400> SEQUENCE: 337
gaaatttcat cagtaagttc agtgaataga ttt                                 33

<210> SEQ ID NO 338
<211> LENGTH: 24
<212> TYPE: DNA
<213> ORGANISM: Saccharomyces cerevisiae

<400> SEQUENCE: 338
tttattttac cttttttgtag tggg                                          24

<210> SEQ ID NO 339
<211> LENGTH: 32
<212> TYPE: DNA
<213> ORGANISM: Saccharomyces cerevisiae

<400> SEQUENCE: 339
ggaaatttca tcagtaagtt cagtgaatag at                                  32
```

<210> SEQ ID NO 340
<211> LENGTH: 25
<212> TYPE: DNA
<213> ORGANISM: Saccharomyces cerevisiae

<400> SEQUENCE: 340
tttttatttt acctttttgt agtgg                                     25

<210> SEQ ID NO 341
<211> LENGTH: 32
<212> TYPE: DNA
<213> ORGANISM: Saccharomyces cerevisiae

<400> SEQUENCE: 341
tggaaatttc atcagtaagt tcagtgaata ga                             32

<210> SEQ ID NO 342
<211> LENGTH: 25
<212> TYPE: DNA
<213> ORGANISM: Saccharomyces cerevisiae

<400> SEQUENCE: 342 tttttttattt tacctttttg tagtg                                    25

<210> SEQ ID NO 343
<211> LENGTH: 25
<212> TYPE: DNA
<213> ORGANISM: Saccharomyces cerevisiae

<400> SEQUENCE: 343
aatttcatca gtaagttcag tgaat                                     25

<210> SEQ ID NO 344
<211> LENGTH: 25
<212> TYPE: DNA
<213> ORGANISM: Saccharomyces cerevisiae

<400> SEQUENCE: 344
agatttttta ttttaccttt ttgta                                     25

<210> SEQ ID NO 345
<211> LENGTH: 25
<212> TYPE: DNA
<213> ORGANISM: Saccharomyces cerevisiae

<400> SEQUENCE: 345
aaatttcatc agtaagttca gtgaa                                     25

<210> SEQ ID NO 346
<211> LENGTH: 25
<212> TYPE: DNA
<213> ORGANISM: Saccharomyces cerevisiae

<400> SEQUENCE: 346 tagattttttt attttaccttt tttgt                                   25

<210> SEQ ID NO 347
<211> LENGTH: 25
<212> TYPE: DNA
<213> ORGANISM: Saccharomyces cerevisiae

<400> SEQUENCE: 347

```
gaaatttcat cagtaagttc agtga                                        25

<210> SEQ ID NO 348
<211> LENGTH: 25
<212> TYPE: DNA
<213> ORGANISM: Saccharomyces cerevisiae

<400> SEQUENCE: 348
atagattttt tattttacct ttttg                                        25

<210> SEQ ID NO 349
<211> LENGTH: 33
<212> TYPE: DNA
<213> ORGANISM: Saccharomyces cerevisiae

<400> SEQUENCE: 349
ggaaatttca tcagtaagtt cagtgaatag att                               33

<210> SEQ ID NO 350
<211> LENGTH: 24
<212> TYPE: DNA
<213> ORGANISM: Saccharomyces cerevisiae

<400> SEQUENCE: 350
ttttatttta ccttttgta gtgg                                          24

<210> SEQ ID NO 351
<211> LENGTH: 33
<212> TYPE: DNA
<213> ORGANISM: Saccharomyces cerevisiae

<400> SEQUENCE: 351
tggaaatttc atcagtaagt tcagtgaata gat                               33

<210> SEQ ID NO 352
<211> LENGTH: 24
<212> TYPE: DNA
<213> ORGANISM: Saccharomyces cerevisiae

<400> SEQUENCE: 352
tttttatttt accttttgt agtg                                          24

<210> SEQ ID NO 353
<211> LENGTH: 26
<212> TYPE: DNA
<213> ORGANISM: Saccharomyces cerevisiae

<400> SEQUENCE: 353
aatttcatca gtaagttcag tgaata                                       26

<210> SEQ ID NO 354
<211> LENGTH: 24
<212> TYPE: DNA
<213> ORGANISM: Saccharomyces cerevisiae

<400> SEQUENCE: 354 gatttttat tttaccttt tgta                                           24

<210> SEQ ID NO 355
<211> LENGTH: 26
<212> TYPE: DNA
<213> ORGANISM: Saccharomyces cerevisiae

<400> SEQUENCE: 355
```

```
aaatttcatc agtaagttca gtgaat                                          26

<210> SEQ ID NO 356
<211> LENGTH: 24
<212> TYPE: DNA
<213> ORGANISM: Saccharomyces cerevisiae

<400> SEQUENCE: 356
agatttttta ttttaccttt ttgt                                            24

<210> SEQ ID NO 357
<211> LENGTH: 24
<212> TYPE: DNA
<213> ORGANISM: Saccharomyces cerevisiae

<400> SEQUENCE: 357
agatttttta ttttaccttt ttgt                                            24

<210> SEQ ID NO 358
<211> LENGTH: 24
<212> TYPE: DNA
<213> ORGANISM: Saccharomyces cerevisiae

<400> SEQUENCE: 358
agatttttta ttttaccttt ttgt                                            24

<210> SEQ ID NO 359
<211> LENGTH: 18
<212> TYPE: DNA
<213> ORGANISM: Saccharomyces cerevisiae

<400> SEQUENCE: 359
ttccaaaaat tatctaaa                                                   18

<210> SEQ ID NO 360
<211> LENGTH: 25
<212> TYPE: DNA
<213> ORGANISM: Saccharomyces cerevisiae

<400> SEQUENCE: 360
tgcatcgaag gcattaggag aagta                                           25

<210> SEQ ID NO 361
<211> LENGTH: 15
<212> TYPE: DNA
<213> ORGANISM: Saccharomyces cerevisiae

<400> SEQUENCE: 361
tgtggtgtgt gtggg                                                      15

<210> SEQ ID NO 362
<211> LENGTH: 26
<212> TYPE: DNA
<213> ORGANISM: Saccharomyces cerevisiae

<400> SEQUENCE: 362
tgtgggtgtg gtgtgtgggt gtggtg                                          26

<210> SEQ ID NO 363
<211> LENGTH: 25
<212> TYPE: DNA
<213> ORGANISM: Saccharomyces cerevisiae
```

```
<400> SEQUENCE: 363
gtctggccta tggtgctagt agtac                                          25

<210> SEQ ID NO 364
<211> LENGTH: 25
<212> TYPE: DNA
<213> ORGANISM: Saccharomyces cerevisiae

<400> SEQUENCE: 364
acattattat tgttggaaga ggact                                          25

<210> SEQ ID NO 365
<211> LENGTH: 25
<212> TYPE: DNA
<213> ORGANISM: Saccharomyces cerevisiae

<400> SEQUENCE: 365
gatacacctt ccgtttctga cccat                                          25

<210> SEQ ID NO 366
<211> LENGTH: 82
<212> TYPE: DNA
<213> ORGANISM: Homo sapiens

<400> SEQUENCE: 366
gtgttgatga tgagaacctt atattatcct gaagagaggt gatgacttaa aaatcatgct    60
caataggatt acgctgaggc cc                                             82

<210> SEQ ID NO 367
<211> LENGTH: 82
<212> TYPE: DNA
<213> ORGANISM: Homo sapiens

<400> SEQUENCE: 367
gggtcgatga tgagaagctt ctgttttctt gaagagaggt gatgacttaa aaatcatgct    60
caataggatt atgctgaggc cc                                             82

<210> SEQ ID NO 368
<211> LENGTH: 82
<212> TYPE: DNA
<213> ORGANISM: Homo sapiens

<400> SEQUENCE: 368
gggtcaatga tgagaacctt atattgtcct gaagagaggt gatgacttaa aaatcatgct    60
tagtaggatt acgctgaggc ct                                             82

<210> SEQ ID NO 369
<211> LENGTH: 82
<212> TYPE: DNA
<213> ORGANISM: Homo sapiens

<400> SEQUENCE: 369
gggtcgatga tgagaacttt atattgttct gaagagaggt gatgacttaa aaatcatgct    60
caataggatt acgctgaggc cc                                             82

<210> SEQ ID NO 370
<211> LENGTH: 82
<212> TYPE: DNA
<213> ORGANISM: Homo sapiens

<400> SEQUENCE: 370
```

```
ggatcgatga tgagaacctt atattgtcct gaagagaggt gatgacttaa aaatcatgct    60 cataggatt acgctgaggc cc                                              82
```

<210> SEQ ID NO 371
<211> LENGTH: 82
<212> TYPE: DNA
<213> ORGANISM: Homo sapiens

<400> SEQUENCE: 371

```
gggtcaatga tgagaacctt atattgttct gaagagaggt gatgacttaa aaatcatgct    60 cataggatt acgctgaggc cc                                              82
```

<210> SEQ ID NO 372
<211> LENGTH: 82
<212> TYPE: DNA
<213> ORGANISM: Homo sapiens

<400> SEQUENCE: 372

```
gggtcaatga gaaccttata ttgtcctgaa gagaggtgat aacttaaaaa tcatgctcaa    60 tataggatt acgctgaggc cc                                              82
```

<210> SEQ ID NO 373
<211> LENGTH: 82
<212> TYPE: DNA
<213> ORGANISM: Homo sapiens

<400> SEQUENCE: 373

```
gggtcaatga tgagaacctt acattgttct gaagagagat gatgacttaa aaatcatgct    60 cataggatt acgctgaggc cc                                              82
```

<210> SEQ ID NO 374
<211> LENGTH: 82
<212> TYPE: DNA
<213> ORGANISM: Homo sapiens

<400> SEQUENCE: 374

```
gggtcgatga tgagaacctt atattgtcct gaagagaggt gatgacttaa aaatcatgct    60 cataggatt acgctgaggc cc                                              82
```

<210> SEQ ID NO 375
<211> LENGTH: 81
<212> TYPE: DNA
<213> ORGANISM: Homo sapiens

<400> SEQUENCE: 375

```
gggtcgatga tgagaacctt atattgtctg aagagaggtg atgacttaaa aatcatgctc    60
aataggatta cgctgaggcc c                                              81
```

<210> SEQ ID NO 376
<211> LENGTH: 82
<212> TYPE: DNA
<213> ORGANISM: Homo sapiens

<400> SEQUENCE: 376

```
gggtcaatga tgagaacctt atattgtcct gaagagaggt gatgacttaa aaatcatgct    60 cataggatt acgctgaggc cc                                              82
```

<210> SEQ ID NO 377

```
<211> LENGTH: 82
<212> TYPE: DNA
<213> ORGANISM: Homo sapiens

<400> SEQUENCE: 377
gggtcgatga tgagaacctt atattgtcct gaagagaggt gatgacttaa aaatcatgct      60
caataggatt acgctgaggc cc                                               82

<210> SEQ ID NO 378
<211> LENGTH: 82
<212> TYPE: DNA
<213> ORGANISM: Homo sapiens

<400> SEQUENCE: 378
gggtcgatga tgagaacctt atattatcct gaagagaggt gatgacttaa aaatcatgct      60
caataggatt acgctgaggc cc                                               82

<210> SEQ ID NO 379
<211> LENGTH: 81
<212> TYPE: DNA
<213> ORGANISM: Homo sapiens

<400> SEQUENCE: 379
gggtcgatga tgagaaactt atattgtctg aagagaggtg atgacttaaa atcatgctc       60 aataggatta cgctgaggcc c                                                81

<210> SEQ ID NO 380
<211> LENGTH: 81
<212> TYPE: DNA
<213> ORGANISM: Homo sapiens

<400> SEQUENCE: 380
gggtcgatga tgagaacctt atatgttctg aagagaggtg atgacttaaa atcatgctc       60 aataggatta cgctgaggcc c                                                81

<210> SEQ ID NO 381
<211> LENGTH: 82
<212> TYPE: DNA
<213> ORGANISM: Homo sapiens

<400> SEQUENCE: 381
gggtcaatga tgagaacctt atattatcct gaagagaggt gatgacttaa aaatcatgct      60
caataggatt acgctgaggc cc                                               82

<210> SEQ ID NO 382
<211> LENGTH: 82
<212> TYPE: DNA
<213> ORGANISM: Homo sapiens

<400> SEQUENCE: 382
gggtcgatga tgagaacctt atattgtcct gaagagaggt gatgacttaa aaatcattct      60
caaaaggatt atgctgaggc cc                                               82

<210> SEQ ID NO 383
<211> LENGTH: 82
<212> TYPE: DNA
<213> ORGANISM: Homo sapiens

<400> SEQUENCE: 383
gggtcgatga tgagaacctt atattgtcct gaagagaggt gatgacttaa aaatcattct      60
```
caaaaggatt atgctgaggc cc					82

<210> SEQ ID NO 384
<211> LENGTH: 82
<212> TYPE: DNA
<213> ORGANISM: Homo sapiens

<400> SEQUENCE: 384
gggtcgatga tgagaacctt atattgtcct gaagagaggt gatgacttaa aaatcattct		60 caaaaggatt atgctgaggc cc					82

<210> SEQ ID NO 385
<211> LENGTH: 82
<212> TYPE: DNA
<213> ORGANISM: Homo sapiens

<400> SEQUENCE: 385
gggtcgatga tgagaacctt atattgtcct gaagagaggt gatgacttaa aaatcatgct		60 caataggatt atgctgaggc cc					82

<210> SEQ ID NO 386
<211> LENGTH: 81
<212> TYPE: DNA
<213> ORGANISM: Homo sapiens

<400> SEQUENCE: 386
gggtcgatga tgagaacctt atattttctg aagagaggtg atgacttaaa aatcatgctc		60 aataggatta cgctgaggcc c					81

<210> SEQ ID NO 387
<211> LENGTH: 82
<212> TYPE: DNA
<213> ORGANISM: Homo sapiens

<400> SEQUENCE: 387
gggtcaatga tgagaacctt atattgtcct gaagagaggt gatgacttaa aaatcatgct		60 caataggatt acgctgagtc cc					82

<210> SEQ ID NO 388
<211> LENGTH: 82
<212> TYPE: DNA
<213> ORGANISM: Homo sapiens

<400> SEQUENCE: 388
gggtcaatga tgagaaccct atattgtgtt gaagagaggt gatgacttaa aattaccatg		60 ctcaatgatt acgctgaggc cc					82

<210> SEQ ID NO 389
<211> LENGTH: 82
<212> TYPE: DNA
<213> ORGANISM: Homo sapiens

<400> SEQUENCE: 389
aggtcgatta tgagaacctt atattgtcct gaagagaggt gatgacttaa aaatcatgcc		60 caataggatt acgctgaggc cc					82

<210> SEQ ID NO 390
<211> LENGTH: 82
<212> TYPE: DNA

```
<213> ORGANISM: Homo sapiens

<400> SEQUENCE: 390
gggtcagtga tgagaacctt atattgtcct gaagagaggt gatgacttaa aaatcatgct    60 cataggatt acgctgaggc cc                                              82

<210> SEQ ID NO 391
<211> LENGTH: 82
<212> TYPE: DNA
<213> ORGANISM: Homo sapiens

<400> SEQUENCE: 391
gggtcaatga tgagaacctt atattgtcct gaagagaggt gatgacttaa aaatcatgct    60 cataggatt acgctgaggc cc                                              82

<210> SEQ ID NO 392
<211> LENGTH: 82
<212> TYPE: DNA
<213> ORGANISM: Homo sapiens

<400> SEQUENCE: 392
gggtcaatga tgagaacctt atattgttct gaagagaggt gattatttaa aaatcatgct    60 cataggatt acgctgaggc cc                                              82

<210> SEQ ID NO 393
<211> LENGTH: 82
<212> TYPE: DNA
<213> ORGANISM: Homo sapiens

<400> SEQUENCE: 393
gggtcagtga tgagaacctt atattgtcct gaagaaaggt gatgacttaa aaatcatgct    60 cataggatt acactgaggc cc                                              82

<210> SEQ ID NO 394
<211> LENGTH: 82
<212> TYPE: DNA
<213> ORGANISM: Homo sapiens

<400> SEQUENCE: 394
gggtcaatga tgagaacctg atattgccct gaagagagat gatgacttaa aaatcatgtt    60 cataggatt acgctgaggc ct                                              82

<210> SEQ ID NO 395
<211> LENGTH: 82
<212> TYPE: DNA
<213> ORGANISM: Homo sapiens

<400> SEQUENCE: 395
gggtcaatga tgagaaccgt atattgtcct gaagagcggt gatgacttaa aaataatgct    60 cataggatt acgctgaggc cc                                              82

<210> SEQ ID NO 396
<211> LENGTH: 82
<212> TYPE: DNA
<213> ORGANISM: Homo sapiens

<400> SEQUENCE: 396
gggtcaatga tgagaacctt ataatgttct gaagagaggt gatgacttaa aaatcatgct    60 cataggatt acgctgaggc cc                                              82
```

<210> SEQ ID NO 397
<211> LENGTH: 82
<212> TYPE: DNA
<213> ORGANISM: Homo sapiens

<400> SEQUENCE: 397
gggtcaatga tgagaacctt gtattatctt gaagagaggt gatgacttaa aaatcatgct    60 cataggatt acactgaggc cc                                              82

<210> SEQ ID NO 398
<211> LENGTH: 82
<212> TYPE: DNA
<213> ORGANISM: Homo sapiens

<400> SEQUENCE: 398
gggtcaatga tgagaacctt atattgtcct gaagagaggt gatgacttaa aaatcatgct    60 cataggatt acgctgaggc cc                                              82

<210> SEQ ID NO 399
<211> LENGTH: 82
<212> TYPE: DNA
<213> ORGANISM: Homo sapiens

<400> SEQUENCE: 399
gggctgatga tgagaacctt atattgtcct gaaaaaaggt gatgacttaa acatcatgct    60
taatagtatt atgctgaagc cc                                             82

<210> SEQ ID NO 400
<211> LENGTH: 82
<212> TYPE: DNA
<213> ORGANISM: Homo sapiens

<400> SEQUENCE: 400
gggtcaatga tgagaacctt acattgtcct gaagagagat gatgacttaa aaatcatgct    60 cataggatt acgctgaggc cc                                              82

<210> SEQ ID NO 401
<211> LENGTH: 82
<212> TYPE: DNA
<213> ORGANISM: Homo sapiens

<400> SEQUENCE: 401
gggtcaatga tgagaatctt atattgtcct gaagagaggt gatgacttaa aaatcatgct    60 cataggatt acgctgaggc cc                                              82

<210> SEQ ID NO 402
<211> LENGTH: 82
<212> TYPE: DNA
<213> ORGANISM: Homo sapiens

<400> SEQUENCE: 402
gggtcgatga tgagaacctt atattttcct gaagagaggt gatgacttaa aaatcatgct    60 cataggatt acgctgaggc cc                                              82

<210> SEQ ID NO 403
<211> LENGTH: 82
<212> TYPE: DNA
<213> ORGANISM: Homo sapiens

<400> SEQUENCE: 403
gggtcagtga tgagaacctt ctattgtcct gaagagaggt gatgacttaa aaatcatgct    60
caataggatt acgctgaggc cc    82

<210> SEQ ID NO 404
<211> LENGTH: 82
<212> TYPE: DNA
<213> ORGANISM: Homo sapiens

<400> SEQUENCE: 404
gggtcgatga tgagaacctt atattgttct gaagagaggt gatgacttaa aaatcatgct    60
caataggatt acgctgaggc cc    82

<210> SEQ ID NO 405
<211> LENGTH: 82
<212> TYPE: DNA
<213> ORGANISM: Homo sapiens

<400> SEQUENCE: 405
gggtcaatga tgagaacctt atattgtcct gaagagaggt gatgacttaa aaatcatgct    60
caataggatt acgctgaggc cc    82

<210> SEQ ID NO 406
<211> LENGTH: 82
<212> TYPE: DNA
<213> ORGANISM: Homo sapiens

<400> SEQUENCE: 406
gggtcaatga tgagaacctt atattgtcct gaagagcggt gatgacttaa aaatcatgct    60
caataggatt acgctgaggc cc    82

<210> SEQ ID NO 407
<211> LENGTH: 76
<212> TYPE: DNA
<213> ORGANISM: Homo sapiens

<400> SEQUENCE: 407
gggtcaatga tgagatgtta ccttgaagag aaatgatgac gtaaaaatta agttcagttg    60
gattacgctg aggccc    76

<210> SEQ ID NO 408
<211> LENGTH: 83
<212> TYPE: DNA
<213> ORGANISM: Homo sapiens

<400> SEQUENCE: 408
ggccggtgat gagaacttct cccactcaca ttcgagtttc ccgaccatga gatgactcca    60
catgcactac catctgaggc cac    83

<210> SEQ ID NO 409
<211> LENGTH: 74
<212> TYPE: DNA
<213> ORGANISM: Homo sapiens

<400> SEQUENCE: 409
gtgtatgatg acaactcggt aatgctgcat actcccgagt gcgcggtggg gaagccaacc    60
ttggagagct gagc    74

```
<210> SEQ ID NO 410
<211> LENGTH: 72
<212> TYPE: DNA
<213> ORGANISM: Homo sapiens

<400> SEQUENCE: 410
cgcgtgatga cattctccgg aatcgctgta cggccttgat gaaagcacat ttgaacccct    60
ttccatctga tt                                                        72

<210> SEQ ID NO 411
<211> LENGTH: 564
<212> TYPE: DNA
<213> ORGANISM: Tupaia glis belangeri

<400> SEQUENCE: 411
gcagtctact ctcgcgagac gcgtggcggg aggccttcgt ccaatccgcg cgcgcagcgc    60
cttccccttt ataaggacac cgggcaggcg gcgcggaggg agtggagggt gggcccggga   120
cgggcgcgga cccggtaatc taaccctgac tcacaagagg cgtaggcgcc gtgcttttgc   180
tccccgcgcg ctgtttttct cgctgacttt cagcgttcgg aaaagccctg tggcctatcg   240
ccatccacca tcctttctgg aacaaacaga caaaaaaaaa aatgtcagct gctggtccgt   300
tcgctcctcc cgggccctgc ggtggccgcc agcccgccct ctcatccccc gcgtcccgcc   360
tagaggccgc ggtcggcccg gggcttctcc ggaggtgccc attgccgccg cgaagagtta   420
ggctctgtca gccgcgggct ctcggggggc ccagggcgag gtttaggcct cgtggccgca   480
gggacagcaa cggagcgggt ccccgcgagc ctgtgcgcgt ccctgagccg tgggacttgc   540
accggggact ttgctcggac aatc                                          564

<210> SEQ ID NO 412
<211> LENGTH: 545
<212> TYPE: DNA
<213> ORGANISM: Chinchilla brevicaudata

<400> SEQUENCE: 412
cgtgagacca agtgtcgcga gagccgtggc aaggcttcag ccaatccgag cgggcgcctc    60
ctgccctctt tataaggagc ctctgcgcac acgtccgcgg gttgagaatg gtgggccggg   120
aggggaggtg ggcatgtttt gtctaaccct aactaggagg aggacgtagg cgccgtgctt   180
ttgttccccg cgcgctgttt ttctcgctga ctttcagcgt gcggaaaagc cttgcctgc    240 cgtcgaccac tgtctaatta aaagcaaaca aaaaatgtca gcgtggccgg tccgcccctc   300
ccgggtacct gcggcagctc gcccggctgg cccccgagcc ccgcccaggg ccacggctgg   360
cgcggggctt ctccgggagc gccatggccg ccgcgaagag ttcgtctctg tcagccgcgg   420
gtcgcgcggg ggccgcgggg gagtcctagg ccgagtggcc gcaggaagag aaacggagcc   480
tgtccctgtg cacggggcgc ttctctgagc tgtgggaagt gccccgagac tcggctccta   540
caagc                                                               545

<210> SEQ ID NO 413
<211> LENGTH: 546
<212> TYPE: DNA
<213> ORGANISM: Geomys breviceps

<400> SEQUENCE: 413
agaggaacca actctcgcga gagccgtggc tggagctcag ctaatacgca ggcgcggcac    60
gcgcccttta taaggcgcgg gcgcgcgtgg ctcggccggc gtgcctggga gggggggctg   120
```

```
gtcccactct tctaaccta agggtgtcgg ctgtaggcgc cgtgcttttt acttccccgc    180
gcgctgtttt tctggctggc tttcagcgag cggaaaaagc tttggtctac aggccactca    240
ctttgtatcc cgaaaccaaa ttgaaaaaaa aaaatgccag ctccggccgg tccacccctc    300
ccggggtcct gcggcccggc cgcccgcccg aaccccccgc gacccgcctg aggcacggc     360 cggcccgggg cctctgcgga ggtgcccatt gccgccgcga agagttaggc tctgtcagcc    420
gcgggatccg cgcgggccgg gccgcggccg gacgccgatc cgcagggaca gcaacggaac    480
cggccccttc gccctgtgcg cttcccggag ctgtgggatg agcacccggg gtcggctcct    540
acagtt                                                              546
```

<210> SEQ ID NO 414
<211> LENGTH: 496
<212> TYPE: DNA
<213> ORGANISM: Microtus ochrogaster

<400> SEQUENCE: 414

```
gagcgcgaga gtgcaaacac gggcgagagt tgggcgccga ccaatcagcg agcgcgctga     60
cccaggtatt taagggcgtc cgacggggcg gacgggcgac gcgcgcctct tctaacccta    120
aaaactggag ctgtaggtgt tgctctttca gcgtcgcccg ctgttttttct cgctggcttt    180 cagcgggcca gaaagttcag acctctcagc agatcgtcgc gtcgttctca accacaaaaa    240
atgccagcgc aaagcgcgtc agcctagaac cttgcggccc cggccgcccc agccccgcac    300
ccgccttgag gccgcggttg gcctggagtt ctccggactc cgctgccgcc gcgaagagtt    360
cgtctctgtc agccgcggag tatcagggc tggggccagg cccggacagc gtcgcaagta     420
cagtaacgga gctggtcctt gttcggtggc ttccctgagc tgtaggaagt acacccagag    480
ctcggctcct acaacc                                                   496
```

<210> SEQ ID NO 415
<211> LENGTH: 397
<212> TYPE: DNA
<213> ORGANISM: Mus spretus

<400> SEQUENCE: 415

```
acctaacct gattttcatt agctgtgggt tctggtcttt tgttcttcgc ccgctgtttt     60
tctcgctgac ttccagcgga ccagtaaagt ccagacctgc agcgggccac cgcgcgttcc    120
cgagcctcaa aaacaaacgt cagcgcagga gcttcaggtt cgccgggagc tccgcggcgt    180
cgggccgccc agtcccgtac ccgcctacag gccgcggccg gctgggtc ttaggactcc      240 gctgccgccg cgaagagctc gcctctgtca gccgcggggc gccggggct ggggccaggc     300 cgggcgagcg ccgcgaggac aggaatggaa ctggtccccg tgtttggtgt cttacctgag    360
ctgtgggaag tgcacccgga actcggttct cacaacc                             397
```

<210> SEQ ID NO 416
<211> LENGTH: 397
<212> TYPE: DNA
<213> ORGANISM: Mus musculus castaneus

<400> SEQUENCE: 416

```
acctaacct gattttcatt agctgtgggt tctggtcttt tgttctccgc ccgctgtttt     60
tctcgctgac ttccagcggg ccaggaaagt ccagacctgc agcgggccac cgcgcgttcc    120
cgagcctcaa aaacaaacgt cagcgcagga gcttcaggtt cgccgggagc tccgcggcgc    180
cgggccgccc agtcccgtac ccgcctacag gccgcggccg gctgggtc ttaggactcc      240
```

```
gctgccgccg cgaagagctc gcctctgtca gccgcggggc gccggggget ggggccaggc    300 cgggcgagcg ccgcgaggac aggaatggaa ctggtccccg tgttcggtgt cttacctgag    360
ctgtgggaag tgcacccgga actcggttct cacaacc                            397
```

```
<210> SEQ ID NO 417
<211> LENGTH: 541
<212> TYPE: DNA
<213> ORGANISM: Mustela putorius furo

<400> SEQUENCE: 417
ccggctccgg ctctcgcgag agccgagaca ggggctccgg ccaatcggcg cgggccgcgg    60 ccgctcccctt tatagggaga cgcggccggg tgcagttcgg gttgcggagg gtgggctcgg   120
gaggggtggc ggtcattttc tgtctaaccc taactgaaac gggcgtaggc gctgcgcttt   180
tgttccccgc acgctgtttt tctcgctgac tttcagcggg cggaaaagcc ttggcctact    240
gccacacacc atccagtttg gagcaaacaa aaaatgtcag cggctggcct gctcgcccct    300
cccgggagcc tgcggcgact cgcccgctta gccccgcat cccgcctgga ggccgcggtc     360
ggcccggggc ttctccggag gcacccattg ccgtcgcgaa gagttgggct ctgtcagccg    420
cgggaccctt gggggccaag ggcgaggctc tggccgcagg gagagaaacg gagcgggtcc    480
cctcgcgcgg tgcgcttccc tgagctgtgg gacttgcacc cgggactagg ctcacacaca    540
c                                                                   541
```

```
<210> SEQ ID NO 418
<211> LENGTH: 542
<212> TYPE: DNA
<213> ORGANISM: Procyon lotor

<400> SEQUENCE: 418
ctgaggccgg ctctcgcgag agccgagaca ggggctccgg ccaatcggcg cgggccgcgg    60 ccgctcccctt tatagggaga cgcggcgggc tgtagctcgg gttgcggagg gtgggcctgg   120
gaggggtggc ggtcgtttta tgtctaaccc taactgagaa gggcataggc gctgcgcttt   180
tgttccccgc acgctgtttt tctcgctgac tttcagcggg cggaaaagcc tcggcctact    240
gccatccacc atccagtttg gagcaaacaa aaaatgtcag ccgccggcct gctcgcccct    300
cccgggatcc tgcggtggct cgcccgctta gccccgcgt cccgcctgga ggccgcggtc    360
ggcccggggc ttctccggag gcacccattg ccgtcgcgaa gagttgggct ctgtcagccg    420
cgggaccttt gggggccaag ggcgaggctc tggccgcagg gagagaaaac ggagcgggtc    480
cccttgcgcg gtgcgcttcc tgagctgtgg gacttgcac ccgggactag gctcacacac     540
at                                                                  542
```

```
<210> SEQ ID NO 419
<211> LENGTH: 548
<212> TYPE: DNA
<213> ORGANISM: Suncus murinus

<400> SEQUENCE: 419
gactttaaac atcgcgagat ttgcagcggg accatctcag ccaatcagcg cggccggcgg    60
caactgtact taagcggaga cgcggcgccg ccatgttggc gggttgcggg agctgcgagc    120
ggccgtctcg tctaacccta aagagaaagg cgtaggtgct tggccttggc gactcgcccg    180
ctgttttttg gctggctttc agcgggtgaa gaggcccaag acctaccgcc acccaccgtc    240
```

```
tagtgtctta agggcacaaa gtcctgcccg ccacccttcg aggagcgaaa cccaaaaaag    300 tcagccctg gccgcctctc gccctctcgc aacccgcctc cgtcccagcc tccatccccg     360
ccccaggccg cggtcggtcc gggcttcttc ggaagtcccg ttgccgtcgc gaagagttcg    420
cctctgtcag ccgcggggct tggggccagg acgggaccc tgtccgcagg gagagaaact    480
ggagccgggc cctccacggt gcctccccga gctgtgggat ctgcacccgg gactcgaacc    540
ctacactt                                                            548
```

<210> SEQ ID NO 420
<211> LENGTH: 545
<212> TYPE: DNA
<213> ORGANISM: Dasypus novemcinctus

<400> SEQUENCE: 420

```
ggctctcgcg agagccagtg gcgggctggc gggcctcggc caatccgcgc cgccgcctcg     60
ttccctttat aaggaggctg cgcgcgccca cggcgggtt gcggagggag ggcccgggag    120
gggtgagcgt ccattatcgt ctaaccctaa ctgagatggg cgtaggcgcc gcgcttttgc    180
ttcccgcgcg ctgttttcct cgctgacttt cagcgggcgg aaaagcctcg gcctactgcc    240
gtctactgtc gtatctggag caaacaaaaa atgtcagccg ctggtccgct cgccccatcc    300
gggaacctgc ggtggctcgt ccgccctgcc cccgcgctcc gcctagaggc cgcggtccgc    360
ccggggcttc tccggaggca cccaatgcag ccgcgaagag ttaggctctg tcagccgcgg    420
atcccgcggg ggccaagggt gaggcttagg ccgcgggccg caggaagaaa aaccgagcga    480
gttctcacgc gcggtgcgct tccctgagct gtgggtcgtg cgcctgggac tcggctcaga    540
cacgt                                                              545
```

<210> SEQ ID NO 421
<211> LENGTH: 614
<212> TYPE: DNA
<213> ORGANISM: Dasyurus hallucatus

<400> SEQUENCE: 421

```
cgtttggatc ctttggctcg tcttctggcg gctgcggcga ccaatgagcg cgtccggggc     60
cgggtcttgg ggaaggtata agagaggtgt gcaggcgagc cgggctgtgc ggacgggctg    120
cgtgggcggg tcggtccgtc ctggcacatc taaccctaaa tgcgcgctgg ttgaagtggc    180
ttctcctggg cgatcgctcg ctgttttttgt ggctggcttt cagcgggctg gaggagccgg    240
gagcggaggc ggaggaccga gccaaaaacg tcagccgagg ccgggcggcc ccgctcgtgg    300
cccgtccgca ctgtccgggc caggcccggg cccgaacccc ctggagacaa ctcccgcagg    360
gtctgcgctg cgccgcggag ccccggctgc ccacgtagag gcggcggccg tctcggggcc    420
cctgcgtgcg gggcgcccac tgcggccgcc aagagctcgt ctctgtcagc ctcgggtgca    480
cgtgggcccg cggtcgagcc ctaaggccgg gcgtggggct ggggtcgcag ggagagtaac    540
cgtgagccgg cgcccagcct tcagggcgct ccctcgagct atgggagctg ccccggggca    600
cggctcggac accc                                                    614
```

<210> SEQ ID NO 422
<211> LENGTH: 554
<212> TYPE: DNA
<213> ORGANISM: Trichechus manatus

<400> SEQUENCE: 422

```
agatctgctg tcgcgagagc cagtggcgag aaagccttgg ccaatccgcg cgggcggcgg     60
```

```
cctctcccett tataaggaga cttggcgcgc gaggcttggc gtggagggtt gaggatggcg      120 ccccegggtc gggcagtggt cttttttgtt ctaaccctaa ctggcaaggg cgtaggtgct      180
gtgcttttgt tccccgcgcg ttgtttttct cgctgacttt cagcgggcgg gaaaagccct      240
ggcctaccgc cgtctaccga tagtttggag caaacaaaaa aatgtcagcc gctggccgct      300 caccectecc gggaacctgt ggtggctcgc ccgcccagcc ccgcgcccg cctggaggcc      360 gcggtcggcc tggggcttct ccggaggttc ccattgccgc cgcgaagagt taggctctgt      420
cagccgcggg tcctgcggga accaagggcg aggcttaggc ctcctgaacg cagggagaga      480
aatggagcga ttccccgagt acgtgtgctt ccctgagttg tgggatgtgc gtccgggact      540
cagctccgac aggt                                                        554
```

<210> SEQ ID NO 423
<211> LENGTH: 538
<212> TYPE: DNA
<213> ORGANISM: Anodorhynchus hyacinthinus

<400> SEQUENCE: 423

```
cagccgcagc caatgcggca gaggtgggcg ccgcttctga ccaatggagg cgcggtgggc       60
gtggccgcgg agggtttaag aggcgccgcg aggggggccgc ttgtcgcgtg cggatgggg      120 aggctccagt ctcactaacc ctaatggctg ccgccgtgct ccccgcaccc gtccgctgtt      180
ttattcgctg actttcagcg gacggggga gccgcctggg ggggaagggg tttgcaatca      240
aaaaacgtca gcgacgggtc tccccagccc agcccgccct ggggtctccg tcccccacg      300 cagccggggg cctgccgcgg aggctccctc cgccgcactt cacggaggcc gcggtcggcc      360
ggtgtccgcc actgccgccg cgaagagttc gtctctgtca gcctcggcgg cggtggggag      420
cgagagggct cgtccccgcg ccggggaccc cagcagagca aaacggagcg gcgtcctcgg      480
cacagccgcc gcgcttccct caaccgtggg atgcgcggac ggcgccgctt cgacaccc       538
```

<210> SEQ ID NO 424
<211> LENGTH: 513
<212> TYPE: DNA
<213> ORGANISM: Chelydra serpentina

<400> SEQUENCE: 424

```
cccgccgagc caatgggaat agaggagact cccgctagcc aatccatgcg cgggagggcg       60
ggacggtgga aggtatataa gacccgcggc caggcgggtc tgaccgctgc ggcggcaggt      120
gggggctcag tctttctaac cctaagcgaa atgtgacccc tccccgctgc agccgtccgc      180
tgttttactc gctgactttc agcggacggg gggagcgggt ggagacgcca accaaaaaac      240
gtcagcgagg ggccctcccc tcccacgccg acctgggcct gtggtggggc ccgccagcga      300
agtccccgcc gccccgcccc ggtgaggccg cggtcagccg gctcgcgcca ctgctgccgc      360
gaagagttcg tctctgtcag cctcggggc ggccggggtg gaaggcggg tcccgagccc       420 gtcggccggg agagcaaacg tgagcggcag cccctgcgcc accgccctcc cctaagctgt      480
ggggcccgcg gtcggggctg cgctcagaca cgc                                   513
```

<210> SEQ ID NO 425
<211> LENGTH: 520
<212> TYPE: DNA
<213> ORGANISM: Bufo japonicus

<400> SEQUENCE: 425

```
gaacgcaacg ctacgggtag cagtaagggt agaccgataa ccaatcaaat ggtaatacat    60
acattacgta attttatgta taaatacgta tgttttttta ccggtagttt aattagaggg   120
attggaaggt tccgcttatg ctaaccctaa tattggggt  ctgttgaaaa cctctttaag   180
atatgcgtgt tgttttattg gctgactttc agcgcgcatt gagaggagtt gctgcccagg   240 actaaaaat  gtcagctggg agtccttcct ctcccttatt tctgcctcac aacctggact   300
ctttatttag cggtgcccca tttgtcgagg ccgcagtcag tcttgttctt atacgctgct   360
gttgcgaaga gttcgtctct gtcagcctcc ggggcaacgc cttgaatttg agagcctgg   420 gaatgtaaca aggggtaggg aaaataacga gagctgagtt ggcttctcct gtgctgttcc   480
tgagctgtgg aacttgcaat cgcagtcggc tctgacactt                         520

<210> SEQ ID NO 426
<211> LENGTH: 507
<212> TYPE: DNA
<213> ORGANISM: Ceratophrys ornata

<400> SEQUENCE: 426
gtaataggtt gtaagtttcc cgccacgctc cgtctggaca gcgcagccgg cgagcggtga    60
cgtcatgtta cgtataaaag tcagacccgg ccaatgcggc ttacagtggg aataggaggg   120
agtctatatt tctaaccctc atataccccgg ttcagggctc ttatgtggcg ctcgttgttt   180
tgccggttgc ctttcagcgg gcgaaagagc tcagagaagc gaggaccaaa aaacggcagc   240
cgcgggccct cctgttccca ccatcccagc ttttccacac tgcgcctggg ttctcactca   300
agtgttcggc agcttccact tacgaggccg cggtctaccg ctgtcactgg tagtcgcgaa   360
gagttcgtct ctgtcagcct gggagccgc ggacggagta tgaggtccag taatgagagc   420
agggaagagt aaagcgagcc gcgctacttg tcctatctgc cgctcctaag ctgtggggcg   480
tgtagggtac acaaggctcc gacattc                                       507

<210> SEQ ID NO 427
<211> LENGTH: 499
<212> TYPE: DNA
<213> ORGANISM: Pyxicephalus adspersus

<400> SEQUENCE: 427
ctgatccacc ctaaccccctc cctcctgagg tcaggccgtc caataaacgg agagcagtga    60
cgtcacatgt agtataaaag aacatgtcgg cagaggcgcc ctccagcggt aataggagag   120
ttctatcctt ctaaccctaa tgcacagacc cctcgctgct cttcatgctc gttgtttttc   180
tcgctgactt tcagcgggcg aaagagcaat ggaagctcag gactaaaaaa cgtcagccgt   240
aggctttcct atagccgcag gcctgcctgt cagtgtgcgc ggcctctgct cgcaatgtcc   300
gcagcgcctt cctatgaggc cgcagtctgc caataccccg ggcagccgcg aagagctcgt   360
ctctgtcagc ctttggcgct gcggcggagt ggggaggcc gctgatggca gctgagaata   420
aagcgagccc agctgccccg ctctgttcca ctgcccctga gctgtggggt tggtgaattg   480
cagcatggct ccgacaact                                                499

<210> SEQ ID NO 428
<211> LENGTH: 565
<212> TYPE: DNA
<213> ORGANISM: Dermophis mexicanus

<400> SEQUENCE: 428
tcctacagcc gcagacgcaa ttgaaaaaac gtgcgaacca atcagctgcc ggttacaggt    60
```

```
gcgtcactgg tgtgcgggtg aaaatgaatg tataaataca ggagcacgta accatatcac    120
tctctccgga gagggcggt ttctctgtct tctaaccctca atgcggtgct tcggcagaag    180
ctctccactg cgtacgctca ctgttttcct agctaacttt cagtgagcag ggagagcgaa    240
gtccagtttc acgacaacgg agaaaaaatg ttagctgggg aacgtccctt tcccgagagc    300
ccgcgccgtc cttttcttc ctcgggcccg ttggcatagc ccctggcctc ctcgctctat     360
aggccgcggt cagctcgggc cccagctccg gcagggttc cactgctgcc gcgaagagtt     420
cgcctctgtc agccttgagg tggccgggat agaataggcg ggctcgcggc agcgcgcggg    480
aaagagcaaa tggtgaactg ggtgcctgtt ggggtcgcgt ccctgaagag tgggaagtgc    540
gatctgtgtt cctgttcaga cacac                                          565

<210> SEQ ID NO 429
<211> LENGTH: 556
<212> TYPE: DNA
<213> ORGANISM: Herpele squalostoma

<400> SEQUENCE: 429
tgctaacgcc ggctgcagac gcaacttaaa ttctgcgaac caatcagctt ccagctagag     60
ggcgcgtgag ttggaatggg tgtataaaaa ggggaaccag ccacagaacc attctctctg    120
gagcggggcg atttctcttc cttctaaccc taatgcggtg cttaggcgac agttctccgg    180
gtgcgctcgc tgttttctg gctaactttc agcgagcgga gagagcgaag ccgtggttta    240
cgacgataga ggagaaaaaa tgttagctgg ggaacgtccc tttcccgaga gcccgcgcca    300
tcctcttcct cgggcccatt ggcgatagcc cccggcctcc ctcgctcacc aggccgcggt    360
cagcccgggc cctggctctg ctagggcgtc caatgctgcc gcgaagagtt cgtctctgat    420
tgccttgagg tagccgggct cgaataggtg ggctcgcggc gatgcgcagg aaagagcaaa    480
acagtgaact gggcgtgtgc tggggtcgcg tccctgaagt gtgggatgtg cgatctgtcc    540
gcttgttcag acattg                                                    556

<210> SEQ ID NO 430
<211> LENGTH: 554
<212> TYPE: DNA
<213> ORGANISM: Typhlonectes natans

<400> SEQUENCE: 430
acctaggatg ttcgaaccaa tcagctgccg actggaggaa ccaatcagct gccggctgga     60
ggcgcgcggt gaaaacgaga gtataaaatg cagaacttgc actcatagca ttgtcattcc    120 ggagagggc gttttcttct ttctctaacc ctaatgtatt gcttgggcag cagctctctc    180
ggtatgctcg ctgttttgct ggctaacttt cagcgagcag agggcgaagt cgaatttcgg    240
acaagggaga aaaaatgtta gccggggaac gccccttttcc cgaatgcccg tgccgtcctt    300
cctctcctct gggcccgttg gcgatagccc ccggcctccc tcgctcctta ggccgcggtc    360
agtccgggcc cttgctctgg catgaggtcc attgctgccg cgaagagttc gtctctgtca    420
gccttgaggt ggccagcatg gaattggcgg gcttgtggcg gcgcgcggga aaaagcaaat    480
ggtgaactag gtgcgtgttg tggtcgtgtt cctgaagcgt ggaatgtgcg atctgtgcgc    540
tagttcatac acac                                                      554

<210> SEQ ID NO 431
<211> LENGTH: 312
<212> TYPE: DNA
```

<213> ORGANISM: Oryzias latipes

<400> SEQUENCE: 431

```
gcggggtgtt ctacctaacc ctaattagag gctgcctcgt gtacttaacg tatgctgttt        60
tgttgtttct ggctttcagc agactacatg aggcgttggg cgtgaagctt gaaaatatcc       120
gtacaaaaaa agccagaaaa gactccccgt cgcgctcagt tccctgctgg aaacgccgcg       180
gtcagctcgg ctgctgcgaa gagttcgtct ctgttgtttc ggggattgtc aacagctgag       240
cagataaaaa tgagcaaggc gatcctgccg aacctcatgt ggtccggttc ggtatcctac       300
gctcagacaa at                                                           312
```

<210> SEQ ID NO 432
<211> LENGTH: 348
<212> TYPE: DNA
<213> ORGANISM: Gasterosteus aculeatus

<400> SEQUENCE: 432

```
acggagtgtc tcttctaacc ctaaatacgg aggccctcct gtactcaacg tttgctgttt        60
ttttctggct tttcagtaaa ctacgggagg ggctgacgcg acgctgggaa cgtttccgaa       120
cgacaaccaa aaaaaagcca agatgaccac tccgtcgtgt tcagtgtccc gcctgaaaca       180
ccgcgaattt cctgccgtgg tcggcttgtg ctgccgcgaa gagttcgtct ctgttgctcc       240
ggtgttctca tggcgggact tgtgataact gagcagagta aaactgagca gggcgactct       300
cccagatcgt tccagtgatc cggtcagaaa gcccccgctc aaacaccc                    348
```

<210> SEQ ID NO 433
<211> LENGTH: 325
<212> TYPE: DNA
<213> ORGANISM: Takifugu rubripes

<400> SEQUENCE: 433

```
acggagtgtc tcttctaacc ctaaattatc tcggctccct gtactcggcg tttgctgttt        60
ttgtctggct ttcaggaaac tacagggagt cttggacgtc tcggttcacg gatcaaaaaa       120
gccaagaaaa tcactccgtc gcgttcaggt ccccccagg aacaccgaga gccctgttgt        180
ggtcagtccg gctgccgcaa agagttggtc tctgctgctc cggtgtcttg gcgggatcac       240
caaggactga acagagaaac agtgagcgtg gtgactctac cggttcttcc aatgtcccgg       300
ttaggatacc caagctcaaa cactc                                              325
```